United States Patent
Anekella et al.

(10) Patent No.: US 11,243,212 B2
(45) Date of Patent: Feb. 8, 2022

(54) LIPOSOMAL PREPARATIONS FOR NON-INVASIVE-PRENATAL OR CANCER SCREENING

(71) Applicant: SeraCare Life Sciences, Inc., Milford, MA (US)

(72) Inventors: Bharathi Anekella, Clarksburg, MD (US); Russell Garlick, Needham, MA (US); Catherine Huang, Elkridge, MD (US); Seth Harkins, Bethesda, MD (US); Yves Konigshofer, Potomac, MD (US); Alice Ku, Clarksburg, MD (US); Farol Tomson, Germantown, MD (US)

(73) Assignee: SeraCare Life Sciences, Inc., Milford, MA (US)

( * ) Notice: Subject to any disclaimer, the term of this patent is extended or adjusted under 35 U.S.C. 154(b) by 374 days.

(21) Appl. No.: 15/571,689

(22) PCT Filed: May 6, 2016

(86) PCT No.: PCT/US2016/031291
§ 371 (c)(1),
(2) Date: Nov. 3, 2017

(87) PCT Pub. No.: WO2016/179530
PCT Pub. Date: Nov. 10, 2016

(65) Prior Publication Data
US 2018/0149660 A1 May 31, 2018

Related U.S. Application Data

(60) Provisional application No. 62/254,898, filed on Nov. 13, 2015, provisional application No. 62/171,672, (Continued)

(51) Int. Cl.
*C12Q 1/6883* (2018.01)
*G01N 33/68* (2006.01)
(Continued)

(52) U.S. Cl.
CPC ......... *G01N 33/689* (2013.01); *C12Q 1/6806* (2013.01); *C12Q 1/686* (2013.01); *C12Q 1/6883* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 5,540,923 A | | 7/1996 | Ebbesen et al. |
| 5,593,848 A | * | 1/1997 | Levine et al. ............ 435/7.24 |

(Continued)

FOREIGN PATENT DOCUMENTS

| | | |
|---|---|---|
| WO | WO-02/18635 A2 | 3/2002 |
| WO | WO-02/018635 A3 | 3/2003 |

(Continued)

OTHER PUBLICATIONS

Berg, E.S. et al. Journal of Microbiological Methods 55:303-309. (Year: 2003).*

(Continued)

*Primary Examiner* — Diana B Johannsen
(74) *Attorney, Agent, or Firm* — Foley Hoag LLP; Dana M. Gordon; Mohanad Mossalam

(57) ABSTRACT

Disclosed are controls for use in identifying any of a number of genotypes and/or for use in identifying or characterizing a disease or condition. The controls may be particularly useful for diagnostic tests that utilize circulating cell-free DNA or microRNA. A control may comprise a mixture of nucleic acids. In some embodiments, a control comprises liposomes, e.g., wherein nucleic acids of the control are associated with the liposomes. For example, the controls are useful for determining whether a fetus comprises an aneuploidy. Also disclosed are methods of using the controls.

13 Claims, 23 Drawing Sheets

Related U.S. Application Data filed on Jun. 5, 2015, provisional application No. 62/157,729, filed on May 6, 2015.

(51) Int. Cl.
   *C12Q 1/6806* (2018.01)
   *C12Q 1/686* (2018.01)

(56) References Cited

U.S. PATENT DOCUMENTS

| | | |
|---|---|---|
| 2005/0272083 A1 | 12/2005 | Seshagiri |
| 2006/0105360 A1 | 5/2006 | Croce et al. |
| 2010/0062494 A1 | 3/2010 | Church et al. |
| 2010/0286143 A1 | 11/2010 | Dias-Santagata et al. |
| 2014/0099648 A1 | 4/2014 | Walker et al. |
| 2014/0287946 A1 | 9/2014 | Marble |
| 2014/0371078 A1 | 12/2014 | Abdueva |
| 2018/0149660 A1 | 5/2018 | Anekella et al. |

FOREIGN PATENT DOCUMENTS

| | | |
|---|---|---|
| WO | WO-2010/033639 A2 | 3/2010 |
| WO | WO-2010/033639 A9 | 2/2011 |
| WO | WO-2014/022852 A1 | 2/2014 |

OTHER PUBLICATIONS

International Search Report and Written Opinion for International Application No. PCT/US2016/031291 dated Aug. 12, 2016.

Puszyk et al., "Noninvasive prenatal diagnosis of aneuploidy using cell□free nucleic acids in maternal blood: promises and unanswered questions," Prenat Diagn, 28:1-6 (2008).

Yamada et al., "Development of efficient packaging method of oligodeoxynucleotides by a condensed nano particle in lipid envelope structure," Biol Pharm Bull, 28(10):1939-1942 (2005).

Bisanz et al., "Targeting ECM-Integrin Interaction with Liposome-Encapsulated Small Interfering RNAs Inhibits the Growth of Human Prostate Cancer in a Bone Xenograft Imaging Model," Molecular Therapy, 12(4): 634-643 (2005).

Extended European Search Report issued by the European Patent Office in corresponding Application No. PCT/US2016031291, dated Aug. 21, 2018.

Oliveira et al., "Cationic Liposome—DNA Complexes as Gene Delivery Vectors: Development and Behaviour Towards Bone-Like Cells," Acta Biomaterialia, 5(6): 2142-2151 (2009).

Wong et al., "DNA vaccination against Respiratory Influenza Virus Infection," Vaccine, 19(17-19): 2461-2467 (2001).

Extended European Search Report issued by the European Patent Office in corresponding Application No. PCT/2016031291, dated Dec. 3, 2018.

\* cited by examiner

Figure 2
A
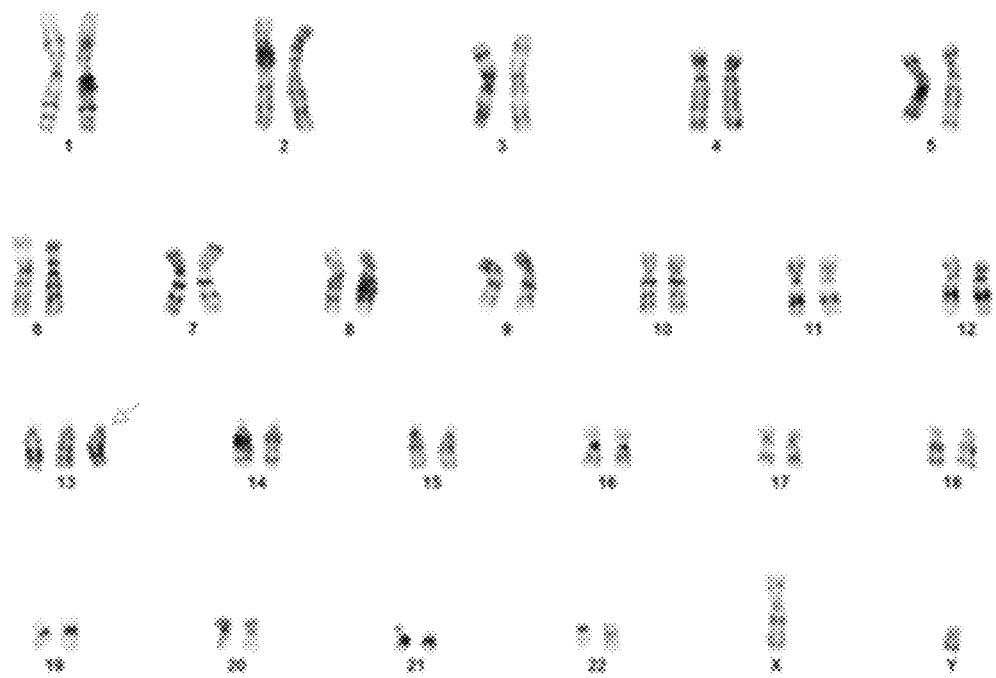
B
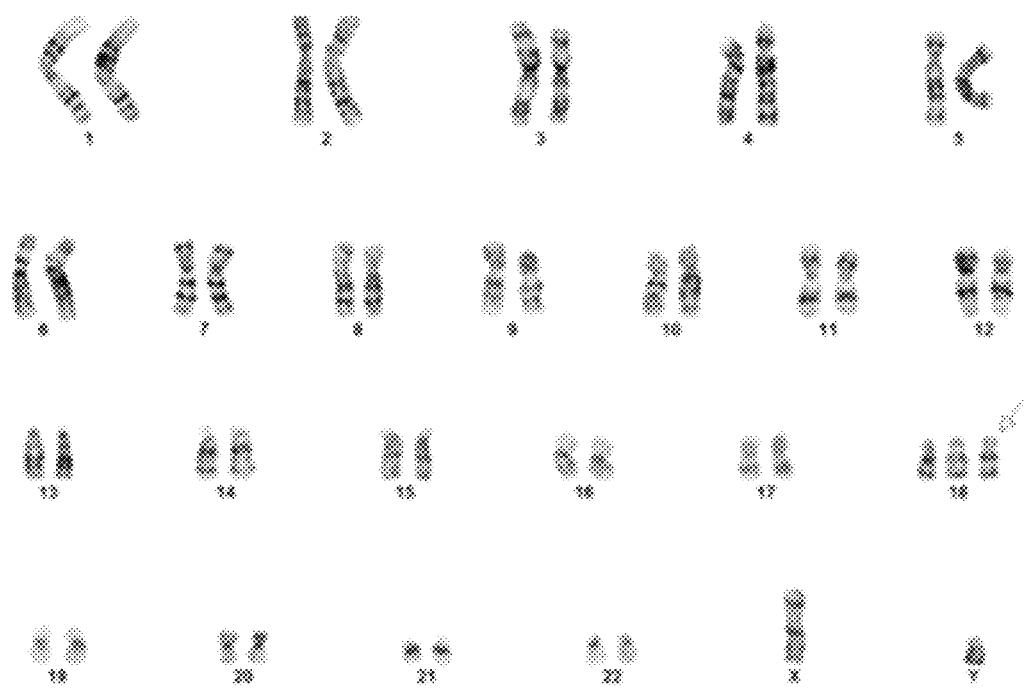

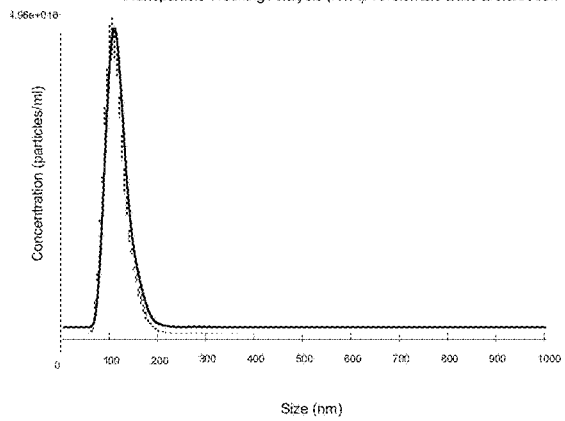
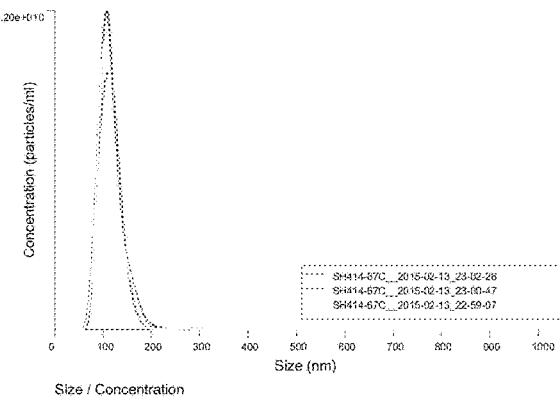

FTLA distribution – Average Size / Concentration Red
error bars indicate +/- 1 standard error of the mean

| | |
|---|---|
| Operator: | W.Bernt |
| Sample: | SH414-67C |
| Included files: | SH414-67C__2015-02-13_23-02-26 |
| | SH414-67C__2015-02-13_23-00-47 |
| | SH414-67C__2015-02-13_22-59-07 |
| Date/Time of Report | 13/02/2015  23:20:00 |
| Dispersant/Diluent: | H2O |
| Pretreatment | none |
| Remarks | dilution into DI H2O |

BATCH AVERAGE RESULTS:

| | |
|---|---|
| FTLA Size Distribution: | Mean: 114.0 +/- 0.4 nm |
| | Mode: 107 +/- 2.3 nm |
| | SD: 24.6 +/- 0.4 nm |
| | D10: 85 +/- 0.7 nm |
| | D50: 110.0 +/- 1.2 nm |
| | D90: 145 +/- 1.8 nm |
| Size Distribution: | Mean: 119 +/- 0.4 nm |
| | Mode: 105 +/- 2.0 nm |
| | SD: 39 +/- 0.5 nm |
| | D10: 73 +/- 0.0 nm |
| | D50: 113 +/- 0.3 nm |
| | D90: 167 +/- 1.3 nm |
| Dilution factor: | 2000 |
| Total Concentration: | 110.91 +/- 2.83 particles/frame |
| | 2.45e+012 +/- 6.25e+010 particles/ml |
| Total Completed Tracks: | 25818 |
| Average Drift Velocity: | 8075 nm/s |

CAPTURE SETTINGS

| | |
|---|---|
| Camera Type: | sCMOS |
| Shutter length: | Varied |
| Shutter setting: | 1000 |
| Camera gain: | 400 |
| Frame rate: | Varied |

ANALYSIS SETTINGS

| | |
|---|---|
| Background Extract: | On |
| Detection Threshold: | 2 - Multi |
| Blur: | AUTO |
| Min track length: | AUTO |
| Min expected size: | AUTO |
| Temperature: | 21.4, 21.4, 21.4 °C |
| Viscosity: | 0.97, 0.97, 0.97 cP |

WARNINGS

| Lane | Sample |
|------|--------|
| 1 | 1 Kb ladder |
| 2 | 5% AF not sheared |
| 3 | 5% AF sheared |
| 4 | 1.25% AF not sheared |
| 5 | 1.25% AF sheared |
| 6 | 0.625% AF not sheared |
| 7 | 0.625% AF sheared |
| 8 | 1.0% AF not sheared |
| 9 | 0.1% AF sheared |
| 10 | 0% AF not sheared |
| 11 | 0% AF sheared |

Figure 31
A
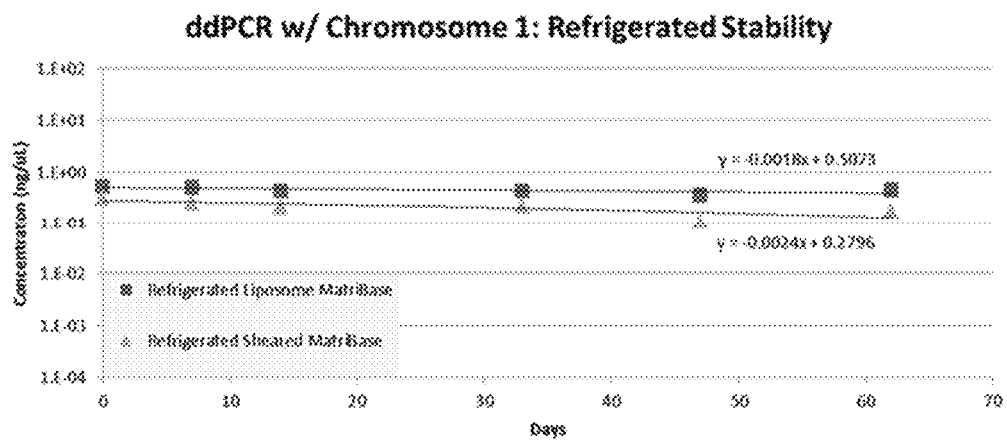
B
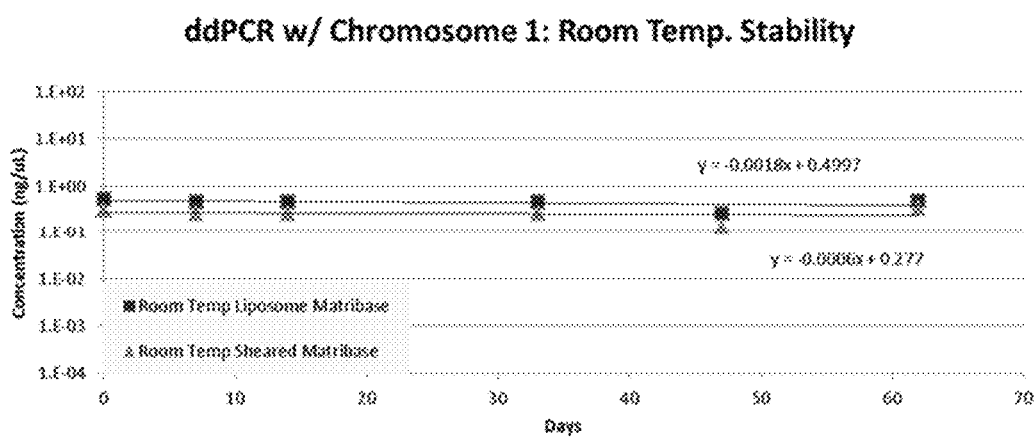
C
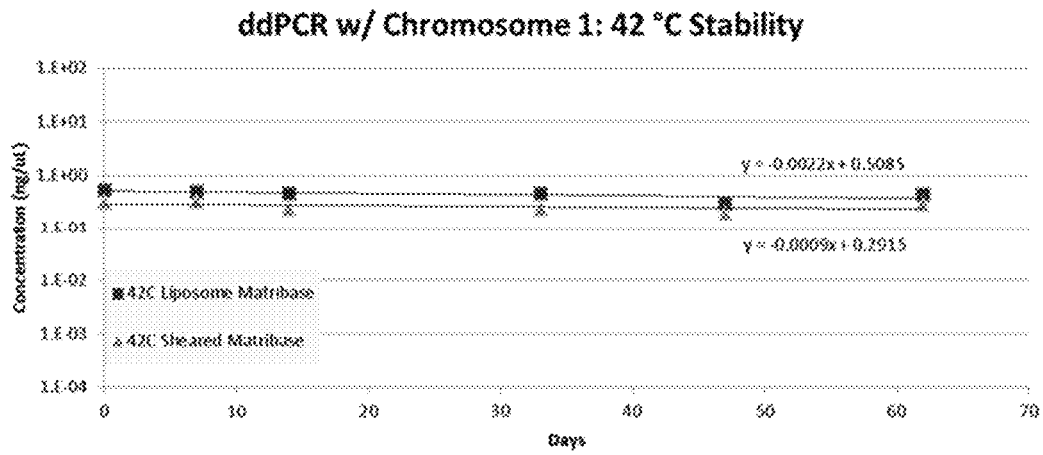

LIPOSOMAL PREPARATIONS FOR NON-INVASIVE-PRENATAL OR CANCER SCREENING

RELATED APPLICATIONS

This application is a US National Stage Application of PCT/US2016/031291, filed May 6, 2016, which claims the benefit of priority to U.S. Provisional Patent Application No. 62/157,729, filed May 6, 2015; U.S. Provisional Patent Application No. 62/171,672, filed Jun. 5, 2015; and U.S. Provisional Patent Application No. 62/254,898, filed Nov. 13, 2015.

BACKGROUND

Consistently accurate prenatal non-invasive aneuploidy screens for genetic disorders like Downs syndrome trisomy 21, Edwards syndrome trisomy 18, and Patau syndrome trisomy 13 are critically important to expectant mothers and their families. However, incorrect results have been reported for negative control samples. For example, Takoudes and Hamar reported results when a negative control, e.g., plasma sample from a non-pregnant female patient, was sent to 5 clinical testing labs for aneuploidy testing (Ultrasound Obstetrics Gynecology 45:112 (2015)). Two labs reported the correct results, not sufficient fetal DNA, two labs reported no aneuploidy normal XX, and one lab reported an aneuploidy normal fetus. The incorrect results suggest that the assay was not properly validated or that the assay was performed without proper run controls.

In order to evaluate whether an assay has been performed within specifications, controls are generally required. In clinical testing, controls are critical to reduce the risk of reporting incorrect results due to otherwise undetected assay failures. In prenatal testing, fetuses with chromosomal abnormalities are rare—even in "high risk" pregnant women—and they are becoming even rarer as more average- and low-risk women undergo noninvasive prenatal screening (NIPS). In NIPS testing, multiple samples are typically analyzed in parallel and, but even then, there is a high likelihood that none of the samples will contain fetal-derived cell free DNA ("cfDNA") with chromosomal abnormalities. By including a control that mimics cfDNA that contains fetal-derived cfDNA with one or more chromosomal abnormalities, it becomes possible to evaluate whether an assay is capable of detecting such abnormalities in the other samples that were analyzed. Accordingly, improved controls for cfDNA assays would improve the quality of diagnostic testing.

SUMMARY

In some aspects, the invention relates to a control for use in identifying a genotype, comprising liposomes and a first mixture of nucleic acids, wherein the first mixture of nucleic acids comprises a nucleotide sequence that encodes the genotype. At least about 90% of the nucleic acids of the control may be associated with the liposomes. The control may further comprise a second mixture of nucleic acids comprising a nucleotide sequence that encodes a second genotype, wherein the genotype and the second genotype are alternate genotypes that occur at the same genetic locus. The first mixture of nucleic acids and the second mixture of nucleic acids may be admixed in the control. The genotype may be associated with a disease, such as a neoplasm, a provirus, or a hereditary disease.

In some aspects, the invention relates to a control for use in identifying a plurality of genotypes, comprising liposomes and a first mixture of nucleic acids, wherein the first mixture of nucleic acids comprises a first plurality of nucleotide sequences, and each nucleotide sequence of the first plurality encodes a genotype of the plurality of genotypes. At least about 90% of the nucleic acids of the control may be associated with the liposomes. The control may further comprise a second mixture of nucleic acids, wherein the second mixture of nucleic acids comprises a second plurality of nucleotide sequences, and each nucleotide sequence of the second plurality is an alternate genotype that occurs at the same genetic locus as a nucleotide sequence of the first plurality. The first mixture of nucleic acids and the second mixture of nucleic acids may be admixed in the control.

In some aspects, the invention relates to a control for use in determining the ploidy of a chromosome in a fetus. The control may comprise a first mixture of nucleic acids comprising a first nucleotide sequence and a second nucleotide sequence, wherein the first nucleotide sequence has sequence homology with the chromosome; the second nucleotide sequence has sequence homology with a different chromosome; and the ratio of the copy number of the first nucleotide sequence to the copy number of the second nucleotide sequence is greater than 1:1. In some embodiments, the control may comprise a second mixture of nucleic acids comprising the first nucleotide sequence and the second nucleotide sequence, wherein the ratio of the copy number of the first nucleotide sequence to the copy number of the second nucleotide sequence is about 1:1. Similarly, in some embodiments, the control may comprise a second mixture of nucleic acids comprising a first nucleotide sequence and a second nucleotide sequence, wherein the ratio of the copy number of the first nucleotide sequence to the copy number of the second nucleotide sequence is about 1:1 in the second mixture; the first nucleotide sequence of the first mixture and the first nucleotide sequence of the second mixture consist of the same nucleotide sequence; and the second nucleotide sequence of the first mixture and the second nucleotide sequence of the second mixture consist of the same nucleotide sequence. The control may comprise liposomes, e.g., wherein at least about 90% of the nucleic acids in the control are associated with the liposomes. The chromosome may be, for example, human chromosome 8, 9, 13, 18, 21, 22, or X, which may display aneuploidy in a viable human fetus. The different chromosome may be, for example, human chromosome 1, 6, or 7, which are often used as reference chromosomes for determining the ploidy of a genome. The first mixture of nucleic acids and the second mixture of nucleic acids may be admixed in the control.

In some aspects, the invention relates to a control for use in determining the ploidy of a chromosome in a fetus. The control may comprise a first mixture of nucleic acids comprising a first plurality of nucleotide sequences and a second plurality of nucleotide sequences, wherein the first plurality of nucleotide sequences has sequence homology with the chromosome; the second plurality of nucleotide sequence has sequence homology with at least one autosome, wherein the at least one autosome does not comprise the chromosome; and the ratio of the copy number for any nucleotide sequence in the first plurality to the copy number for any nucleotide sequence in the second plurality is about 3:2. In some embodiments, the control may comprise a second mixture of nucleic acids comprising the first plurality of nucleotide sequences and the second plurality of nucleotide sequences, wherein the ratio of the copy number for any nucleotide sequence in the first plurality to the copy number for any nucleotide sequence in the second plurality is about 1:1. Similarly, in some embodiments, the control may comprise a second mixture of nucleic acids comprising a first plurality of nucleotide sequences and a second plurality of nucleotide sequences, wherein the ratio of the copy number for any nucleotide sequence in the first plurality to the copy number for any nucleotide sequence in the second plurality is about 1:1 in the second mixture; the first plurality of nucleotide sequences of the first mixture and the first plurality of nucleotide sequences of the second mixture consist of the same nucleotide sequences; and the second plurality of nucleotide sequences of the first mixture and the second plurality of nucleotide sequences of the second mixture consist of the same nucleotide sequences. The first mixture of nucleic acids and the second mixture of nucleic acids may be admixed in the control. The control may comprise liposomes, e.g., wherein at least about 90% of the nucleic acids in the control are associated with the liposomes.

In some aspects, the invention relates to a control for use in determining the ploidy of the sex chromosomes in a fetus. The control may comprise a first mixture of nucleic acids comprising a first nucleotide sequence and a second nucleotide sequence, wherein the first nucleotide sequence has sequence homology with chromosome Y; the second nucleotide sequence has sequence homology with an autosome; and the ratio of the copy number of the first nucleotide sequence to the copy number of the second nucleotide sequence is about 1:1. The control may comprise a second mixture of nucleic acids, wherein the second mixture of nucleic acids does not comprise a nucleotide sequence that has sequence homology with chromosome Y. The first mixture of nucleic acids and the second mixture of nucleic acids may be admixed in the control. The control may comprise liposomes, e.g., wherein at least about 90% of the nucleic acids in the control are associated with the liposomes.

In some aspects, the invention relates to a control for use in determining the ploidy of the sex chromosomes in a fetus. The control may comprise a first mixture of nucleic acids comprising a first nucleotide sequence, a second nucleotide sequence, and a third nucleotide sequence, wherein the first nucleotide sequence has sequence homology with chromosome X; the second nucleotide sequence has sequence homology with an autosome; a third nucleotide sequence has sequence homology with chromosome Y; and the ratio of the copy numbers of the first, second, and third nucleotide sequences is about 2:2:1. In some embodiments, the control may comprise a second mixture of nucleic acids comprising the first nucleotide sequence and the second nucleotide sequence, wherein the ratio of the copy numbers of the first and second nucleotide sequences is about 1:1; and the second mixture of nucleic acids does not comprise a nucleotide sequence that has sequence homology with chromosome Y. Similarly, in some embodiments, the control may comprise a second mixture of nucleic acids comprising a first nucleotide sequence and a second nucleotide sequence, wherein the ratio of the copy numbers of the first and second nucleotide sequences is about 1:1 in the second mixture; the first nucleotide sequence of the first mixture and the first nucleotide sequence of the second mixture consist of the same nucleotide sequence; the second nucleotide sequence of the first mixture and the second nucleotide sequence of the second mixture consist of the same nucleotide sequence; and the second mixture of nucleic acids does not comprise a nucleotide sequence that has sequence homology with chromosome Y. The control may comprise liposomes, e.g., wherein at least about 90% of the nucleic acids in the control are associated with the liposomes. The first mixture of nucleic acids and the second mixture of nucleic acids may be admixed in the control.

In some aspects, the invention relates to a control for use in determining the sex of a fetus. The control may comprise a first mixture of nucleic acids comprising a nucleotide sequence that has sequence homology with human chromosome Y. The control may comprise a second mixture of nucleic acids that does not comprise a nucleotide sequence that has sequence homology with human chromosome Y. The control may comprise liposomes, e.g., wherein at least about 90% of the nucleic acids in the control are associated with the liposomes.

In some aspects, the invention relates to a control for use in identifying or characterizing a disease or condition, comprising liposomes and a first mixture of nucleic acids, wherein the first mixture of nucleic acids comprises a nucleotide sequence of a microRNA ("miRNA" or "miR"). At least about 90% of the nucleic acids of the control may be associated with the liposomes.

In some aspects, the invention relates to a control for use in identifying or characterizing a disease or condition, comprising liposomes and a first mixture of nucleic acids, wherein the first mixture of nucleic acids comprises a plurality of microRNA nucleotide sequences. At least about 90% of the nucleic acids of the control may be associated with the liposomes.

In some aspects, the invention relates to a method for validating a diagnostic test for analysis of circulating cell-free DNA, comprising performing the diagnostic test on a control as described herein, wherein the diagnostic test is validated if it correctly identifies the genotype of the control.

In some aspects, the invention relates to a method for determining whether a sample comprises a genotype, comprising performing a diagnostic test on the sample and performing the diagnostic test on a control as described herein, wherein the control comprises the genotype. In some embodiments, the sample is found to comprise the genotype if the diagnostic test indicates that both the sample and the control comprise the genotype; the sample is found to not comprise the genotype if the diagnostic test indicates that the sample does not comprise the genotype but that the control comprises the genotype; and the diagnostic test is found to be inconclusive if the test indicates that the control does not comprise the genotype.

loaded into DMPC liposomes and extruded through a 100 nm polycarbonate extrusion disk, as well as "ghost" liposomes, which do not contain DNA, and an aliquot of sheared DNA, which was not incorporated into a liposome. The liposomes do not interact with the stationary phase whereas naked DNA binds to the stationary phase and elutes with increasing salt concentration.

FIG. 6 is a NTA Report, which measure particle size, polydispersity, and concentration. Data are representative of DNA loaded DMPC liposomes and extruded through 100 nm polycarbonate extrusion disk.

Figure 7:
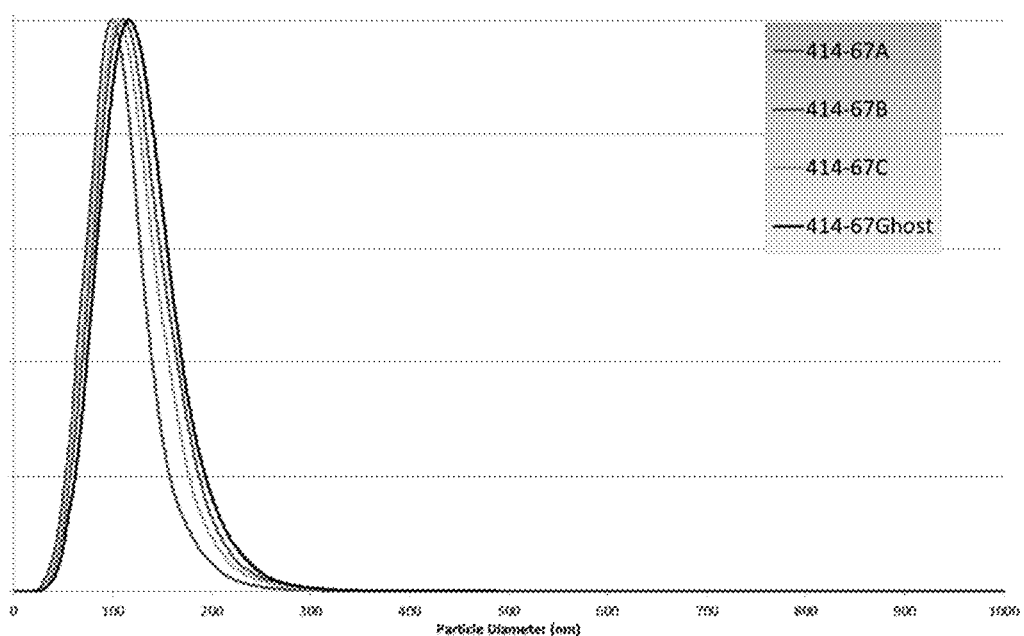

FIG. 7 is a graph that shows size distribution for three preparations of DNA loaded DMPC liposomes extruded through a 100 nm polycarbonate extrusion disk as well as a corresponding "ghost" liposome, which does not contain DNA.

Figure 8:
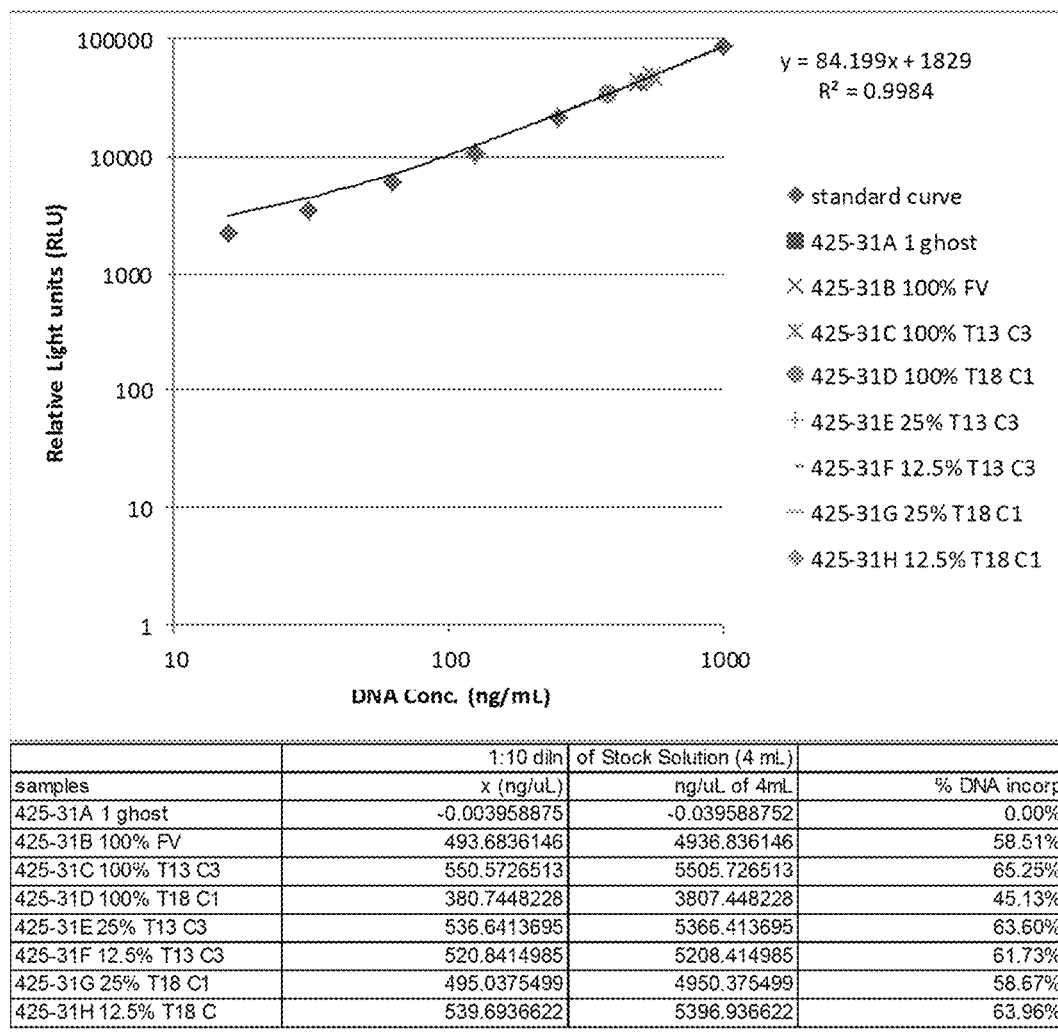

FIG. 8 depicts the DNA concentrations by PicoGreen analysis of seven preparations of DNA-loaded DMPC/2.5% DDAB liposomes extruded through a 200 nm polycarbonate extrusion disk, as well as a standard curve, which was prepared using a serial dilution of DNA sheared to about 170 base pairs. The LipoDNA concentration and incorporation rates are also shown.

Figure 9:
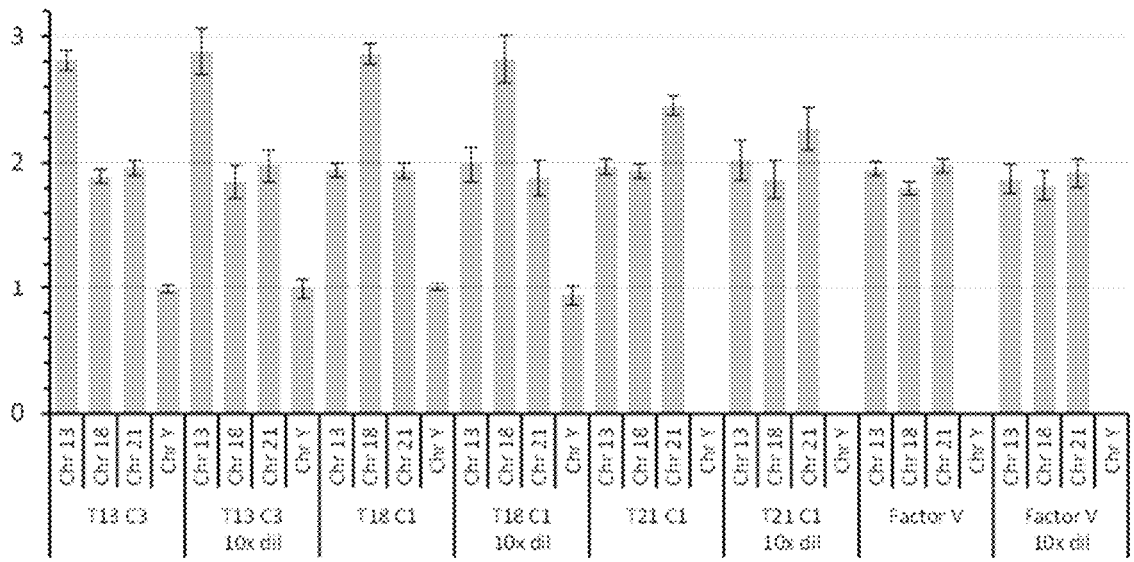

FIG. 9 is a graph of the copy number for chromosomes in various samples as determined by ddPCR (Bio-Rad QX200™ Droplet Reader). Each sample comprised purified genomic DNA, which had been digested with a cocktail of restriction enzymes, obtained from the indicated cell lines.

Figure 10:
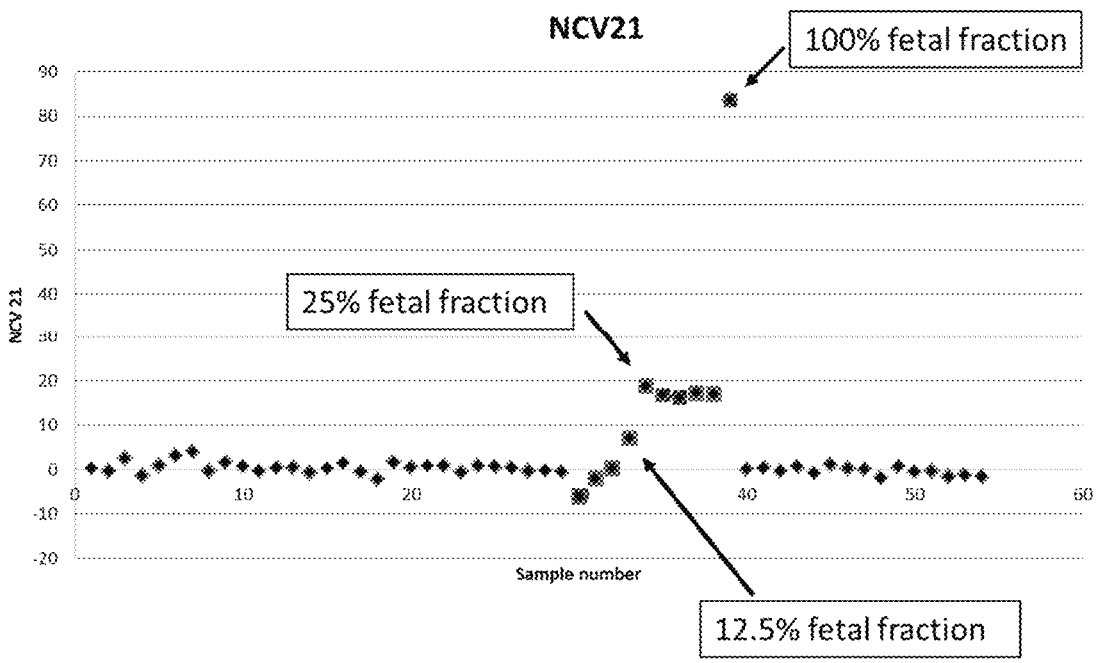

FIG. 10 is a graph of the Normalized Chromosome Values for samples comprising various concentrations of aneuploid DNA (i.e., trisomy 21 DNA).

Figure 11:
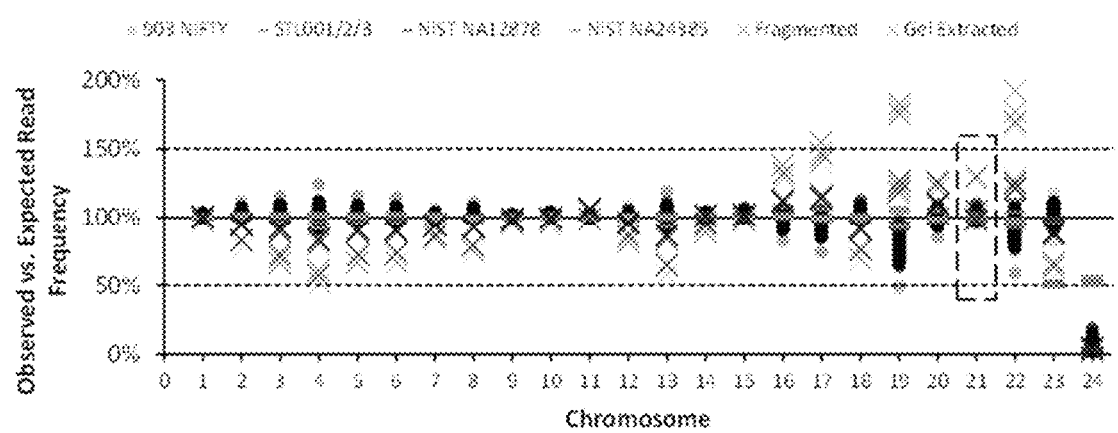

FIG. 11 is a graph that depicts the observed versus expected read frequency for individual chromosomes. Gel extracted nucleic acids, which have a higher GC content than other samples, displayed observed frequencies that varied considerably from expected values and from other samples.

Figure 12:
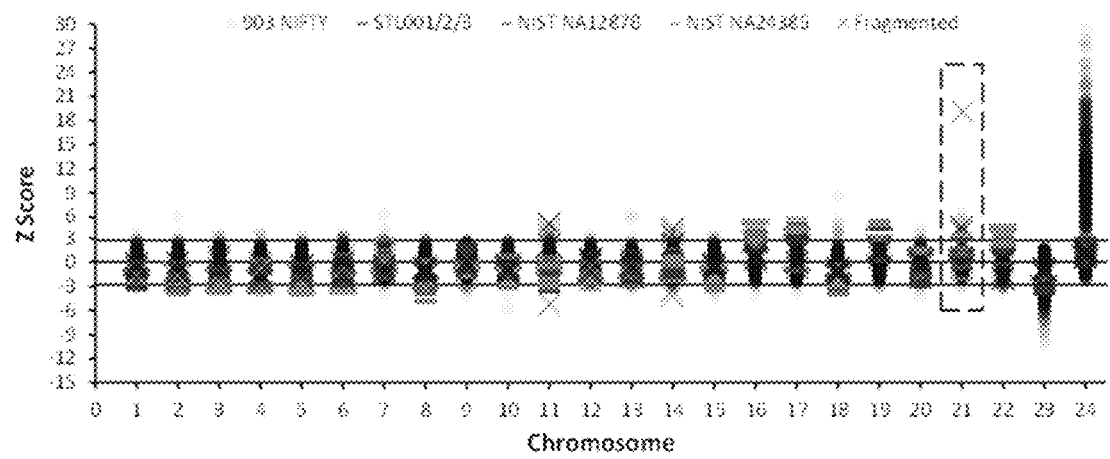

FIG. 12 is a graph that depicts the z-scores for the number of times a chromosome is calculated in a sample relative to other chromosomes in the sample. The fragmented sample comprises trisomy 21 DNA.

Figure 13:
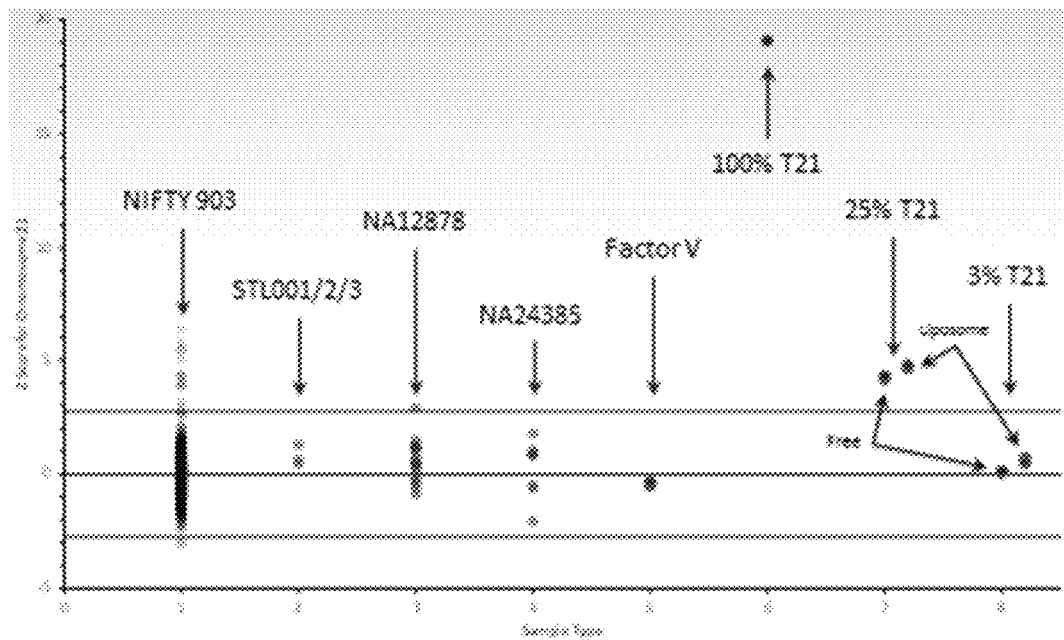

FIG. 13 is a graph that depicts the z-scores for the number of times chromosome 21 is calculated to occur in a sample relative to other chromosomes in the sample. NIFTY 903 (903 patient samples), STL001/2/3, NA12878, and NA24385 are data points from publically available sequences. The "Factor V" sample is the source of "maternal DNA". The "100% T21" sample comprises genomic DNA with trisomy 21. The "25% T21" and "3% T21" samples comprise mixtures of 100% T21 DNA and Factor V DNA. Liposome encapsulation resulted in no noticeable effect on detecting chromosome 21 aneuploidy.

Figure 14:
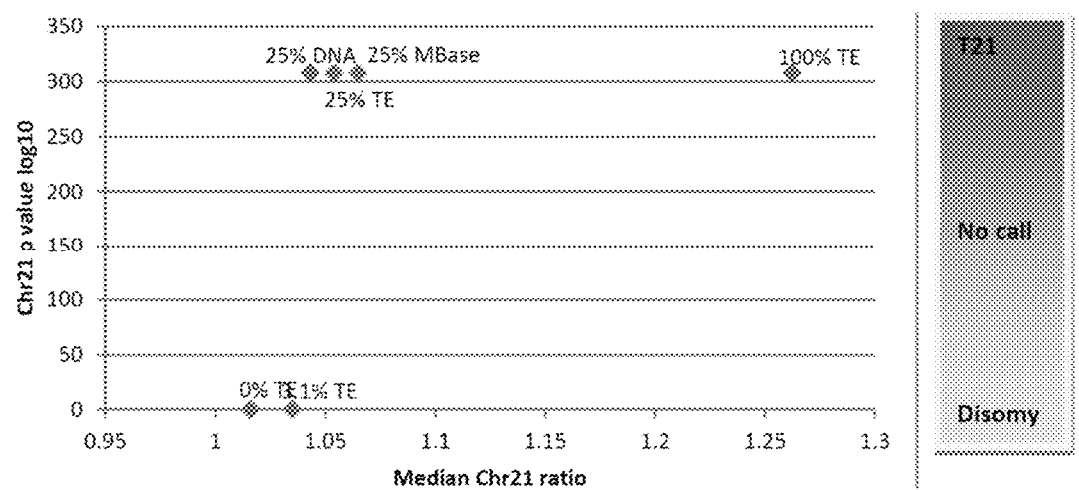

FIG. 14 is a graph depicting the use of various controls of the invention in a microarray assay used to detect trisomy 21.

Figure 15:
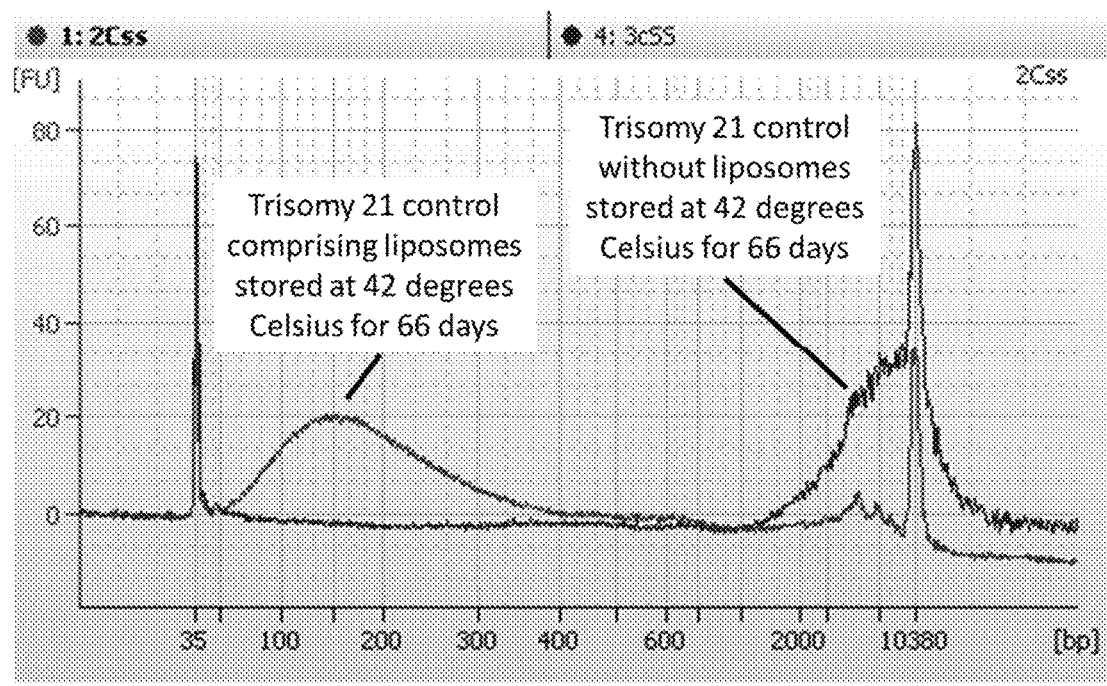

FIG. 15 is a Bioanalyzer trace depicting the relative abundance of DNA at observed sizes in two samples after storage for 66 days at 42° C. (Example 12). The trace suggests that a trisomy 21 control without liposomes aggregated whereas a trisomy 21 control comprising liposomes displayed substantially no aggregation.

Figure 16:
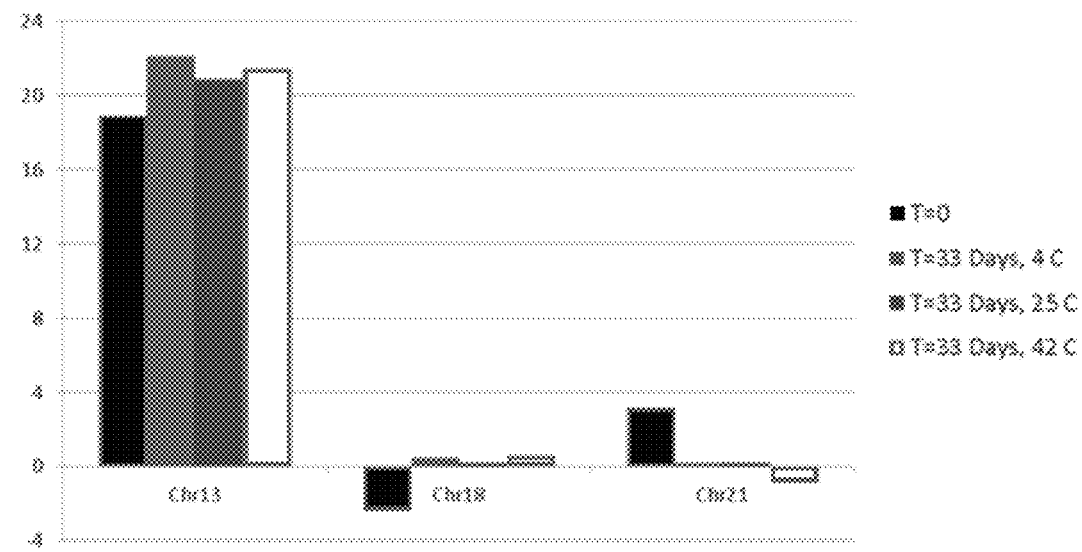

FIG. 16 is a graph of NCV for chromosomes 13, 18, and 21 obtained by next generation sequencing for samples comprising liposomes that were stored at various temperatures. The graph shows that chromosome 13 displayed polyploidy, but chromosomes 18 and 21 did not.

Figure 17:
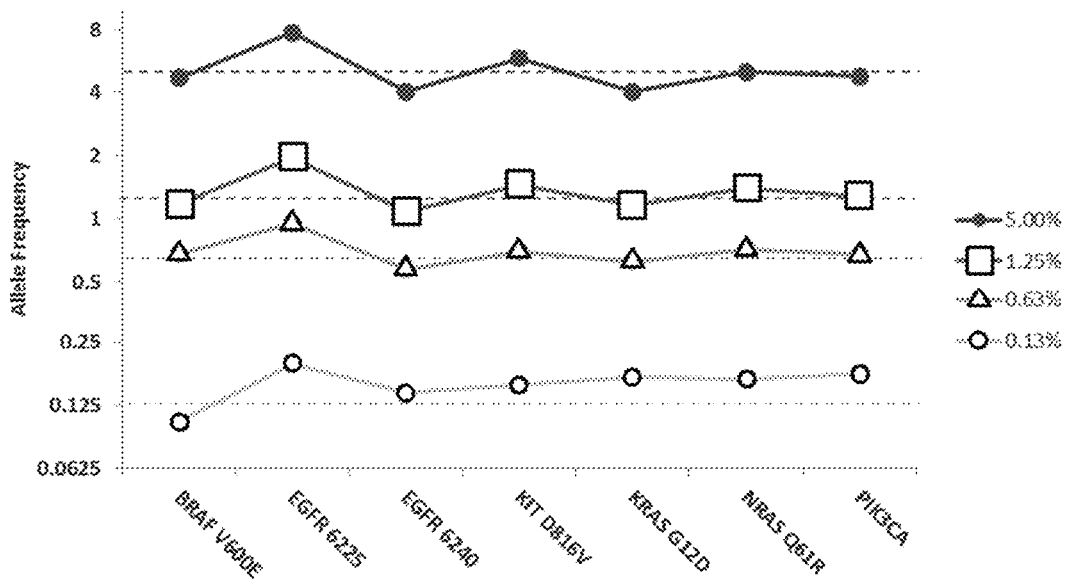

FIG. 17 is a graph of the calculated allelic frequency for controls containing nine genotypes (seven are included in the assay) associated with neoplasms and genomic DNA at a genotype-to-genomic DNA concentration of 0.13%, 0.63%, 1.25%, and 5.0%. These controls do not comprise liposomes.

Figure 18:
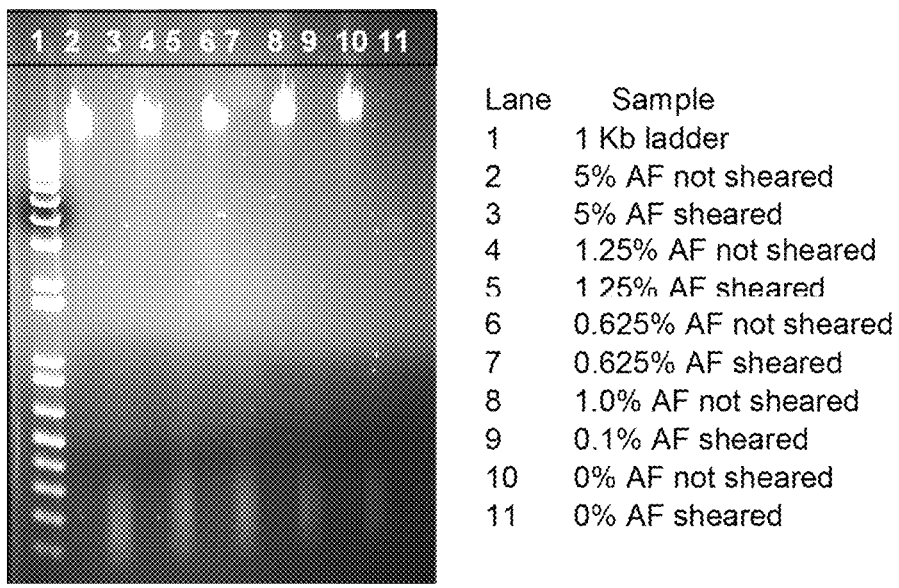

FIG. 18 is an image of a 1% agarose gel showing control DNA before ("not sheared") and after ("sheared") shearing the DNA.

Figure 19:
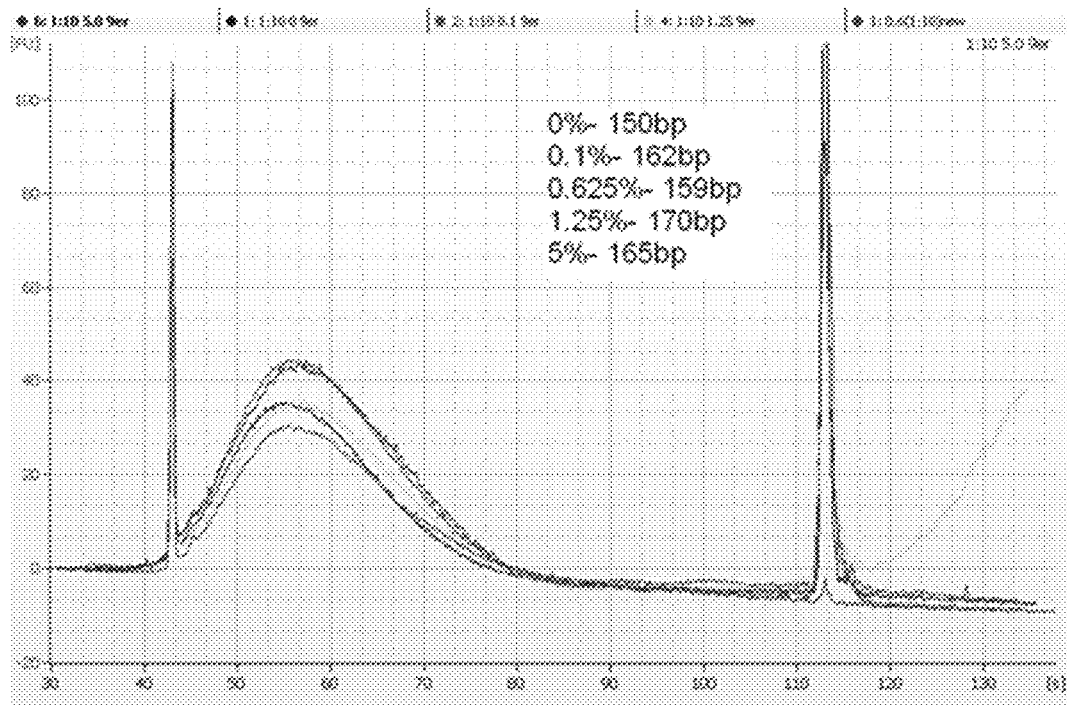

FIG. 19 is a Bioanalyzer trace confirming that control DNA was sheared to sizes ranging from 150 base pairs to 170 base pairs.

Figure 20:
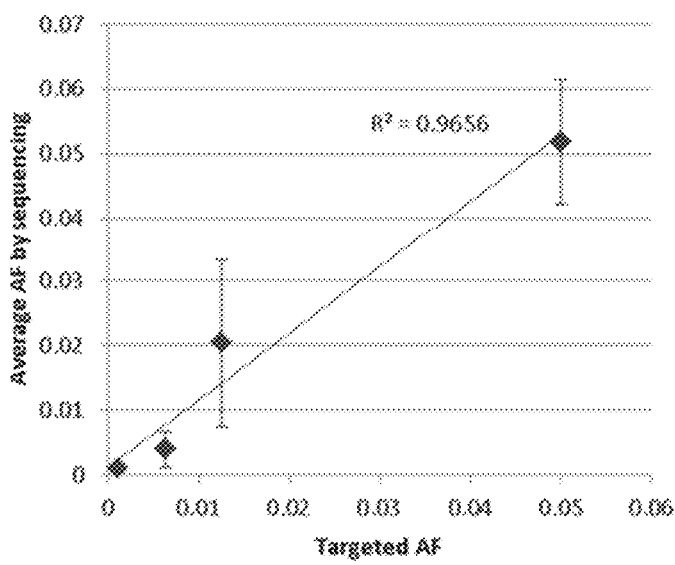

FIG. 20 is a graph of the actual allelic frequency ("Targeted AF") versus observed allelic frequency ("Average AF by sequencing") for four controls containing 0.1%, 0.63%, 1.25%, or 5% mutant DNA relative to total DNA. The total DNA consisted of the mutant DNA and genomic DNA. The mutant DNA consisted of portions of 9 genes and each sequence comprised a mutation that is associated with cancer. The "Average AF by sequencing" values are the average of the allelic frequencies of the 9 genes identified during a single NGS analysis of each of the four controls.

Figure 21:
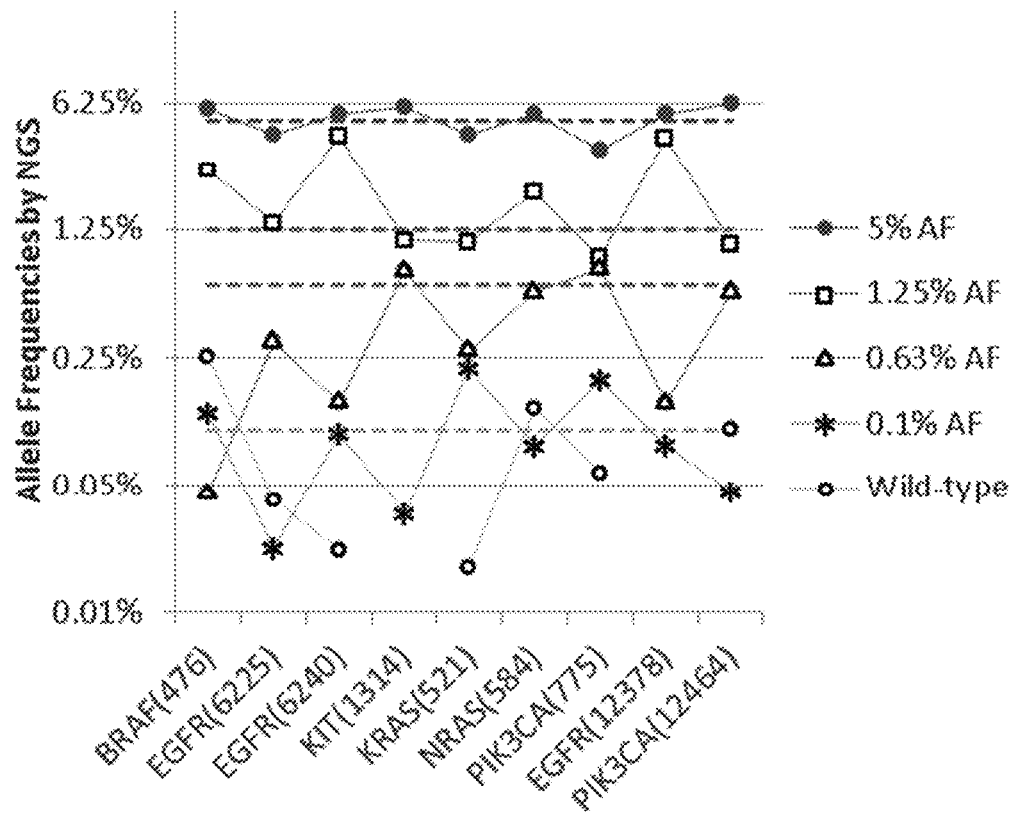

FIG. 21 is a graph of the calculated allelic frequency (y-axis) obtained by next generation sequencing of the nine different mutations (x-axis) in control samples, wherein the control samples comprise an allelic frequency of a mutant genotype relative to genomic DNA of 5%, 1.25%, 0.63%, 0.1%, or 0%.

Figure 22:
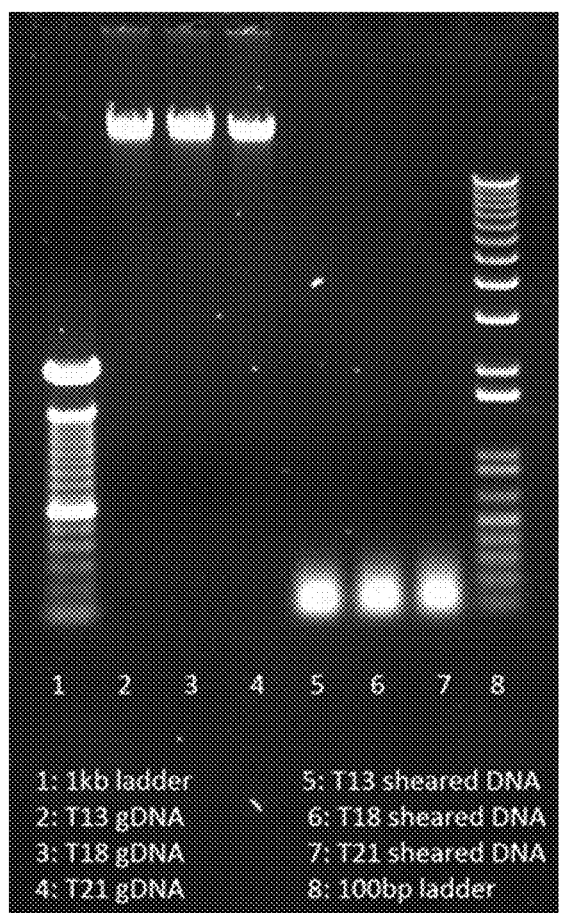

FIG. 22 is an image of a 0.6% agarose gel depicting genomic DNA from aneuploid cell lines before and after shearing.

Figure 23:
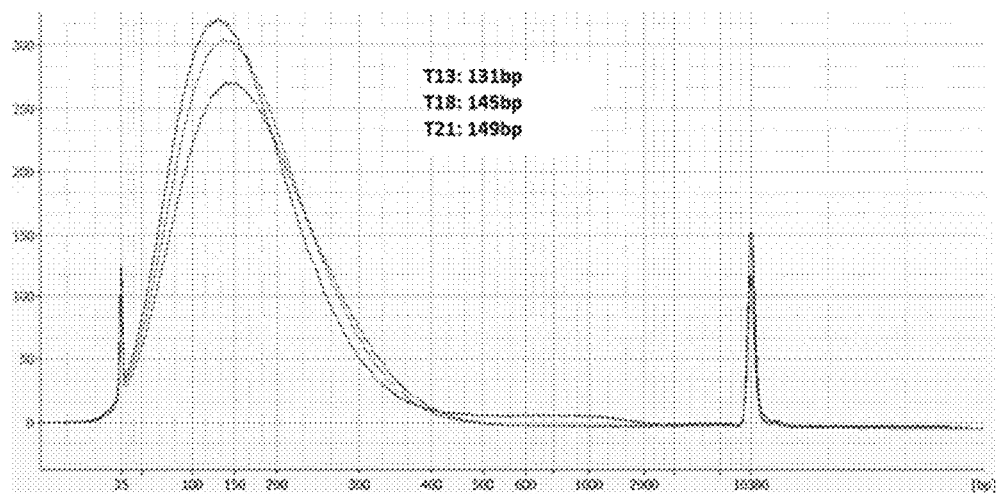

FIG. 23 is a Bioanalyzer trace for controls comprising trisomy 13 (T13), trisomy 18 (T18), or trisomy 21 (T21) DNA. The trace shows that the peak maximum of the nucleic acids in the trisomy 13 control is 131 base pairs, the peak maximum in the trisomy 18 control is 145 base pairs, and the peak maximum in the trisomy 21 control is 149 base pairs.

Figure 24:
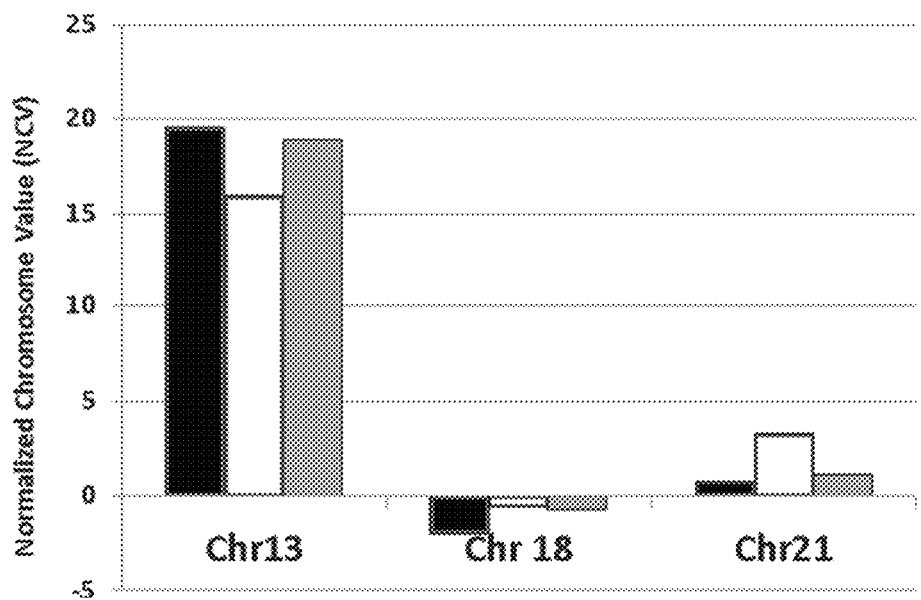

FIG. 24 is a bar graph depicting the measured normalized chromosome value (NCV) for chromosomes 13, 18, and 21 in three aliquots of a trisomy 13 control.

Figure 25:
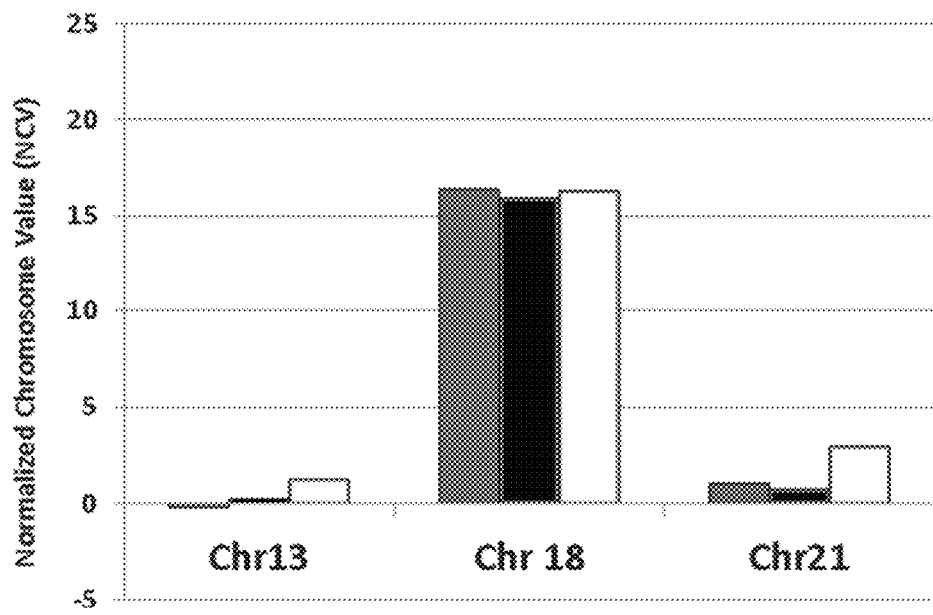

FIG. 25 is a bar graph depicting the measured normalized chromosome value (NCV) for chromosomes 13, 18, and 21 in three aliquots of a trisomy 18 control.

Figure 26:
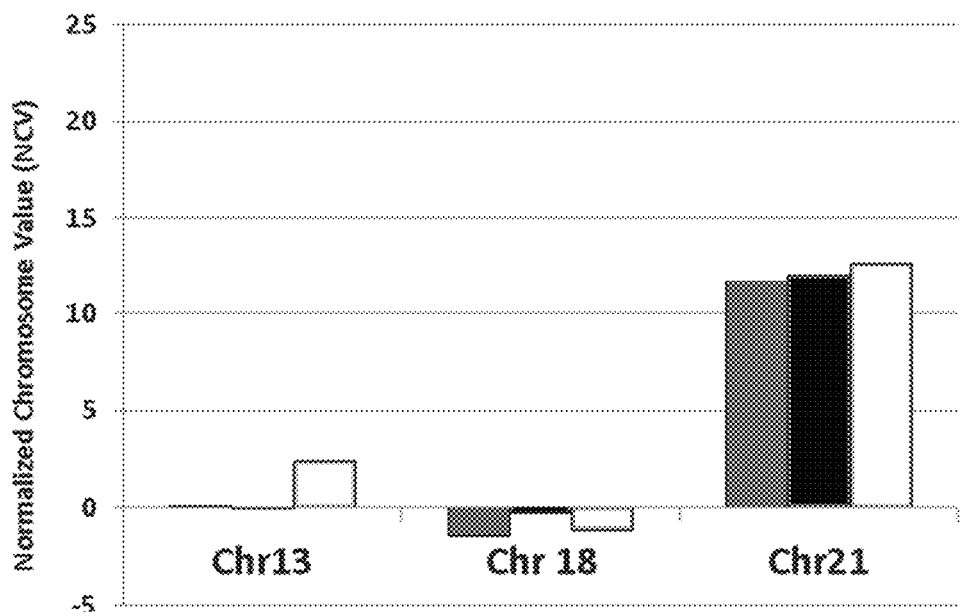

FIG. 26 is a bar graph depicting the measured normalized chromosome value (NCV) for chromosomes 13, 18, and 21 in three aliquots of a trisomy 21 control.

Figure 27:
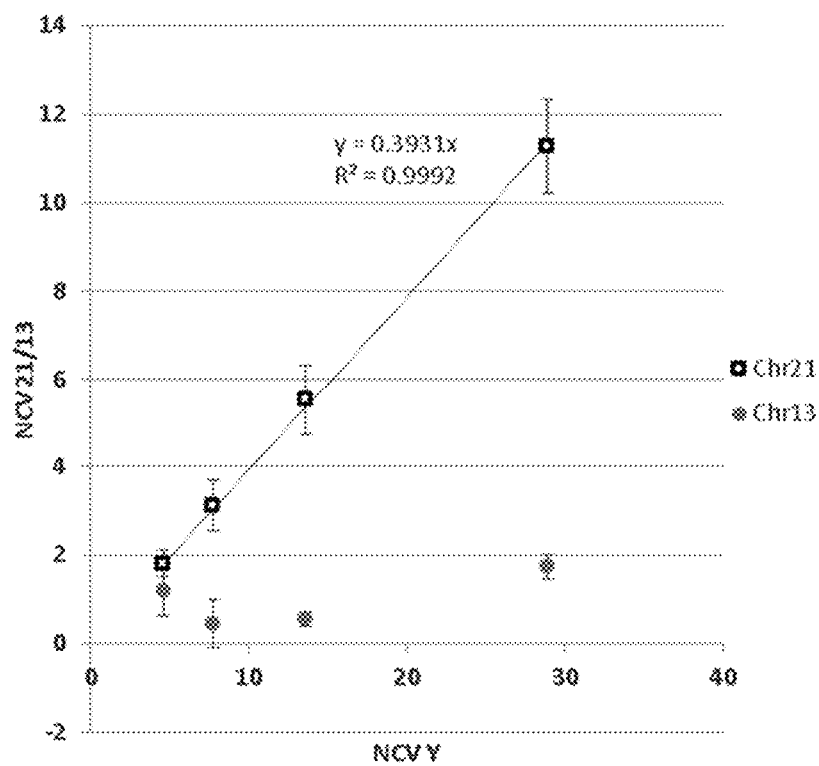

FIG. 27 is a graph depicting the measured normalized chromosome value (NCV) of chromosomes 21 and 13 in controls comprising 1%, 2%, 4%, or 8% trisomy 21 DNA versus the measured NCV of chromosome Y (x axis). The trisomy 21 genomic DNA comprises a Y chromosome and all other genomic DNA (simulated "maternal" DNA) does not comprise a Y chromosome.

Figure 28:
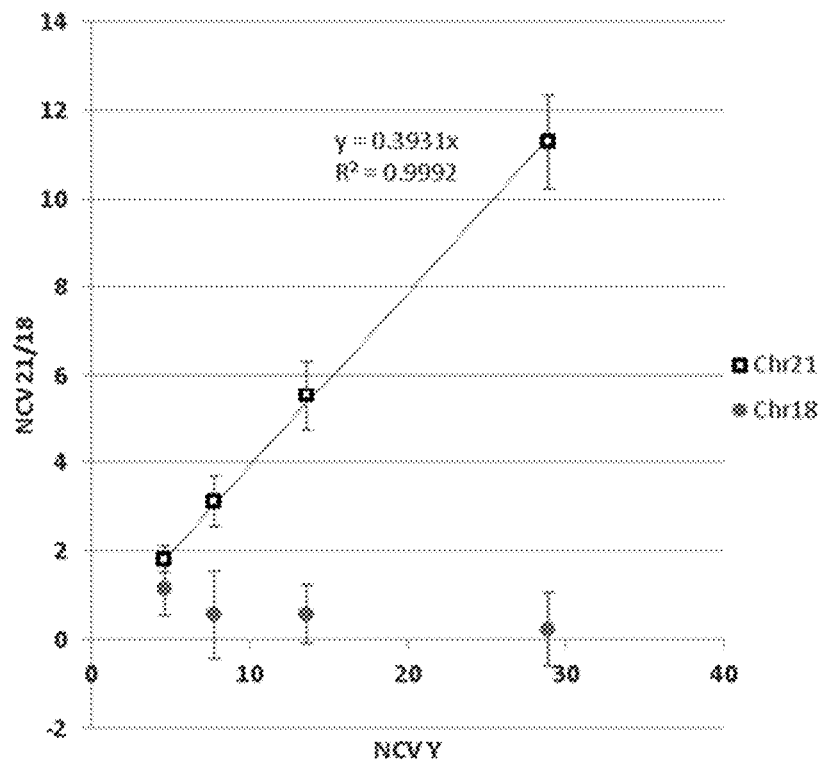

FIG. 28 is a graph depicting the measured normalized chromosome value (NCV) of chromosomes 21 and 18 in controls comprising 1%, 2%, 4%, or 8% trisomy 21 DNA versus the measured NCV of chromosome Y (x axis). The trisomy 21 genomic DNA comprises a Y chromosome and all other genomic DNA (simulated "maternal" DNA) does not comprise a Y chromosome.

Figure 29:
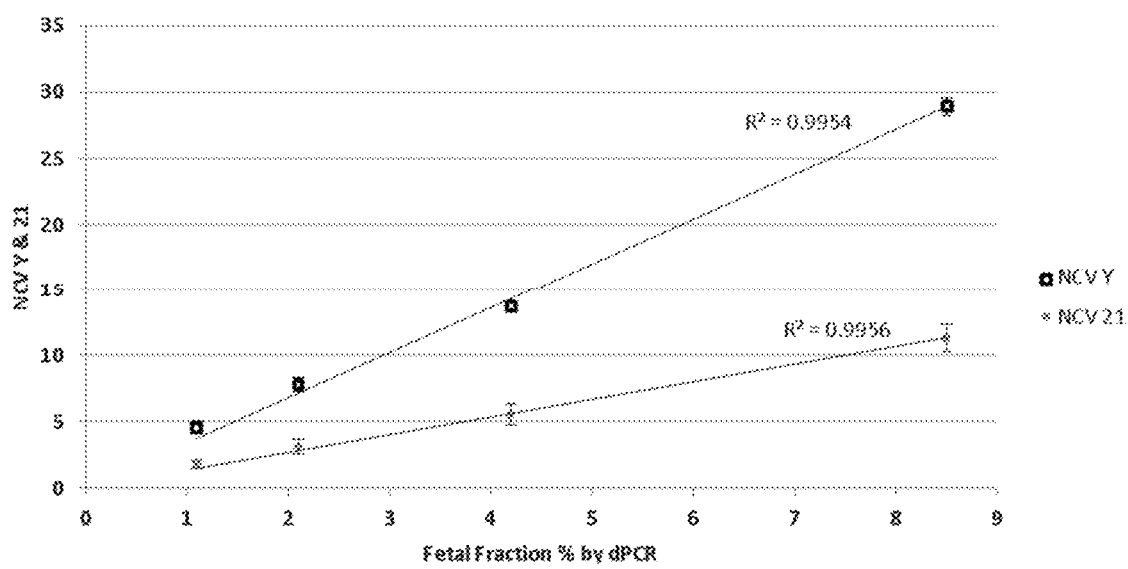

FIG. 29 is a graph depicting the measured normalized chromosome value (NCV) of chromosomes 21 and Y in controls comprising 1%, 2%, 4%, or 8% trisomy 21 DNA versus the measured concentration of trisomy 21 genomic DNA ("Fetal Fraction % by dPCR"; x axis). The trisomy 21 genomic DNA comprises a Y chromosome and all other genomic DNA (simulated "maternal" DNA) does not comprise a Y chromosome.

Figure 30:
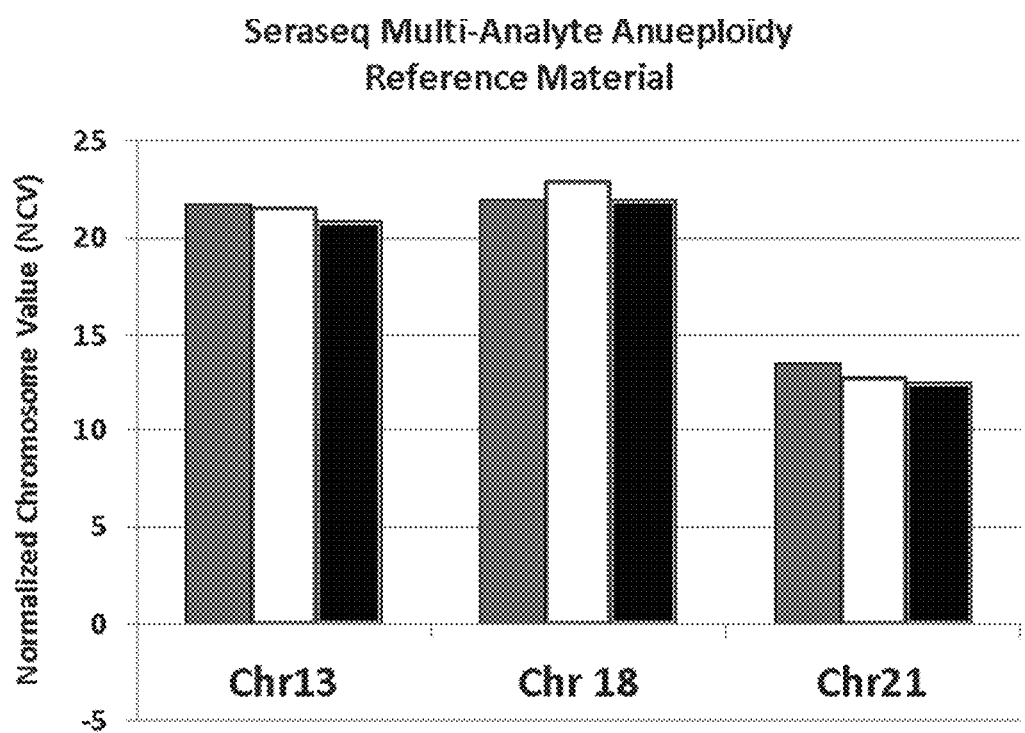

FIG. 30 is a bar graph depicting the measured normalized chromosome value (NCV) for chromosomes 13, 18, and 21 in three aliquots of a multi-analyte trisomy control, comprising 12% trisomy 13 genomic DNA, 12% trisomy 18 genomic DNA, and 12% trisomy 21 genomic DNA.

FIG. 31 consists of three panels, labeled panels (A), (B), and (C). Each panel is a graph depicting the stability of trisomy 21 controls comprising liposomes or no liposomes as assessed by digital PCR. The controls were stored at 2-8° C. ("Refrigerated Stability; panel (A)), 22° C. ("Room Temp. Stability; panel (B)), or 42° C. ("42° C. Stability; panel (A)). Digital PCR did not detect a difference between controls comprising liposomes and controls that do not comprise liposomes. Digital PCR also did not detect an effect of temperature on stability.

Figure 32:
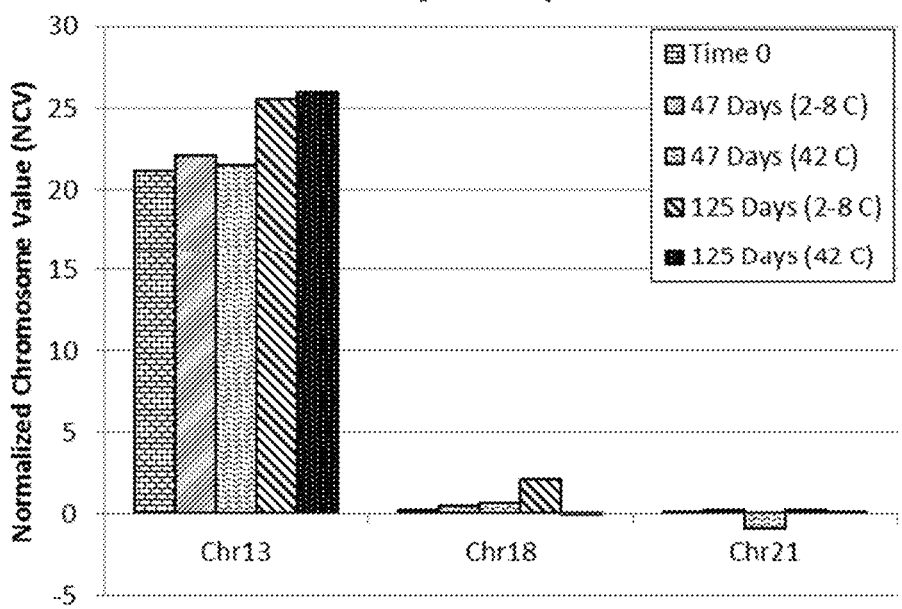

FIG. 32 is a graph showing the normalized chromosome values (NCV) of chromosomes 13, 18, and 21 for trisomy 21 controls comprising liposomes as measured by next-generation sequencing on an Illumina HiSeq platform either immediately after manufacture (Time 0), after storage for 47 or 125 days at 2-8° C., or after storage for 47 or 125 days at 42° C.

Figure 33:
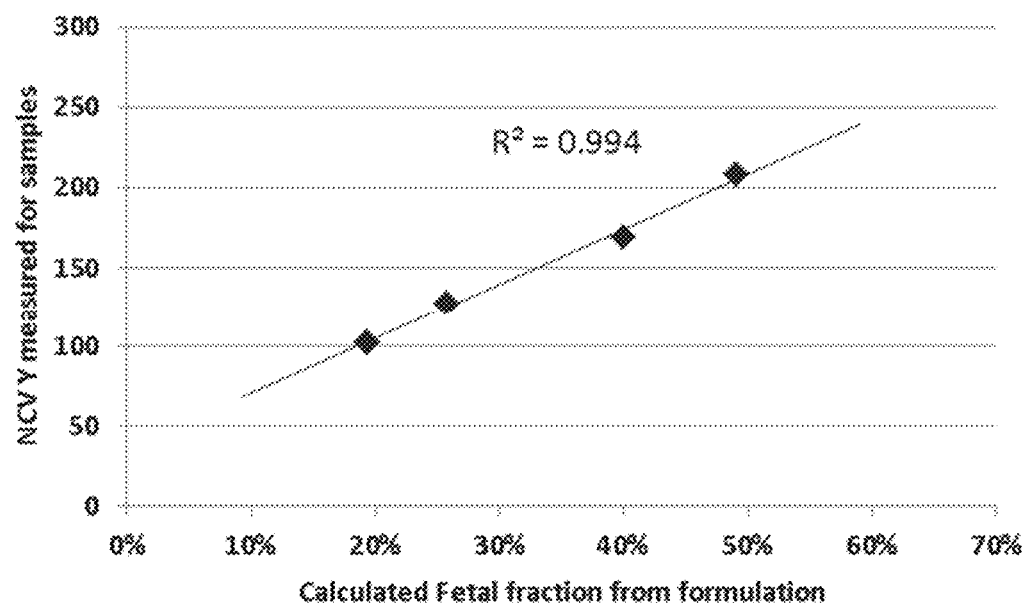

FIG. 33 is a graph of the calculated percentage of trisomy DNA in samples comprising either male trisomy 13 or male trisomy 18 DNA and female circulating cell-free DNA (x-axis) against measured normalized chromosome value (NCV; y-axis).

Figure 34:
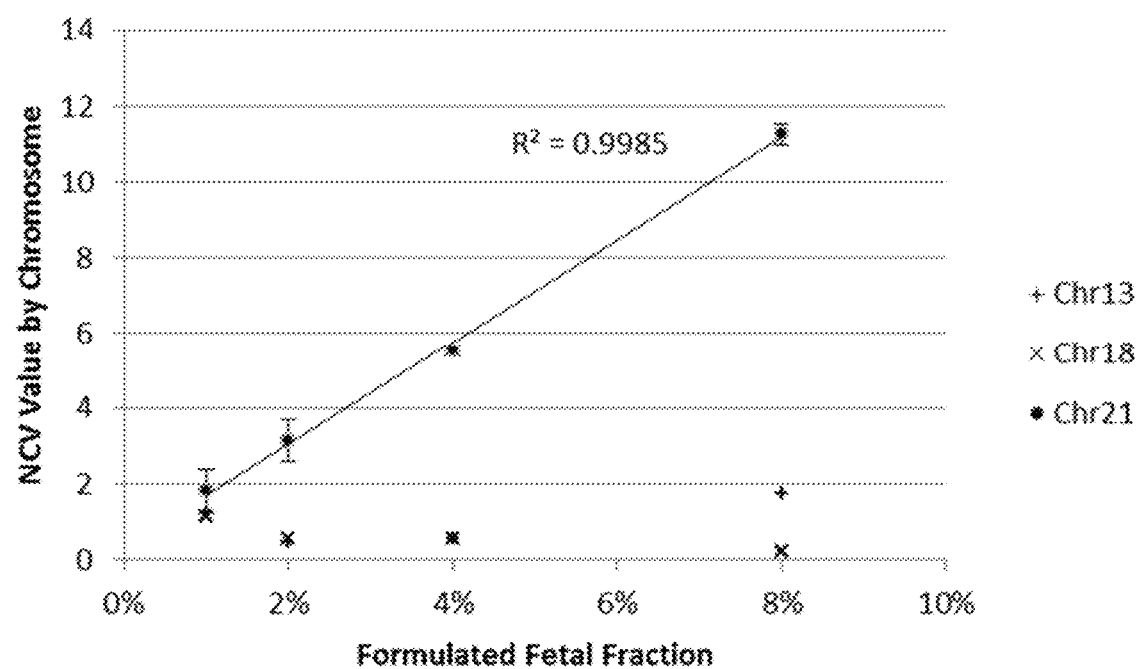

FIG. 34 is a graph of the percentage of trisomy DNA in samples comprising trisomy 21 DNA and female circulating cell-free DNA (x-axis) against measured normalized chromosome value (NCV) for chromosomes 13, 18, and 21 (y-axis).

Figure 35:
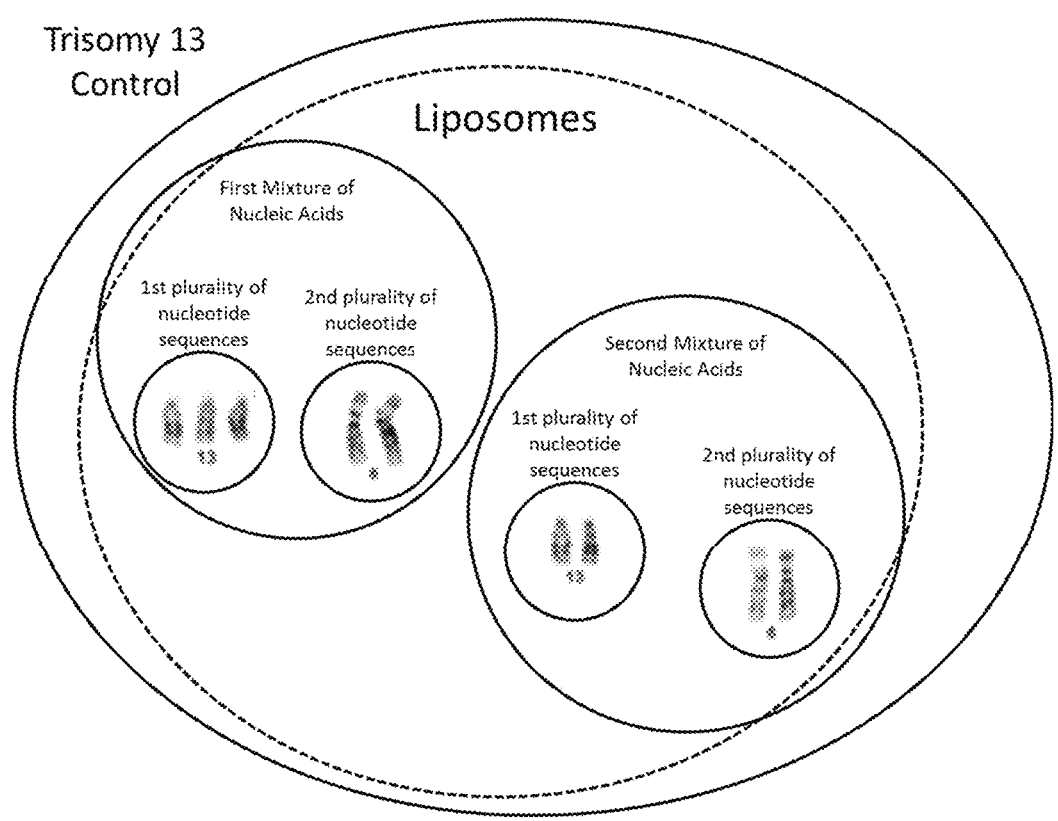

FIG. 35 is a diagram of a trisomy 13 control. The control comprises liposomes (dotted line) and nucleic acids associated with the liposomes. The nucleic acids include a first mixture of nucleic acids and a second mixture of nucleic acids. The first mixture of nucleic acids may encode substantially all of a trisomy 13 human genome, such as a human cytotrophoblast genome. The second mixture of nucleic acids may encode substantially all of a euploid human genome, such as a female peripheral blood mononuclear cell (PBMC) genome. The first mixture of nucleic acids may comprise a first plurality of nucleotide sequences, wherein each nucleotide sequence of the first plurality has sequence homology to chromosome 13 (or chromosome 18 or chromosome 21). The first plurality of nucleotide sequences may or may not encode substantially all of chromosome 13. The first mixture of nucleic acids may comprise a second plurality of nucleotide sequences, wherein each nucleotide sequence of the second plurality has sequence homology to at least one autosome that does not comprise chromosome 13, such as chromosome 6. The second plurality of nucleotide sequences may or may not encode substantially all of the at least one autosome; for example, the second plurality of nucleotide sequences may encode substantially all of chromosomes 1, 6, and/or 7. The ratio of the copy number for any nucleotide sequence in the first plurality to the copy number for any nucleotide sequence in the second plurality is about 3:2 in the first mixture of nucleic acids, i.e., because a human trisomy 13 genome comprises 3 copies of chromosome 13 and 2 copies of every other autosome. The second mixture of nucleic acids may comprise the first plurality of nucleotide sequences, i.e., that have sequence homology to chromosome 13, and the second plurality of nucleotide sequences. The ratio of the copy number for any nucleotide sequence in the first plurality to the copy number for any nucleotide sequence in the second plurality is about 1:1 in the second mixture of nucleic acids, i.e., because a euploid human genome comprises 2 copies of every autosome. The composition may comprise nucleic acids at a concentration of about 1 ng/mL to about 100 ng/mL. Approximately 2% to 32% of the nucleic acids of the control may be nucleic acids of the first mixture and approximately 68% to 98% of the nucleic acids of the control may be nucleic acids of the second mixture.

DETAILED DESCRIPTION

Overview

In some aspects, the invention described herein is a broadly applicable methodology for creating whole process, commutable, and patient-like controls for in vitro screening, testing, and/or diagnostics utilizing circulating cell free DNA (cfDNA) as a biomarker of interest. cfDNA is a direct marker from normal or diseased cells, and thus, it is an ideal biomarker for fetal genetic analysis and for identifying metastatic tumors. In this context, cfDNA is defined as DNA found in circulating blood, which is extracellular and may be associated with apoptotic bodies, nucleosomes, extracellular vesicles, or in another extracellular form. Characteristically, cfDNA is truncated in size, e.g., as a result of enzymatic cleavage in vivo, which typically results in fragments that are 150-200 base pairs in length. Further, cfDNA is scarce in blood, with typical concentrations of 5-50 ng/mL. Applications for cfDNA analysis are expanding and include non-invasive prenatal screening/testing (NIPS/NIPT) and the analysis of circulating tumor DNA as it relates to cancer diagnostics and therapies.

Definitions

The term "copy number", as used herein, refers to the number of times a nucleotide sequence occurs in a composition, such as a control or a mixture of nucleic acids. A nucleotide sequence may occur as a subsequence on different nucleic acids. For example, ten copies of a 35 base pair nucleotide sequence may occur in ten different nucleic acids in a mixture of nucleic acids, e.g., wherein each of the ten different nucleic acids have different lengths. Similarly, the term "copy number" may refer to the concentration of a nucleotide sequence, e.g., per unit volume. For example, ten copies of a 35 base pair nucleotide sequence may occur, on average, per every microliter of volume.

The term "control" may refer to a control sample, process control, run control, positive control, negative control, validation sample, proficiency sample, reference material, standard, or analytical standard. A control may be a positive control, e.g., for monitoring the performance of a diagnostic test, such as sensitivity, accuracy, and/or precision. A control may be an analytical standard, e.g., for calibrating a diagnostic test or for assessing its sensitivity. A control may be a process control, e.g., for monitoring the sensitivity, accuracy, and/or precision of a diagnostic test during a single test or to assess trends over time (e.g., drift). A process control may be used to monitor an entire process from sample preparation to data analysis or any step in between. A control may be a run control, such as a control sample, e.g., for monitoring the sensitivity, accuracy, and/or precision of a diagnostic test in parallel with a patient sample. A control may be a standard, e.g., for calibrating a diagnostic test or for use in measuring the nucleic acid concentration in a parallel sample (such as circulating cell-free nucleic acid).

The term "diagnostic test" as used herein, refers to any test, screen, assay, or method that may be used to characterize a genotype, such as aneuploidy, copy number variant, allelomorphism, polymorphism, splice variant, regulatory variant, mutation, indel, trinucleotide repeat, premature stop codon, translocation, somatic rearrangement, gene fusion, or the presence of foreign or exogenous nucleotide sequences (e.g., a provirus), by analyzing a sample of nucleic acids. For example, a diagnostic test may refer to next generation sequencing ("NGS") or a diagnostic test may comprise NGS, e.g., and subsequent analysis. Similarly, a diagnostic test may refer to any type of nucleic acid sequencing, or a diagnostic test may comprise any type of nucleic acid sequencing. In some embodiments, a diagnostic test may refer to nucleic acid hybridization, such as DNA microarray analysis. Similarly, a diagnostic test may comprise nucleic acid hybridization, such as DNA microarray analysis. In some embodiments, a diagnostic test may refer to quantitative PCR (qPCR) or digital PCR (dPCR), or a diagnostic test may comprise qPCR or dPCR.

The term "encode" as used herein refers to a property of one or more nucleotide sequences. A nucleotide sequence may encode a genotype if the nucleotide sequence comprises sufficient information to identify the genotype. For example, a nucleotide sequence encodes the Huntington's disease genotype if the nucleotide sequence comprises sufficient information to identify (1) a sequence of the Huntingtin gene and (2) a deleterious number of CAG trinucleotide repeats. A nucleotide sequence may encode an alternate genotype that occurs at the same genetic locus as the Huntington's disease genotype if the nucleotide sequence comprises sufficient information to identify (1) a sequence of the Huntingtin gene and (2) that the Huntingtin gene does not comprises a deleterious number of CAG trinucleotide repeats. Accordingly, many different nucleotide sequences may encode either the Huntington's disease genotype, an alternate genotype that occurs at the same genetic locus as the Huntington's disease genotype, or any genotype. Similarly, one or more nucleic acids may encode a genotype because nucleic acids comprise nucleotide sequences. Thus, a plurality of nucleic acids or a plurality of nucleotide sequences may encode a plurality of genotypes. Further, a mixture of nucleic acids may encode a genome or substantially all of a genome, e.g., a mixture of nucleic acids may encode a plurality of genotypes that comprise substantially all of the genotypes in a genome. As used herein, a mixture of nucleic acids encodes substantially all of a genome if the mixture of nucleic acids was obtained, for example, by isolating nucleic acids from one or more cells and fragmenting the isolated nucleic acids, even though some nucleotide sequences may be depleted or lost during the isolation, fragmentation, or other steps. A mixture of nucleic acids may encode substantially all of a genome even if the mixture does not comprise, for example, mitochondrial nucleotide sequences. As defined herein, a mixture of nucleic acids may encode the ploidy of a chromosome, such as aneuploidy, if the mixture of nucleic acids comprises sufficient information to identify the ratio of the copy number of one or more nucleotide sequences that have sequence homology to the chromosome to the copy number of one or more nucleotide sequence that have sequence homology to at least one different chromosome. Similarly, a plurality of nucleotide sequences may encode the ploidy of a chromosome, such as aneuploidy, if the plurality comprises sufficient information to identify the ratio of the copy number of one or more nucleotide sequences that have sequence homology to the chromosome to the copy number of one or more nucleotide sequence that have sequence homology to at least one different chromosome.

The term "fetus" as used herein refers to a mammal at any stage of development between conception and birth.

The term "genotype" refers to a genetic trait, such as aneuploidy, copy number variant, allelomorphism, polymorphism, splice variant, regulatory variant, mutation, indel, trinucleotide repeat, premature stop codon, translocation, somatic rearrangement, gene fusion, or the presence of a foreign or exogenous nucleotide sequence, such as a virus, provirus, or bacteria.

The term "liposome" refers to a lamellar composition comprising amphiphilic lipids, which typically form a lipid bilayer that defines an aqueous compartment. A liposome may be artificial, naturally-occurring, or derived, at least in part, from naturally-occurring lipids. For example, the term liposome, as used herein, may refer to a vesicle of cellular origin, such as a microvesicle, exosome, or apoptotic body. Similarly, a liposome may refer to a vesicle comprising lipids of cellular origin. Such liposomes may comprise cellular components, such as transmembrane proteins, or they may be substantially free of cellular components. A liposome may be a multilamellar vesicle or a unilamellar vesicle, such as a small unilamellar vesicle or a large unilamellar vesicle. In certain embodiments, the liposomes comprise unilamellar vesicles.

The term "mixture of nucleic acids" refers to a composition comprising at least two nucleic acids with different nucleotide sequences, i.e., a first nucleic acid may comprise a first nucleotide sequence and a second nucleic acid may comprise a second nucleotide sequence, wherein the first and second nucleotide sequences are different. Nevertheless, the first nucleotide sequence and the second nucleotide sequence may be related. For example, the first nucleotide sequence may have 100% sequence identity with a subsequence of the second nucleotide sequence, and the first and second nucleotide sequences may vary only in that the second nucleotide sequence is longer than the first nucleotide sequence. Similarly, the first nucleotide sequence and second nucleotide sequence may comprise regions with 100% sequence identity. The first nucleotide sequence and second nucleotide sequence may be related because they are derived from the same genome. In certain embodiments, each nucleic acid in a mixture of nucleic acids is either derived from a single genome (e.g., a single human genome, which may be obtained from a human cell line) or designed to replicate a feature of a single genome, such as a genotype (e.g., aneuploidy, polymorphism, mutation, allelomorphism, etc.). Thus, in some embodiments, a mixture of nucleic acids consists of nucleic acids that are isolated from a human cell line, such as a female cell line or a cell line comprising either a genotype or plurality of genotypes associated with a disease (e.g., aneuploidy, a neoplasm, or a hereditary disease), which may be further processed, e.g., to adjust the size of the nucleic acids to a desired range. A mixture of nucleic acids may comprise nucleic acids that are isolated from a single genome and additional nucleic acids, which may be added, for example, to introduce nucleotide sequences that encode a genotype, e.g., to allow the mixture of nucleic acids to serve as a control for additional genotypes, or to mask a genotype, e.g., in order to test the robustness of a diagnostic test. A mixture of nucleic acids may comprise nucleic acids that are isolated from a single genome but depleted of one or more nucleotide sequences, e.g., to remove mitochondrial or ribosomal nucleotide sequences. A mixture of nucleic acids may be derived directly from a genome, e.g., by isolating the nucleic acids from the genome, or a mixture of nucleic acids may be derived from a genome indirectly, e.g., by amplifying the nucleotide sequences in a genome and/or by cloning the nucleotide sequences of a genome. A mixture of nucleic acids may comprise nucleic acids that are not derived from the same genome; for example, the mixture may be designed to replicate a feature of a single genome. For example, a mixture of nucleic acids may comprise a first nucleotide sequence with sequence homology to a first chromosome and a second nucleotide sequence with sequence homology to a second chromosome, wherein each nucleotide sequence is derived from the same genome, the first and second nucleotide sequences are derived from different genomes, or the first and/or second nucleotide sequences are synthesized and/or cloned.

The term "neoplasm" refers to tumors, benign tumors, precancerous tumors, malignant tumors, cancers, metastatic cancers, metastatic tumors, leukemia, and lymphomas, wherein a neoplastic cell has a genotype that is associated with the neoplasm.

The term "nucleic acid" refers to a DNA or RNA molecule. Single stranded nucleic acids each comprise one nucleotide sequence that spans the length of the nucleic acid and multiple different nucleotide sequences that are subsequences of the one nucleotide sequence. Similarly, double stranded nucleic acids each comprises two nucleotide sequences that span the length of the nucleic acid and multiple different nucleotide sequences that are subsequences of the two nucleotide sequences. For example, a double stranded nucleic acid that is 10 base pairs long comprises two nucleotide sequence that are each 10 nucleotides long (and related in that one sequence is the reverse complement of the other sequence); the same double stranded nucleic acid comprises four nucleotide sequences that are 9 nucleotides long and six nucleotide sequences that are 8 nucleotides long, etc.

The term "nucleotide sequence" refers to any sequence of consecutive nucleotides, e.g., in a DNA or RNA molecule. A nucleotide sequence may be a subsequence of a different, longer nucleotide sequence. A mixture of nucleic acids may comprise a nucleotide sequence that is longer than the nucleic acids in the mixture, for example, when the mixture of nucleic acids is generated from longer nucleic acids (e.g., by fragmenting genomic DNA); such nucleotide sequences may be identified, for example, by sequencing the nucleic acids in the mixture of nucleic acids. Nucleotide sequences are read from 5' to 3'.

The term "sequence homology" as used herein refers to a nucleotide sequence that has at least 95% sequence identity to another nucleotide sequence. In some embodiments, "sequence homology" may refer to a nucleotide sequence that has at least 99% sequence identity to another nucleotide sequence. "Sequence homology" may refer to a nucleotide sequence that has 100% sequence identity to another nucleotide sequence.

The term "sequence homology to a chromosome" as used herein refers to a nucleotide sequence that has at least 95% sequence identity to one chromosome and less than 95% sequence identity to every other chromosome in the genome from which the nucleotide sequence was derived. For example, a nucleotide sequence has sequence homology to chromosome Y if the nucleotide sequence has both at least 95% sequence identity to chromosome Y and less than 95% sequence identity with chromosomes 1-23 and X. Similarly, a nucleotide sequence has sequence homology to chromosome 1, if the nucleotide sequence has both at least 95% sequence identity to either copy of chromosome 1 in a genome and less than 95% sequence identity with every other chromosome in the genome.

The term "sequence identity" refers to the percentage of nucleotides in two nucleotide sequences that are identical upon aligning the two sequences. Two nucleotide sequences may be aligned using any alignment algorithm known in the art, such as those implemented in the BLAST or Clustal suites of programs. Alignment algorithms may introduce gaps in one or both nucleotide sequences to improve an alignment score, thereby increasing a calculated sequence identity; for sequences in which gaps improve an alignment score, "sequence identity" refers to the calculated sequence identity obtained by an alignment algorithm using default weights and default scoring functions for introducing and extending gaps (often referred to as gap penalties, such as gap opening penalties and gap extension penalties).

The phrase "ratio of the copy number of any nucleotide sequence that has sequence homology with a chromosome to the copy number of any nucleotide sequence that has sequence homology to a different chromosome" and similar phrases are used herein to describe the copy number of a chromosome relative to the copy number of a different chromosome from the same genome or from the same mixture of nucleic acids. Chromosomes 1, 6, and 7 are frequently used as reference chromosomes, because aneuploidy has not observed for these chromosomes in viable humans. Thus, for example, the ratio of the copy number of any nucleotide sequence that has sequence homology to chromosome 1 to the copy number of any nucleotide sequence that has sequence homology to chromosome 6 should be 1:1 in any mixture of nucleic acids that comprises a genome, that comprises substantially all of a genome, or that is designed to replicate the stoichiometry of chromosome 1 and chromosome 6 in a genome. Nevertheless, a chromosome may comprise multiple copies of a nucleotide sequence that has sequence homology to the chromosome, e.g., the chromosome may comprise paralogous nucleotide sequences, such as copies of paralogous genes. The phrase "ratio of the copy number of any nucleotide sequence that has sequence homology with a chromosome to the copy number of any nucleotide sequence that has sequence homology to a different chromosome," and variants thereof, does not include nucleotide sequences that occur more than once in a G0 or G1 phase chromosome or more than once on a chromatid. For example, if a nucleotide sequence occurs more than once on the same chromatid, then the nucleotide sequence is not used to calculate a copy number ratio. Similarly, a chromosome may comprise nucleotide sequences that do not occur in the second copy of the chromosome, e.g., for genomes that comprise heterozygous genotypes. The phrase "ratio of the copy number of any nucleotide sequence that has sequence homology with a chromosome to the copy number of any nucleotide sequence that has sequence homology to a different chromosome," and variants thereof, only includes nucleotide sequences that occur in each chromosome of a chromosome pair (e.g., for disomic autosomes) or in each instance of a particular chromosome (e.g., for aneuploidic autosomes). Thus, a nucleotide sequence that has sequence homology with a chromosome is not used to calculate a copy number ratio if the nucleotide sequence lacks sequence homology with each copy of the chromosome.

In some embodiments, a ratio of the copy number of any nucleotide sequence that has sequence homology with a chromosome (i.e., an autosome or sex chromosome) to the copy number of any nucleotide sequence that has sequence homology to a different non-homologous chromosome (i.e., an autosome or sex chromosome) does not include (1) nucleotide sequences that occur more than once in a human G0 or G1 phase chromosome, (2) nucleotide sequences that occur more than once on a human chromatid, (3) nucleotide sequences that occur more than twice in a human G2 phase chromosome, (4) nucleotide sequences that occur exactly once in a human G2 phase chromosome, (5) nucleotide sequences that do not occur on each sister chromatid of a human G2 phase chromosome, (6) nucleotide sequences that occur on non-homologous chromosomes, and/or (7) nucleotide sequences that do not occur on each homologous chromosome from which the nucleic acids of a control were derived. The sex chromosomes X and Y are not homologous chromosomes. Every nucleotide sequence that meets the criteria for calculating a ratio comprises subsequences that do not meet the criteria for inclusion in a ratio calculation because every nucleotide sequence contains short subsequences (e.g., of 2-10 nucleotides) that are likely to occur many times on a chromosome and/or on non-homologous chromosomes.

In some embodiments, a nucleotide sequence has sequence homology to a chromosome if the nucleotide sequence has at least 95% sequence identity to the chromosome and less than 95% sequence identity to every other non-homologous chromosome in the control. In some embodiments, a nucleotide sequence has sequence homology to a chromosome if the nucleotide sequence has at least 99% sequence identity to the chromosome and less than 99% sequence identity to every other non-homologous chromosome in the control. In some embodiments, a nucleotide sequence has sequence homology to a chromosome if the nucleotide sequence has 100% sequence identity to the chromosome and less than 100% sequence identity to every other non-homologous chromosome in the control. In some embodiments, a ratio of the copy number of any nucleotide sequence that has sequence homology with a chromosome to the copy number of any nucleotide sequence that has sequence homology to a different chromosome only includes nucleotide sequences that occur exactly once on each homologous G0/G1 phase chromosome and exactly once on each homologous chromatid in the chromosomes from which the control is derived.

I. Nucleic Acids

In some aspects, the invention relates to a control comprising nucleic acids, such as a control comprising a mixture of nucleic acids. The control may be a control for use in determining the ploidy of a chromosome in a fetus, e.g., for use in calibrating an assay or diagnostic test or for use as a run control in an assay or diagnostic test. The chromosome may be human chromosome 1, 2, 3, 4, 5, 6, 7, 8, 9, 10, 11, 12, 13, 14, 15, 16, 17, 18, 19, 20, 21, 22, X, or Y. In some embodiments, the chromosome is human chromosome 8, 9, 13, 18, 21, 22, or X. The chromosome may be an autosome or a sex chromosome. In some embodiments, the control is a control for use in identifying a genotype. The genotype may be a genetic disease or the genotype may be associated with cancer. The genotype may be associated with a neoplasm, provirus, or hereditary disease. The genotype may be associated with a virus or bacteria, such as a human pathogen. In some embodiments, the genotype is not associated with a genetic disease, e.g., when the control is for use in assessing the sensitivity of a diagnostic test. The genotype may be a single nucleotide polymorphism, point mutation, premature stop codon, trinucleotide repeat, translocation, somatic rearrangement, allelomorph, single nucleotide variant, coding insertion or deletion ("indel"), splice variant, regulatory variant, copy number variant, or gene fusion. The control may be for use in identifying or characterizing a disease or condition.

The nucleic acids may comprise nucleotide sequences of any origin, such as viral, bacterial, protist, fungal, plant, or animal origin. In certain embodiments, the nucleic acids comprise human nucleotide sequences. The nucleic acids may also comprise nucleotide sequences from human pathogens, e.g., the nucleic acids may comprise viral, bacterial, protist, or fungal nucleotide sequences, wherein the virus, bacterium, protist, or fungus is a human pathogen.

In certain embodiments, the controls are substantially free of chromatin. For example, the controls may comprise nucleic acids encoding human nucleotide sequences, wherein the nucleic acids are not associated with histones and/or nucleosomes. In certain embodiments, the controls are substantially free of histones and/or nucleosomes.

The controls may comprise DNA and/or RNA. In some embodiments, the controls are substantially free of RNA.

In some embodiments, the control comprises a first mixture of nucleic acids. In some embodiments, the control comprises a first mixture of nucleic acids and a second mixture of nucleic acids.

A First Mixture of Nucleic Acids

As described herein, the first mixture of nucleic acids may comprise a first genotype (a genotype of interest), such as aneuploidy, a genotype associated with a hereditary disease, a genotype associated with a communicable disease (e.g., a virus, provirus, or bacteria), and/or a genotype associated with a neoplasm (e.g., cancer). In other embodiments, the first genotype is not associated with disease.

The first mixture of nucleic acid may comprise a nucleotide sequence that encodes the genotype. The first mixture of nucleic acid may comprise a nucleotide sequence that encodes a genotype. For example, the first mixture of nucleic acids may comprise a nucleotide sequence that has sequence homology with a chromosome, e.g., for use in detecting aneuploidy of the chromosome. In some embodiments, the first mixture of nucleic acids comprises a nucleotide sequence that encodes a gene comprising a premature stop codon, polymorphism, or trinucleotide repeat, e.g., for use in detecting a hereditary disease. In some embodiments, the first mixture of nucleic acids comprises a nucleotide sequence that encodes a bacterial, viral, or protist nucleotide sequence, e.g., for use in detecting a communicable disease. In some embodiments, the first mixture of nucleic acids comprises a nucleotide sequence that encodes a genetic mutation or a genetic rearrangement associated with a neoplasm, e.g., for use in detecting cancer, such as metastatic cancer.

The first mixture of nucleic acids may comprise one or more pluralities of nucleotide sequences, which may encode one or more genotypes, e.g., one plurality of nucleotide sequences may encode one or more genotypes.

In some embodiments, the first mixture of nucleic acids comprises nucleotide sequences encoding substantially all of the genome of a cell, plurality of cells, cell line, or subject. For example, the cell line may be an immortalized lymphocyte cell line genome, a fibroblast cell line genome, or a cytotrophoblast cell line genome. In certain embodiments, the first mixture of nucleic acids comprises nucleotide sequences encoding substantially all of the genome of a human cell, human cell line, or human subject. The first mixture of nucleic acids may be obtained from a cell, plurality of cells, cell line, or donor, e.g., a cell, plurality of cells, cell line, or donor that carries an aneuploidy, hereditary disease, provirus, and/or cancer mutation. The first mixture of nucleic acids need not comprise nucleotide sequences that encode an entire genome, however. For example, a mixture of nucleic acids derived from a cell may encode substantially all of the genome of the cell even though some nucleotide sequences may have been lost during processing steps, such as during isolation and/or fragmentation steps. Similarly, the first mixture of nucleic acids may be enriched or depleted of various nucleotide sequences, e.g., for use in testing the robustness of an assay or diagnostic test. Alternatively, the first mixture of nucleic acids may originate from one or more non-human sources, such as a host cell comprising one or more nucleotide sequences sufficient to calibrate an assay or diagnostic test or to assess its performance. In some embodiments, the first mixture of nucleic acids encodes substantially all of the genome of a cell, cell line, or subject, e.g., a human cell, plurality of human cells, human cell line, or human subject. The cell line may be, for example, GM24385. In other embodiments, the first mixture of nucleic acids does not encode the genome of a cell, cell line, or subject. The first mixture of nucleic acids may also comprise nucleotide sequences from human pathogens, e.g., the first mixture of nucleic acids may comprise viral, bacterial, protist, or fungal nucleotide sequences, wherein the virus, bacterium, protist, or fungus is a human pathogen. In some embodiments, the first mixture of nucleic acids does not encode a genome or substantially all of a genome, e.g., wherein the first mixture comprises genotypes that are associated with a disease, such as cancer, or the first mixture comprises miRNA.

In some embodiments, the first mixture of nucleic acids is obtained from a human donor, e.g., from cells or a bodily fluid of the human donor. The first mixture of nucleic acids may be obtained from peripheral blood mononuclear cells (PBMCs), lymphocytes, fibroblasts, placenta, and/or adipocytes of a human donor. The first mixture of nucleic acids may be obtained from circulating, cell-free DNA (cfDNA) from a human donor, such as a female donor. In certain preferred embodiments, the first mixture of nucleic acids is obtained from PBMCs. The first mixture of nucleic acids may be obtained from the placenta of a human donor. The first mixture of nucleic acids may comprise cell free DNA obtained from a donor (e.g., human donor). The donor may be a healthy human donor (e.g., who does not have cancer). The cell free DNA may be obtained from blood plasma or blood serum. The control may further comprise blood plasma or blood serum such as human blood plasma or human blood serum. About 50% to 100% of the control may be blood plasma or blood serum, such as about 90% to 100%, about 90% to 99.999%, or about 95% to 99.99% (e.g., wherein the blood plasma or blood serum comprises cell-free DNA). The cell free DNA may be obtained from urine. In certain embodiments, the human donor may be male or female. In certain embodiments, the donor is female.

The first mixture of nucleic acids may be substantially free of chromatin, nucleosomes, and/or histones, e.g., the first mixture of nucleic acids may comprise human nucleotide sequences that are substantially free of chromatin, nucleosomes, and histones. The first mixture of nucleic acids may be free of chromatin, nucleosomes, and/or histones. In some embodiments, the first mixture of nucleic acids comprises chromatin, nucleosomes, and/or histones. The first mixture of nucleic acids may comprise methylated nucleic acids or the first mixture of nucleic acids may be substantially free of methylated nucleic acids.

The first mixture of nucleic acids may comprise double-stranded nucleic acids that comprise "sticky" ends, e.g., wherein a double-stranded nucleic acid comprises one or two 3' overhangs, one or two 5' overhangs, or a 3' overhang and a 5' overhang. The first mixture of nucleic acids may be substantially free from 3' and/or 5' overhangs. The first mixture of nucleic acids may consist essentially of blunt-ended nucleic acids. Substantially all of the 5' ends of the nucleic acids in the first mixture may be phosphorylated. In some embodiments, substantially all of the 5' ends of the nucleic acids in the first mixture are not phosphorylated. Substantially all of the 3' ends of the nucleic acids in the first mixture may be dephosphorylated. In some embodiments, substantially all of the 3' ends of the nucleic acids in the first mixture are phosphorylated. Dephosphorylating the 5' ends of the nucleic acids (and/or 3' ends) of a control may inhibit unintended ligation. Dephosphorylation may be accomplished by a phosphatase, such as an alkaline phosphatase (e.g., calf intestinal alkaline phosphatase, bacterial alkaline phosphatase, shrimp alkaline phosphatase, placental alkaline phosphatase). Blunt-ending the nucleic acids of a control may inhibit unintended pairing and/or aggregation of nucleic acids. A nucleic acid comprising one or two sticky ends may be blunt-ended, for example, with a polymerase or a Klenow fragment. The first mixture of nucleic acids may comprise mitochondrial nucleotide sequences, or the first mixture of nucleic acids may be substantially free of mitochondrial nucleotide sequences. The first mixture of nucleic acids may comprise DNA and/or RNA. In some embodiments, the first mixture of nucleic acids is substantially free of RNA. In some embodiments, the first mixture of nucleic acids comprises RNA (e.g., microRNA).

A first nucleotide sequence of the first mixture of nucleic acids may encode a genotype of interest, such as a chromosome associated with aneuploidy, a genotype associated with a hereditary disease, a genotype associated with a communicable disease, and/or a genotype associated with a neoplasm. A second nucleotide sequence may have sequence homology to a different nucleotide sequence than the first nucleotide sequence. For example, the first nucleotide sequence may have sequence homology with a first chromosome, the second nucleotide sequence may have sequence homology with a second chromosome, and the ratio of the copy number of the first nucleotide sequence to the copy number of the second nucleotide sequence in the first mixture may be about 3:2, e.g., for use with diagnostic tests that aims to determine whether the first chromosome is present in a sample as a trisomy. Thus, the first nucleotide sequence may have sequence homology to any one of chromosomes 8, 9, 13, 18, 21, 22, or X, of which trisomy may result in a viable fetus, and the second nucleotide sequence may have sequence homology with a different chromosome, e.g., a different chromosome that is an autosome, such as chromosome 1, 6, or 7, which are commonly used as reference chromosomes. Nevertheless, even though other trisomic chromosomes are not known to result in viable offspring, the first nucleotide sequence may have sequence homology to any one of chromosomes 1, 2, 3, 4, 5, 6, 7, 8, 9, 10, 11, 12, 13, 14, 15, 16, 17, 18, 19, 20, 21, 22, X, or Y, e.g., in order to calibrate a diagnostic test or to screen for a trisomy in a fetus before the trisomy displays a lethal phenotype.

The ratio of the copy number of the first nucleotide sequence to the copy number of the second nucleotide sequence may vary from about 3:2, e.g., for diagnosing an aneuploidy other than a trisomy or for calibrating a diagnostic test or assay. Thus, in some embodiments, the ratio of the copy number of the first nucleotide sequence to the copy number of the second nucleotide sequence may be about 1:1 or greater than 1:1, such as greater than about 11:10, greater than about 10:9, greater than about 9:8, greater than about 8:7, greater than about 7:6, greater than about 6:5, greater than about 5:4, greater than about 4:3, greater than about 3:2, or greater than about 2:1. For example, in some embodiments, the first nucleotide sequence may have sequence homology to chromosome Y, the second nucleotide sequence may have sequence homology with an autosome, and the ratio of the copy number of the first nucleotide sequence to the copy number of the second nucleotide sequence may be about 1:1. In some embodiments, the ratio of the copy number of the first nucleotide sequence to the copy number of the second nucleotide sequence is about 1:1 to about 2:1, such as about 11:10 to about 2:1, about 10:9 to about 2:1, about 9:8 to about 2:1, about 8:7 to about 2:1, about 7:6 to about 2:1, about 6:5 to about 2:1, about 5:4 to about 2:1, or about 4:3 to about 2:1. In some embodiments, the ratio of the copy number of the first nucleotide sequence to the copy number of the second nucleotide sequence is about 3:2.

The first mixture of nucleic acids may comprise a third nucleotide sequence, e.g., for use in determining whether a fetus has Klinefelter syndrome. In this embodiment, the first nucleotide sequence may have sequence homology with human chromosome X; a second nucleotide sequence may have sequence homology with an autosome; a third nucleotide sequence may have sequence homology with chromosome Y; and the ratio of the copy numbers of the first, second, and third nucleotide sequences may be about 2:2:1.

In some embodiments, the first mixture of nucleic acids comprises a first plurality of nucleotide sequences and a second plurality of nucleotide sequences. Each nucleotide sequence of the first plurality may have sequence homology with a genotype of interest, such as a chromosome associated with aneuploidy, a genotype associated with a hereditary disease, a genotype associated with a communicable disease, and/or a genotype associated with a neoplasm. Each nucleotide sequence of the second plurality may have sequence homology to nucleotide sequences that are different from than the first plurality of nucleotide sequences. For example, each nucleotide sequence of the first plurality may have sequence homology with a first chromosome, each nucleotide sequence of the second plurality may each have sequence homology with a second chromosome, and the ratio of the copy number of any nucleotide sequence of the first plurality to the copy number of any nucleotide sequence of the second plurality in the first mixture may be about 3:2, e.g., for use with diagnostic tests that aims to determine whether the first chromosome is present in a sample as a trisomy. Thus, each nucleotide sequence of the first plurality may have sequence homology to any one of chromosomes 8, 9, 13, 18, 21, 22, or X, of which trisomy may result in a viable fetus, and each nucleotide sequence of the second plurality may have sequence homology with a different chromosome, e.g., a different chromosome that is an autosome. Nevertheless, even though other trisomic chromosomes are not known to result in viable offspring, the nucleotide sequences of the first plurality may have sequence homology to any one of chromosomes 1, 2, 3, 4, 5, 6, 7, 8, 9, 10, 11, 12, 13, 14, 15, 16, 17, 18, 19, 20, 21, 22, X, or Y, e.g., in order to calibrate a diagnostic test or to screen for a trisomy in a fetus before the trisomy displays a lethal phenotype. The first plurality of nucleotide sequences may encode substantially all of human chromosome 1, 2, 3, 4, 5, 6, 7, 8, 9, 10, 11, 12, 13, 14, 15, 16, 17, 18, 19, 20, 21, 22, X, or Y. The second plurality of nucleotide sequences may encode substantially all of human chromosomes 1, 2, 3, 4, 5, 6, 7, 8, 9, 10, 11, 12, 13, 14, 15, 16, 17, 18, 19, 20, 21, 22, X, and/or Y, e.g., the second plurality of nucleotide sequences may encode substantially all of human chromosomes 1, 6, and 7.

The ratio of the copy number of any nucleotide sequence of the first plurality to the copy number of any nucleotide sequence of the second plurality may vary from about 3:2, e.g., for diagnosing an aneuploidy other than a trisomy or for calibrating a diagnostic test or assay. Thus, in some embodiments, the ratio of the copy number of any nucleotide sequence of the first plurality to the copy number of any nucleotide sequence of the second plurality may be about 1:1 or greater than 1:1, such as greater than about 11:10, greater than about 10:9, greater than about 9:8, greater than about 8:7, greater than about 7:6, greater than about 6:5, greater than about 5:4, greater than about 4:3, greater than about 3:2, or greater than about 2:1. For example, in some embodiments, each nucleotide sequence of the first plurality may have sequence homology to chromosome Y, each nucleotide sequence of the second plurality may have sequence homology with an autosome, and the ratio of the copy number of any nucleotide sequence of the first plurality to the copy number of any nucleotide sequence of the second plurality may be about 1:1. In some embodiments, the ratio of the copy number of any nucleotide sequence of the first plurality to the copy number of any nucleotide sequence of the second plurality may be about 1:1 to about 2:1, such as about 11:10 to about 2:1, about 10:9 to about 2:1, about 9:8 to about 2:1, about 8:7 to about 2:1, about 7:6 to about 2:1, about 6:5 to about 2:1, about 5:4 to about 2:1, or about 4:3 to about 2:1. In some embodiments, the ratio of the copy number of any nucleotide sequence of the first plurality to the copy number of any nucleotide sequence of the second plurality is about 3:2. The first plurality of nucleotide sequences may encode substantially all of chromosome Y.

The first mixture of nucleic acids may comprise nucleotide sequences that have sequence homology with the first chromosome that are not included in the first plurality of nucleotide sequences. Similarly, the first mixture of nucleic acids may comprise nucleotide sequences that have sequence homology with the second chromosome that are not included in the second plurality of nucleotide sequences.

The first mixture of nucleic acids may comprise a third plurality of nucleotide sequences, e.g., for use in determining whether a fetus has Klinefelter syndrome. In this embodiment, each nucleotide sequence of the first plurality may have sequence homology with human chromosome X; each nucleotide sequence of the second plurality may have sequence homology with an autosome; each nucleotide sequence of the third plurality may have sequence homology with chromosome Y; and the ratio of the copy numbers of any three nucleotide sequences selected from the first, second, and third pluralities may be about 2:2:1. The first plurality of nucleotide sequences may encode substantially all of chromosome X, and/or the third plurality of nucleotide sequences may encode substantially all of chromosome Y.

The first mixture of nucleic acids may comprise a first plurality of nucleotide sequences, a second plurality of nucleotide sequences, a third plurality of nucleotide sequences, and a fourth plurality of nucleotide sequences. Each nucleotide sequence of the first plurality of nucleotide sequences may have sequence homology to chromosome 13, each nucleotide sequence of the second plurality of nucleotide sequences may have sequence homology to chromosome 18, and each nucleotide sequence of the third plurality of nucleotide sequences may have sequence homology to chromosome 21. Each nucleotide sequence of the fourth plurality of nucleotide sequences may have sequence homology to chromosome 1, 2, 3, 4, 5, 6, 7, 8, 9, 10, 11, 12, 14, 15, 16, 17, 19, 20, or 22, preferably chromosome 1, 6, or 7. The ratio of the copy numbers of any nucleotide sequence selected from the first, second, and third plurality to any nucleotide sequence selected from the fourth plurality may be about 7:6. Such a mixture may be made, for example, by combining a trisomy 13 genome, trisomy 18 genome, and a trisomy 21 genome at approximately equal concentrations. The first plurality of nucleotide sequences may encode substantially all of chromosome 13, the second plurality of nucleotide sequences may encode substantially all of chromosome 18, and/or the third plurality of nucleotide sequences may encode substantially all of chromosome 21.

The first mixture of nucleic acids may comprise a nucleotide sequence that encodes a mutation or genotype that is associated with cancer. The first mixture of nucleic acids may comprise a plurality of nucleotide sequences, wherein each nucleotide sequence of the plurality encodes a genotype (or mutation) that is associated with cancer, e.g., the plurality of nucleotide sequences may encode a plurality of genotypes wherein each genotype is associated with cancer. Each nucleic acid of the first mixture of nucleic acids may comprise exactly one nucleotide sequence of the plurality of nucleotide sequences. In some embodiments, the first mixture of nucleic acids comprises at least one nucleic acid that comprises more than one nucleotide sequence of the plurality of nucleotide sequences. For example, the first mixture of nucleic acids may comprise multiple copies of a nucleic acid that comprises each nucleotide sequence of the plurality of nucleotide sequences, e.g., for a multiplexed control.

A control may comprise each nucleotide sequence of a plurality of nucleotide sequences at a concentration of about 1 copy per mL to about $10^9$ copies per mL, such as about 1 to about $10^8$ copies per mL, about 1 to about $10^7$ copies per mL, or about 10 to about $10^6$ copies per mL. A control may comprise each nucleotide sequence of a plurality of nucleotide sequences at a concentration of about 1 to about 100 copies per mL, about 10 to about $10^3$ copies per mL, about 100 to about $10^4$ copies per mL, about $10^3$ to about $10^5$ copies per mL, about $10^4$ to about $10^6$ copies per mL, about $10^5$ to about $10^7$ copies per mL, about $10^6$ to about $10^8$ copies per mL, or about $10^7$ to about $10^9$ copies per mL. A control may comprise each nucleotide sequence of a plurality of nucleotide sequences at the same concentration (e.g., copies per mL) or at different concentrations.

A control may comprise a genotype or mutation encoded by a nucleotide sequence at a concentration of about 1 copy per mL to about $10^9$ copies per mL, such as about 1 to about $10^8$ copies per mL, about 1 to about $10^7$ copies per mL, or about 10 to about $10^6$ copies per mL. A control may comprise a genotype or mutation encoded by a nucleotide sequence at a concentration of about 1 to about 100 copies per mL, about 10 to about $10^3$ copies per mL, about 100 to about $10^4$ copies per mL, about $10^3$ to about $10^5$ copies per mL, about $10^4$ to about $10^6$ copies per mL, about $10^5$ to about $10^7$ copies per mL, about $10^6$ to about $10^8$ copies per mL, or about $10^7$ to about $10^9$ copies per mL. In some embodiments, the control is designed to replicate the copy numbers of mutations observed in circulating, cell-free DNA in the blood of cancer patients (e.g., circulating tumor DNA; ctDNA), which may range from less than 1 copy per mL to about $10^6$ copies per mL of whole blood or blood plasma (see, e.g., Dawson et al., New England J. Medicine, 368 (13):1199 (2013)).

The first mixture of nucleic acids may comprise a nucleotide sequence that encodes a genotype listed in the catalogue of somatic mutations in cancer ("COSMIC") database (see the World Wide Web at cancer.sanger.ac.uk/cosmic), and/or the first mixture of nucleic acids may comprise a nucleotide sequence that comprises a wild type genotype corresponding to any one of the genotypes listed in the COSMIC database. The first mixture of nucleic acids may comprise a plurality of nucleotide sequences, wherein each nucleotide sequence of the plurality encodes a genotype listed in the COSMIC database. For example, the first mixture of nucleic acids may comprise a plurality of nucleotide sequences, wherein the plurality of nucleotide sequences encodes 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 genotypes listed in the COSMIC database (e.g., a plurality of genotypes listed in the COSMIC database). The first mixture of nucleic acids may comprise a plurality of nucleotide sequences, wherein the plurality of nucleotide sequences encodes at least 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 genotypes listed in the COSMIC database.

Sixty-six mutations (i.e., genotypes) listed in the COSMIC database are shown in Table 1. In some embodiments, the first mixture of nucleic acids comprises a nucleotide sequence encoding a genotype listed in Table 1. The first mixture of nucleic acids may comprise a plurality of nucleotide sequences, wherein each nucleotide sequence of the plurality encodes a genotype listed in the Table 1. For example, the first mixture of nucleic acids may comprise a plurality of nucleotide sequences, wherein the plurality of nucleotide sequences encodes 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 genotypes listed in Table 1. In some embodiments, the first mixture of nucleic acids comprises a nucleotide sequence encoding a portion of a gene (and/or a regulatory region thereof) comprising a mutation, wherein the gene is selected from MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RB1, PARP2, ARHGAP5, AKT1, RAD51, IDH2, TP53, NF1, SMAD4, AKT2, ERCC1, and GNAS. In some embodiments, the first mixture of nucleic acids comprises a plurality of nucleotide sequences, wherein each nucleotide sequence of the plurality encodes a portion of a gene (and/or a regulatory region thereof) comprising a mutation, and the genes are selected from MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RB1, PARP2, ARHGAP5, AKT1, RAD51, IDH2, TP53, NF1, SMAD4, AKT2, ERCC1, and GNAS. In some embodiments, the first mixture of nucleic acids comprises a plurality of nucleotide sequences, wherein each nucleotide sequence of the plurality encodes a portion of a gene (and/or a regulatory region thereof) comprising a mutation; the nucleotide sequences of the plurality encode portions of 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, or 44 different genes; and the genes are selected from MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RB1, PARP2, ARHGAP5, AKT1, RAD51, IDH2, TP53, NF1, SMAD4, AKT2, ERCC1, and GNAS.

TABLE 1

Selected somatic mutations listed in the COSMIC database.

| Gene | Position | REF | ALT | Strand | CDS | AA | COSID |
|---|---|---|---|---|---|---|---|
| MTOR | 11291097 | T | A | − | 2664 A > T | L888F | COSM94356 |
| MPL | 43815009 | G | T | + | 1544 G > T | W515L | COSM18918 |
| NRAS | 115256529 | T | C | − | 182 A > G | Q61R | COSM584 |
| PARP1 | 226551691 | TC | T | − | 2738 del G | G913fs*4 | COSM21691 |
| AKT3 | 243809253 | T | A | − | 371 A > T | Q124L | COSM48227 |
| DNMT3A | 25457243 | G | A | − | 2644 C > T | R882C | COSM53042 |
| MSH2 | 47705449 | TG | T | + | 2250 del G | G751fs*12 | COSM111644 |
| MSH2 | 47705558 | ACT | A | + | 2359_2360 del CT | L787fs*11 | COSM26122 |
| IDH1 | 209113113 | G | A | − | 394C > T | R132C | COSM28747 |
| VHL | 10188282 | TTGAC | T | + | 426_429 del TGAC | G144fs*14 | COSM18578 |
| MLH1 | 37067240 | T | A | + | 1151 T > A | V384D | COSM26085 |
| MYD88 | 38182641 | T | C | + | 794 T > C | L265P | COSM85940 |
| CTNNB1 | 41266124 | A | G | + | 121 A > G | T41A | COSM5664 |
| ATR | 142254972 | GCTTTTAT | G | − | 3790_3796 del ATAAAAG | I1264fs*24 | COSM20627 |
| PIK3CA | 178936091 | G | A | + | 1633 G > A | E545K | COSM763 |
| PIK3CA | 178952085 | A | G | + | 3140 A > G | H1047R | COSM775 |
| PIK3CA | 178952149 | C | CA | + | 3204_3205 ins A | N1068fs*4 | COSM12464 |
| FGFR3 | 1803568 | C | G | + | 746 C > G | S249C | COSM715 |
| PDGFRA | 55141048 | T | TA | + | 1694_1695 ins A | S566fs*6 | COSM28053 |
| PDGFRA | 55152093 | A | T | + | 2525 A > T | D842V | COSM736 |
| KIT | 55599321 | A | T | + | 2447 A > T | D816V | COSM1314 |
| FBXW7 | 153249384 | C | T | − | 1394 G > A | R465H | COSM22965 |
| APC | 112175538 | GC | G | + | 4248 del C | I1417fs*2 | COSM18584 |
| APC | 112175639 | C | T | + | 4348 C > T | R1450* | COSM13127 |
| APC | 112175957 | A | AA | + | 4666_4667 ins A | T1556fs*3 | COSM18561 |
| GABRA6 | 161117296 | G | C | + | 763 G > C | V255L | COSM70853 |
| GABRG2 | 161580301 | A | G | + | 1355 A > G | Y452C | COSM74722 |
| NPM1 | 170837547 | G | GTCTG | + | 863_864 ins TCTG | W288fs*12 | COSM17559 |
| EGFR | 55242465 | GGAATTAAGAGAAGCA | G | + | 2236_2250 del 15 | E746_A750 del ELREA | COSM6225 |
| EGFR | 55249012 | C | CGGT | + | 2310_2311 ins GGT | D770_N771 ins G | COSM12378 |
| EGFR | 55249071 | C | T | + | 2369 C > T | T790M | COSM6240 |
| EGFR | 55259515 | T | G | + | 2573 T > G | L858R | COSM6224 |
| MET | 116423428 | T | G | + | 3757 T > G | YI253D | COSM700 |
| BRAF | 140453136 | A | T | − | 1799 T > A | V600E | COSM476 |
| EZH2 | 148508727 | T | A | − | 1937 A > T | Y646F | COSM37028 |
| JAK2 | 5073770 | G | T | + | 1849 G > T | V6I7F | COSM12600 |
| GNAQ | 80409488 | T | G | − | 626 A > C | Q209P | COSM28758 |
| RET | 43617416 | T | C | + | 2753 T > C | M9I8T | COSM965 |
| PTEN | 89692904 | C | T | + | 388 C > T | R130* | COSM5152 |
| PTEN | 89717716 | A | AA | + | 741_742 ins A | P248fs*5 | COSM4986 |
| PTEN | 89717774 | AA | A | + | 800 del A | K267fs*9 | COSM5809 |
| ATM | 108117846 | TGT | T | + | 1058_1059 del GT | C353fs*5 | COSM21924 |
| ATM | 108175462 | G | A | + | 5557 G > A | D1853N | COSM41596 |
| KRAS | 25398284 | C | T | − | 35 G > A | G12D | COSM521 |
| PTPN11 | 112888210 | G | A | + | 226 G > A | E76K | COSM13000 |
| FLT3 | 28592642 | C | A | − | 2503 G > T | D835Y | COSM783 |
| RB1 | 48941648 | C | T | + | 958 C > T | R320* | COSM891 |
| PARP2 | 20820412 | A | C | + | 398 A > C | D133A | COSM75849 |
| ARHGAP5 | 32561739 | G | A | + | 1864 G > A | E622K | COSM88502 |
| AKT1 | 105246455 | C | T | − | 145 G > A | E49K | COSM36918 |
| AKT1 | 105246551 | C | T | − | 49 G > A | E17K | COSM33765 |
| RAD51 | 41001312 | C | T | + | 433 C > T | Q145* | COSM117943 |
| IDH2 | 90631838 | C | T | − | 515 G > A | R172K | COSM33733 |
| IDH2 | 90631934 | C | T | − | 419 G > A | R140Q | COSM41590 |

TABLE 1-continued

Selected somatic mutations listed in the COSMIC database.

| Gene  | Position | REF | ALT | Strand | CDS           | AA        | COSID     |
|-------|----------|-----|-----|--------|---------------|-----------|-----------|
| TP53  | 7577120  | C   | T   | −      | 818 G > A     | R273H     | COSM10660 |
| TP53  | 7577538  | C   | T   | −      | 743 G > A     | R248Q     | COSM10662 |
| TP53  | 7577557  | AG  | A   | −      | 723 del C     | C242fs*5  | COSM6530  |
| TP53  | 7578406  | C   | T   | −      | 524 G > A     | R175H     | COSM10648 |
| TP53  | 7579423  | GG  | G   | −      | 263 del C     | S90fs*33  | COSM18610 |
| NF1   | 29556989 | T   | TAC | +      | 2987_2988 ins AC | R997fs*16 | COSM41820 |
| NF1   | 29576111 | C   | T   | +      | 4084 C > T    | R1362*    | COSM24443 |
| NF1   | 29679317 | TG  | T   | +      | 7501 del G    | E2501fs*22| COSM24468 |
| SMAD4 | 48603093 | T   | TT  | +      | 1394_1395 ins T | A466fs*28 | COSM14105 |
| AKT2  | 40761084 | C   | A   | −      | 268 G > T     | V90L      | COSM93894 |
| ERCC1 | 45924470 | G   | T   | −      | 287 C > A     | A96E      | COSM140843|
| GNAS  | 57484420 | C   | T   | +      | 601 C > T     | R201C     | COSM27887 |

In some embodiments, the first mixture of nucleic acids comprises a plurality of nucleotide sequences, wherein each nucleotide sequence of the plurality encodes a portion of a gene and/or a regulatory region thereof comprising a mutation, and the genes are selected from ABI1, ABL1, ABL2, ACSL3, ACUR1, AF15Q14, AF1Q, AF3P21, AF5Q31, AKAP9, AKT1, AKT2, AKT3, AL017, ALDH2, ALK, AMER1, APC, APEX1, AR, AR1D1A, ARAF, ARHGAP5, ARHGEF12, ARHH, ARID1A, ARID2, ARNT, ASPSCR1, ASXL1, ATF1, ATIC, ATM, ATP11B, ATP1A1, ATP2B3, ATR, ATRX, AXIN1, BAP1, BCL10, BCL11A, BCL11B, BCL2, BCL2L1, BCL3, BCL5, BCL6, BCL7A, BCL9, BCOR, BCR, BHD, BIRC2, BIRC3, BLM, BMPR1A, BRAF, BRC42, BRCA1, BRCA2, BRD3, BRD4, BRIP1, BTG1, BUB1B, C12ORF9, C15ORF21, C15ORF55, C16ORF75, C2ORF44, CACNA1D, CALR, CAMTA1, CANT1. CARD11, CARS, CASP8, CBFA2T1, CBFA2T3, CBFB, CBL, CBLB, CBLC, CCDC$_6$, CCNB1IP1, CCND1, CCND2, CCND3, CCNE1, CD273, CD274, CD44, CD74, CD79A, CD79B, CDC73, CDH1, CDH11, CDK12, CDK4, CDK6, CDKN2A, CDKN2A(PL4), CDKN2B, CDKN2C, CDX2, CEBPA, CEP1, CEP89, CHCHD7, CHEK2, CHIC2, CHN1, CIC, CIITA, CLIP1, CLTC, CLTCL1, CMKOR1, CNOT3, COL1A1, COL2A1, COPEB, COX6C, CREB1, CREB3L1, CREB3L2, CREBBP, CRLF2, CRTC3, CSF1R, CSF3R, CSNK2A1, CTNNB1, CUX1, CYLD, D10S170, DAXX, DCTN1, DDB2, DDIT3, DDR2, DDX10, DDX5, DDX6, DEK, DICERL, DNM2, DNMT3A, DUX4, EBFL, ECT2L, EGFR, E1F3E, EIF4A2, ELF4, ELK4, ELKS, ELL, ELN, EML4, EP300, EPS 15, ERBB2, ERBB2 ("HER2"), ERBB3, ERBB4 ("HER4"), ERC1, ERCC1, ERCC2, ERCC3, ERCC4, ERCC5, ERG, ESR1, ETV1, ETV4, ETV5, ETV6, EVI1, EWSR1, EXT1, EXT2, EZH2, EZR, FACL6, FAM46C, FANCA, FANCC, FANCD2, FANCE, FANCF, FANCG, FANCL, FAS, FBXO11, FBXW7, FCGR2B, FEV, FGFR1, FGFR1OP, FGFR2, FGFR3, FGFR4, FH, FHIT, FIPIL1, FLJ27352, FLT3, FLU, FNBP1, FOX03A, FOX04, FOXAL FOXL2, FOXOIA, FOXP1, FSTL3, FUBP1, FUS, FVT1, GABRA6, GABRG2, GAS6, GAS7, GATA1, GATA2, GATA3, GMPS, GNA11, GNAQ, GNAS, GOLGA5, GOPC, GPC3, GPHN, GRAF, H3F3A, H3F3B, HCMOGT-1, HEAB, HERPUD1, HEY1, HIP1, HIST1H3B, HIST1H4L, HLA-A, HLF, HLXB9, HMGA1, HMGA2, HNF1A, HNRNPA2B1, HOOKS, HOXA11, HOXA13, HOXA9, HOXC11, HOXC13, HOXD11, HOXD13, HPAS, HRAS, HSPCA, HSPCB, IDH1, IDH2, IGF1R, IGH, IGK, IGL, IHD2, IKZF1, IL2, IL21R, IL6, IL6ST, IL7R, IRF4, IRTA1, ITK, JAK1, JAK2, JAK3, JAZF1, JUN, KCNJ5, KDM5A, KDM5C, KDM6A, KDR, KIAA1549, KIAA1598, KIF5B, KIT, KLF4, KLK2, KMT2A. KMT2D, KRAS, KTN1, LAF4, LASP1, LCK, LCP1, LCX, LHFP, LIFR, LM02, LMNA, LMOL, LPP, LRIG3, LSM14A, LYL1, MAF, MAFB, MALAT1, MALT1, MAML2, MAP2K1, MAP2K2, MAP2K4, MAX, MCL1, MDM2, MDM4, MDS1, MDS2, MECOM, MECT1, MED 12, MEN1, MET, MITF, MKL1, MLF1, MLH1, MLL, MLL3, MLLT1, MLLT10, MLLT2, MLLT3, MLLT4, MLLT6, MLLT7, MN1, MPL, MSF, MSH2, MSH6, MSI2, MSN, MTCP1, MTOR, MUC1, MUTYH, MY018A, MY05A, MYB, MYC, MYCL MYCL1, MYON, MYD88, MYH11, MYH9, MYST4, NAB2, NACA, NBSL, NCOA1, NCOA2, NCOA4, NDRG1, NF1, NF2, NFATC2, NFE2L2, NF1B, NFKB2, NIN, NKX2-1, NKX2-1, NKX2-8, NONO, NOTCH1, NOTCH2, NPM1, NR4A3, NRAS, NRAS/CSDE1, NRG1, NSD1, NT5C2, NTRK1, NTRK3, NUMA1, NUP214, NUP98, NUTM2A, NUTM2B, OLIG2, OMD, P2RY8, PAFAH1B2, PALB2, PARP1, PARP2, PAX3, PAX5, PAX7, PAX8, PBRM1, PBX1, PCM1, PCSK7, PDCD1LG2, PDE4DIP, PDGFB, PDGFRA, PDGFRB, PERI, PHF6, PHOX2B, PICALM, PIK3CA, PIK3R1, PIM1, PLAG1, PLCG1, PML, PMS1, PMS2, PMX1, PNP, PNUTL1, POT1, POU2AF1, POU5F1, PPARG, PPFIBP1, PPP2R1A, PRCC, PRDM1, PRDM16, PRF1, PRKAR1A, PSIP1, PTCH1, PTEN, PTPN11, PTPRB, PTPRC, PTPRK, PWWP2A, RAB5EP, RAC1, RAD21, RAD51, RAD51L1, RAF1, RAFT, RALGDS, RANBP17, RAP1GDS1, RARA, RB1, RBI, RBM15, RECQL4, REL, RET, RHEB, RHOA, RIT1, RNF43, ROS1, RPL10, RPL22, RPL5, RPN1, RPS6KB1, RSP02, RSP03, RUNDC2A, RUNX1, RUNX1T1, RUNXBP2, SBDS, SDC4, SDH5, SDHB, SDHC, SDHD, SET, SETBP1, SETD2, SF3B1, SFPQ, SFRS3, SH2B3, SH3GL1, SIL, SLC34A2, SLC45A3, SMAD4, SMARCA4, SMARCB1, SMARCE1, SMO, SOCS1, SOX2, SRC, SRGAP3, SRSF2, SS18, SS18L1, SSX1, SSX2, SSX4, STAG2, STATS, STAT5B, STAT6, STK11, STL, SUFU, SUZ12, SYK, TAF15, TAL1, TAL2, TAL1, TBL1XR1, TCEA1, TCF1, TCF12, TCF3, TCF7L2, TCL1A, TCL6, TERT, TET2, TFE3, TFEB, TFG, TFPT, TFRC, THRAP3, TIAF1, TIF1, TLX1, TLX3, TMPRSS2, TNFAIP3, TNFRSF14, TNFRSFI7, TOPI, TP53, TPM3, TPM4, TPR, TRA, TRAF7, TRB, TRD, TRIM27, TRIM33, TRIP11, TRRAP, TSC1, TSC2, TSHR, TTL, U2AF1, UBR5, USP6, VHL, VT11A, WAS, WHSC1, WHSC1L1, WIF1, WRN, WT1, WWTR1, XPA, XPC, XPO1, YWHAE, ZCCHC8, ZNF145, ZNF198, ZNF217, ZNF278, ZNF331, ZNF384, ZNF521, ZNF9, ZRSR2, and ZRSR2. In some embodiments, each genotype of a plurality of genotypes consists of a mutation to a gene and/or a regulatory region thereof selected from the foregoing genes.

A mutation or genotype may be selected from the group consisting of mutation c.145G>A to gene AKT1, mutation c.49G>A to gene AKT1, mutation c.268G>T to gene AKT2, mutation c.371 A>T to gene AKT3, mutation c.4248del C to gene APC, mutation c.4348C>T to gene APC, mutation c.4666_4667insA to gene APC, mutation c.1864G>A to gene ARHGAP5, mutation c.1058_1059de1GT to gene ATM, mutation c.5557G>A to gene ATM, mutation c.3790_3796delATAAAAG to gene ATR, mutation c.1799T>A to gene BRAF, mutation c.121A>G to gene CTNNB1, mutation c.2644C>T to gene DNMT3A, mutation c.2236_2250de115 to gene EGFR, mutation c.2310_2311insGGT to gene EGFR, mutation c.2369C>T to gene EGFR, mutation c.2573T>G to gene EGFR, mutation c.2324_2325ins12 to gene ERBB2, mutation c.287C>A to gene ERCC1, mutation c.1937A>T to gene EZH2, mutation c.1394G>A to gene FBXW7, mutation c.746C>G to gene FGFR3, mutation c.2503G>T to gene FLT3, mutation c.763G>C to gene GABRA6, mutation c.1355A>G to gene GABRG2, mutation c.626A>C to gene GNAQ, mutation c.601C>T to gene GNAS, mutation c.394C>T to gene IDH1, mutation c.515G>A to gene IDH2, mutation c.419G>A to gene IDH2, mutation c.1849G>T to gene JAK2, mutation c.2447A>T to gene KIT, mutation c.1679T>A to gene KIT, mutation c.35G>A to gene KRAS, mutation c.3757T>G to gene MET, mutation c.1151T>A to gene MLH1, mutation c.1544G>T to gene MPL, mutation c.2250delG to gene MSH2, mutation c.2359_2360delCT to gene MSH2, mutation c.2664A>T to gene MTOR, mutation c.794T>C to gene MYD88, mutation c.2987_2988insAC to gene NF1, mutation c.4084C>T to gene NF1, mutation c.7501delG to gene NF1, mutation c.863_864insTCTG to gene NPM1, mutation c.182A>G to gene NRAS, mutation c.2738delG to gene PARP1, mutation c.398A>C to gene PARP2, mutation c.1694_1695insA to gene PDGFRA, mutation c.2525A>T to gene PDGFRA, mutation c.1633G>A to gene PIK3CA, mutation c.3140A>G to gene PIK3CA, mutation c.3204_3205insA to gene PIK3CA, mutation c.388C>T to gene PTEN, mutation c.741_742insA to gene PTEN, mutation c.800de1A to gene PTEN, mutation c.226G>A to gene PTPN11, mutation c.433C>T to gene RAD51, mutation c.958C>T to gene RB1, mutation c.2753T>C to gene RET, mutation c.1394_1395insT to gene SMAD4, mutation c.818G>A to gene TP53, mutation c.743G>A to gene TP53, mutation c.723delC to gene TP53, mutation c.524G>A to gene TP53, mutation c.263de1C to gene TP53, and mutation c.426_429delTGAC to gene VHL. Each genotype of a plurality of genotypes may be selected from the foregoing mutations/genotypes.

In some embodiments, the genotype is a mutation to a gene selected from the group consisting of MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RB1, PARP2, ARHGAP5, AKT1, RAD51, IDH2, TP53, NF1, SMAD4, AKT2, ERCC1, and GNAS and/or a regulatory region of any one of the foregoing. In some embodiments, each genotype of the plurality of genotypes consists of a mutation to a gene selected from the group consisting of MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RB1, PARP2, ARHGAP5, AKT1, RAD51, IDH2, TP53, NF1, SMAD4, AKT2, ERCC1, and GNAS and/or a regulatory region of any one of the foregoing.

In addition to the COSMIC database, specific mutations have been identified as somatic mutations that frequently occur in various cancers. For example, Boland et al. identified 26 different genes that are frequently mutated in various cancer types (see Boland, G. M., et al. Oncotarget, 6(24):20099 (2015)). Accordingly, in some embodiments, the first mixture of nucleic acids comprises a nucleotide sequence encoding a portion of a gene (and/or a regulatory region thereof) comprising a mutation, wherein the gene is selected from AKT1, ATM, BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA, PTEN, RET, and STK11. In some embodiments, the first mixture of nucleic acids comprises a plurality of nucleotide sequences, wherein each nucleotide sequence of the plurality encodes a portion of a gene (and/or a regulatory region thereof) comprising a mutation, and the genes are selected from AKT1, ATM, BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA, PTEN, RET, and STK11. In some embodiments, the first mixture of nucleic acids comprises a plurality of nucleotide sequences, wherein each nucleotide sequence of the plurality encodes a portion of a gene (and/or a regulatory region thereof) comprising a mutation, the nucleotide sequences of the plurality encode portions of 1, 2, 3, 4, 5, 6, 7, 8, 9, 10, 11, 12, 13, 14, 15, 16, 17, 18, 19, 20, 1, 22, 23, 24, 25, or 26 different genes, and the genes are selected from AKT1, ATM, BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA, PTEN, RET, and STK11.

In some embodiments, the genotype is a mutation to a gene selected from the group consisting of AKT1, ATM, BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA, PTEN, RET, and STK11 and/or a regulatory region of any one of the foregoing. In some embodiments, each genotype of the plurality of genotypes consists of a mutation to a gene selected from the group consisting of AKT1, ATM, BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA, PTEN, RET, and STK11 and/or a regulatory region of any one of the foregoing.

In some embodiments, the first mixture of nucleic acids comprises a nucleotide sequence encoding a portion of a gene (and/or a regulatory region thereof) comprising a mutation, wherein the gene is selected from ABL1, AKT1, ALK, APC, AR, AR1D1A, ARAF, ATM, BCL2, BCR, BRAF, BRC42, BRCA1, BRCA2, BRIP1, CCND1. CCND2, CCNE1, CDH1, CDK4, CDK6, CDKN2A, CDKN2B, CSF1R, CTNNB1, DDR2, EGFR, ERBB2, ERBB3, ERBB4, ESR1, ETV1, ETV4, ETV6, EWSR1, EZH2, FANCA, FANCC, FANCD2, FANCE, FANCF, FANCG, FANCL, FBXW7, FGFR1, FGFR2, FGFR3, FLT3, FOXL2, GATA3, GNA11, GNAQ, GNAS, HER/

ERBB2, HNF1A, HPAS, HRAS, IDH1, IDH2, IHD2, JAK2, JAK3, KDR, KIT, KRAS, MAP2K1, MAP2K2, MET, MLH1, MLL, MPL, MSH2, MSH6, MTOR, MYC, MYCN, NF1, NF2, NFE2L2, NOTCH1, NPM1, NRAS, NTRK1, PALB2, PDGFRA, PDGFRB, PIK3CA, PMS2, PTCH1, PTEN, PTPN11, RAFT, RARA, RBI, RET, RHEB, RHOA, RIT1, ROS1, SMAD4, SMARCB1, SMO, SRC, STK11, TERT, TMPRSS2, TP53, TSC1, TSC2, and VHL. In some embodiments, the first mixture of nucleic acids comprises a plurality of nucleotide sequences, wherein each nucleotide sequence of the plurality encodes a portion of a gene (and/or a regulatory region thereof) comprising a mutation, and the genes are selected from ABL1, AKT1, ALK, APC, AR, AR1D1A, ARAF, ATM, BCL2, BCR, BRAF, BRC42, BRCA1, BRCA2, BRIP1, CCND1, CCND2, CCNE1, CDH1, CDK4, CDK6, CDKN2A, CDKN2B, CSF1R, CTNNB1, DDR2, EGFR, ERBB2, ERBB3, ERBB4, ESR1, ETV1, ETV4, ETV6, EWSR1, EZH2, FANCA, FANCC, FANCD2, FANCE, FANCF, FANCG, FANCL, FBXW7, FGFR1, FGFR2, FGFR3, FLT3, FOXL2, GATA3, GNA11, GNAQ, GNAS, HER/ERBB2, HNF1A, HPAS, HRAS, IDH1, IDH2, 1HD2, JAK2, JAK3, KDR, KIT, KRAS, MAP2K1, MAP2K2, MET, MLH1, MLL, MPL, MSH2, MSH6, MTOR, MYC, MYCN, NF1, NF2, NFE2L2, NOTCH1, NPM1, NRAS, NTRK1, PALB2, PDGFRA, PDGFRB, PIK3CA, PMS2, PTCH1, PTEN, PTPN11, RAFT, RARA, RB1, RET, RHEB, RHOA, RIT1, ROS1, SMAD4, SMARCB1, SMO, SRC, STK11, TERT, TMPRSS2, TP53, TSC1, TSC2, and VHL. In some embodiments, the first mixture of nucleic acids comprises a plurality of nucleotide sequences, wherein each nucleotide sequence of the plurality encodes a portion of a gene (and/or a regulatory region thereof) comprising a mutation, the nucleotide sequences of the plurality encode portions of 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 different genes, and the genes are selected from ABL1, AKT1, ALK, APC, AR, AR1D1A, ARAF, ATM, BCL2, BCR, BRAF, BRC42, BRCA1, BRCA2, BRIP1, CCND1, CCND2, CCNE1, CDH1, CDK4, CDK6, CDKN2A, CDKN2B, CSF1R, CTNNB1, DDR2, EGFR, ERBB2, ERBB3, ERBB4, ESR1, ETV1, ETV4, ETV6, EWSR1, EZH2, FANCA, FANCC, FANCD2, FANCE, FANCF, FANCG, FANCL, FBXW7, FGFR1, FGFR2, FGFR3, FLT3, FOXL2, GATA3, GNA11, GNAQ, GNAS, HER/ERBB2, HNF1A, HPAS, HRAS, IDH1, IDH2, IHD2, JAK2, JAK3, KDR, KIT, KRAS, MAP2K1, MAP2K2, MET, MLH1, MLL, MPL, MSH2, MSH6, MTOR, MYC, MYCN, NFL NF2, NFE2L2, NOTCH1, NPM1, NRAS, NTRK1, PALB2, PDGFRA, PDGFRB, PIK3CA, PMS2, PTCH1, PTEN, PTPN11, RAFT, RARA, RBI, RET, RHEB, RHOA, RIT1, ROS1, SMAD4, SMARCB1, SMO, SRC, STK11, TERT, TMPRSS2, TP53, TSC1, TSC2, and VHL.

In some embodiments, the genotype is a mutation to a gene selected from the group consisting of ABL1, AKT1, ALK, APC, AR, AR1D1A, ARAF, ATM, BCL2, BCR, BRAF, BRC42, BRCA1, BRCA2, BRIP1, CCND1, CCND2, CCNE1, CDH1, CDK4, CDK6, CDKN2A, CDKN2B, CSF1R, CTNNB1, DDR2, EGFR, ERBB2, ERBB3, ERBB4, ESR1, ETV1, ETV4, ETV6, EWSR1, EZH2, FANCA, FANCC, FANCD2, FANCE, FANCF, FANCG, FANCL, FBXW7, FGFR1, FGFR2, FGFR3, FLT3, FOXL2, GATA3, GNA11, GNAQ, GNAS, HER/ ERBB2, HNF1A, HPAS, HRAS, IDH1, IDH2, IHD2, JAK2, JAK3, KDR, KIT, KRAS, MAP2K1, MAP2K2, MET, MLH1, MLL, MPL, MSH2, MSH6, MTOR, MYC, MYCN, NF1, NF2, NFE2L2, NOTCH1, NPM1, NRAS, NTRK1, PALB2, PDGFRA, PDGFRB, PIK3CA, PMS2, PTCH1, PTEN, PTPN11, RAFT, RARA, RBI, RET, RHEB, RHOA, RIT1, ROS1, SMAD4, SMARCB1, SMO, SRC, STK11, TERT, TMPRSS2, TP53, TSC1, TSC2, and VHL and/or a regulatory region of any one of the foregoing. In some embodiments, each genotype of the plurality of genotypes consists of a mutation to a gene selected from the group consisting of ABL1, AKT1, ALK, APC, AR, AR1D1A, ARAF, ATM, BCL2, BCR, BRAF, BRC42, BRCA1, BRCA2, BRIP1, CCND1, CCND2, CCNE1, CDH1, CDK4, CDK6, CDKN2A, CDKN2B, CSF1R, CTNNB1, DDR2, EGFR, ERBB2, ERBB3, ERBB4, ESR1, ETV1, ETV4, ETV6, EWSR1, EZH2, FANCA, FANCC, FANCD2, FANCE, FANCF, FANCG, FANCL, FBXW7, FGFR1, FGFR2, FGFR3, FLT3, FOXL2, GATA3, GNA11, GNAQ, GNAS, HER/ERBB2, HNF1A, HPAS, HRAS, IDH1, IDH2, IHD2, JAK2, JAK3, KDR, KIT, KRAS, MAP2K1, MAP2K2, MET, MLH1, MLL, MPL, MSH2, MSH6, MTOR, MYC, MYCN, NF1, NF2, NFE2L2, NOTCH1, NPM1, NRAS, NTRK1, PALB2, PDGFRA, PDGFRB, PIK3CA, PMS2, PTCH1, PTEN, PTPN11, RAFT, RARA, RBI, RET, RHEB, RHOA, RIT1, ROS1, SMAD4, SMARCB1, SMO, SRC, STK11, TERT, TMPRSS2, TP53, TSC1, TSC2, and VHL and/or a regulatory region of any one of the foregoing.

In some embodiments, the first mixture of nucleic acids comprises a nucleotide sequence encoding a portion of a gene comprising a mutation, wherein the gene is BRAF and the mutation is V600E, the gene is EGFR and the mutation is T790M, the gene is EFGR and the mutation is delL747-P753insS, the gene is ERBB2 and the mutation is A775_G776insYVMA, or the gene is KRAS and the mutation is G12D. In some embodiments, the first mixture of nucleic acids comprises a plurality of nucleotide sequences, wherein each nucleotide sequence of the plurality encodes a portion of a gene (and/or a regulatory region thereof) comprising a mutation, and the genes are selected from BRAF, EGFR, ERBB2, and KRAS and the mutations are selected from V600E (BRAF), T790M (EGFR), delL747-P753insS, (EGFR), A775_G776insYVMA (ERBB2), and G12D (KRAS). In some embodiments, the first mixture of nucleic acids comprises a plurality of nucleotide sequences, wherein each nucleotide sequence of the plurality encodes a portion of a gene comprising a mutation, the nucleotide sequences of the plurality encode portions of 1, 2, 3, or 4 different genes, and the genes are selected from BRAF, EGFR, ERBB2, and KRAS.

In some embodiments, the first mixture of nucleic acids comprises a nucleotide sequence encoding a portion of a gene comprising a mutation selected from mutation V600E to gene BRAF, mutation D770_N771insG to gene EGFR, mutation E746_A750delELREA to gene EGFR, mutation T790M to gene EGFR, mutation D816V to gene KIT, mutation G12D to gene KRAS, mutation Q61R to gene NRAS, mutation H1047R to gene PIK3CA, and mutation N1068fs*4 to gene PIK3CA. In some embodiments, the first mixture of nucleic acids comprises a plurality of nucleotide sequences, wherein each nucleotide sequence of the plurality encodes a portion of a gene comprising a mutation, the nucleotide sequences of the plurality encode portions of 1, 2, 3, 4, 5, 6, or 7 different genes, and the genes are selected from BRAF, EGFR, ERBB2, KIT, KRAS, NRAS, and PIK3CA. For example, the plurality of nucleotide sequences may encode 1, 2, 3, 4, 5, 6, 7, 8, or 9 of mutation V600E to gene BRAF, mutation D770_N771insG to gene EGFR, mutation E746_A750delELREA to gene EGFR, mutation T790M to gene EGFR, mutation D816V to gene KIT, mutation G12D to gene KRAS, mutation Q61R to gene NRAS, mutation H1047R to gene PIK3CA, and mutation N1068fs*4 to gene PIK3CA.

In some embodiments, the genotype is a mutation to a gene selected from the group consisting of BRAF, EGFR, ERBB2, and KRAS. In some embodiments, each genotype of the plurality of genotypes consists of a mutation to a gene selected from the group consisting of BRAF, EGFR, ERBB2, and KRAS.

In some embodiments, the first mixture of nucleic acids comprises RNA, such as microRNA ("miRNA" or "miR"). The first mixture of nucleic acids may comprise one or more nucleotide sequences encoding one or more microRNAs selected from miR-224-5p, miR-452-5p, miR-23b-5p, miR-203-5p, miR-1201-5p, miR-149-5p, miR-671-3p, miR-944-5p, miR-27b-3p, and miR-22-3p, which are downregulated in certain cancers (see, e.g., Warnecke-Eberz, U. et al., Tumor Biology 36(6):4643 (2015)). The first mixture of nucleic acids may comprise one or more nucleotide sequences encoding one or more microRNAs selected from miR-223-5p, miR-223-3p, miR-483-5p, miR-409-3p, miR-196b-5p, miR-192-5p, miR-146a-5p, and miR-126-5p, which are upregulated in certain cancers (see, e.g., Warnecke-Eberz, U. et al., Tumor Biology 36(6):4643 (2015)). In some embodiments, the first mixture of nucleic acids comprises a plurality of nucleotide sequences, and each nucleotide sequence of the plurality is selected from a nucleotide sequence encoding a microRNA selected from miR-224-5p, miR-452-5p, miR-23b-5p, miR-203-5p, miR-1201-5p, miR-149-5p, miR-671-3p, miR-944-5p, miR-27b-3p, miR-22-3p, miR-223-5p, miR-223-3p, miR-483-5p, miR-409-3p, miR-196b-5p, miR-192-5p, miR-146a-5p, and miR-126-5p.

The first mixture of nucleic acids may comprise one or more nucleotide sequences encoding one or more microRNAs selected from hsa-miR-16-5p, hsa-miR-17-5p, hsa-miR-19a-3p, hsa-miR-19b-3p, and hsa-miR-20a-5p, which are predictive of gestational diabetes mellitus (see, e.g., Zhu, Y., et al., Int. J. Gynecology Obstetrics 130(1):49 (2015)). In some embodiments, the first mixture of nucleic acids comprises a plurality of nucleotide sequences, and each nucleotide sequence of the plurality is selected from a nucleotide sequence encoding a microRNA selected from hsa-miR-16-5p, hsa-miR-17-5p, hsa-miR-19a-3p, hsa-miR-19b-3p, and hsa-miR-20a-5p.

The first mixture of nucleic acids may comprise one or more nucleotide sequences encoding one or more microRNAs selected from let-7a, let-7b, let-7c, let-7d, let-7e, and let-7f, which may correlate with the invasiveness of ovarian cancer (see, e.g., Kobayashi, M. et al., J. Translational Medicine 12:4 (2014)). The first mixture of nucleic acids may comprise one or more nucleotide sequences encoding one or more microRNAs selected from miR-200a, miR-200b, and miR-200c, which are associated with low-invasive ovarian cancer (see, e.g., Kobayashi, M. et al., J. Translational Medicine 12:4 (2014)). In some embodiments, the first mixture of nucleic acids comprises a plurality of nucleotide sequences, and each nucleotide sequence of the plurality is selected from a nucleotide sequences encoding a microRNA selected from let-7a, let-7b, let-7c, let-7d, let-7e, let-7f, miR-200a, miR-200b, and miR-200c.

The first mixture of nucleic acids may comprise one or more nucleotide sequences encoding one or more microRNAs selected from miR-21, miR-494, and miR-1973, which are upregulated in Hodgkin's lymphoma. The first mixture of nucleic acids may comprise the nucleotide sequence encoding the microRNA miR-185, which correlates with colorectal cancer metastasis, and/or the nucleotide sequence encoding the microRNA miR-133h. which inversely correlates with colorectal cancer metastasis. The first mixture of nucleic acids may comprise the nucleotide sequence of the microRNA miR-324a, which correlates with survival for patients with non-small cell lung cancer. The first mixture of nucleic acids may comprise the nucleotide sequence of the microRNA miR-21, which correlates with cell proliferation in hepatocellular carcinomas. The first mixture of nucleic acids may comprise the nucleotide sequence of the microRNA miR-205, which inversely correlates with breast cancer metastasis. The first mixture of nucleic acids may comprise one or more nucleotide sequences encoding one or more microRNAs selected from miR-200a, miR-200b, miR-200c, miR-141 and miR-429, which are inversely correlated with breast cancer progression.

Various microRNAs of specific sequences are found in human plasma at concentrations of less than 1 copy per mL to about $10^5$ copies per mL. A control may comprise a nucleotide sequence of a microRNA at a concentration of about 1 copy per mL to about $10^9$ copies per mL, such as about 1 to about $10^8$ copies per mL, about 1 to about $10^7$ copies per mL, or about 10 to about $10^6$ copies per mL. A control may comprise each nucleotide sequence of a plurality of microRNA nucleotide sequences at a concentration of about 1 to about 100 copies per mL, about 10 to about $10^3$ copies per mL, about 100 to about $10^4$ copies per mL, about $10^3$ to about $10^5$ copies per mL, about $10^4$ to about $10^6$ copies per mL, about $10^5$ to about $10^7$ copies per mL, about $10^6$ to about $10^8$ copies per mL, or about $10^7$ to about $10^9$ copies per mL. A control may comprise each nucleotide sequence of a plurality of microRNA nucleotide sequences at the same concentration (e.g., copies per mL) or at different concentrations.

Each nucleotide sequence of a plurality of microRNA nucleotide sequences may exist on a different nucleic acid of the first mixture, or the same nucleic acid of the first mixture may comprise more than one microRNA nucleotide sequences of a plurality. For example, each nucleotide sequence of a plurality of microRNA nucleotide sequences may exist on the same nucleic acid of the first mixture, e.g., for a "multiplexed" control. Thus, the first mixture of nucleic acids may consist essentially of multiple copies a nucleic acid encoding each nucleotide sequence of a plurality of microRNA nucleotide sequences. In other embodiments, the first mixture of nucleic acids consists essentially of multiple copies of nucleic acids wherein each nucleotide sequence of a plurality of microRNA nucleotide sequences exists on a nucleic acid that does not contain any other nucleotide sequence of the plurality.

Each nucleic acid of the first mixture of nucleic acids may comprise exactly one nucleotide sequence of the plurality of microRNA nucleotide sequences. In some embodiments, the first mixture of nucleic acids comprises at least one nucleic acid that comprises more than one nucleotide sequence of the plurality of microRNA nucleotide sequences. For example, the first mixture of nucleic acids may comprise multiple copies of a nucleic acid that comprises each nucleotide sequence of the plurality of microRNA nucleotide sequences, e.g., for a multiplexed control.

In some embodiments, the first mixture of nucleic acids comprises a plurality of microRNA nucleotide sequences. Each nucleotide sequence of the plurality of microRNA nucleotide sequences may be selected from the nucleotide sequence of miR-224-5p, miR-452-5p, miR-23b-5p, miR-203-5p, miR-1201-5p, miR-149-5p, miR-671-3p, miR-944-5p, miR-27b-3p, miR-22-3p, miR-223-5p, miR-223-3p, miR-483-5p, miR-409-3p, miR-196b-5p, miR-192-5p, miR-146a-5p, miR-126-5p, hsa-miR-16-5p, hsa-miR-17-5p, hsa-miR-19a-3p, hsa-miR-19b-3p, hsa-miR-20a-5p, let-7a, let-7b, let-7c, let-7d, let-7e, let-7f, miR-200a, miR-200b, and miR-200c. Thus, the first mixture of nucleic acids may comprise a plurality of microRNA nucleotide sequences, wherein the plurality comprises the nucleotide sequences of miR-224-5p, miR-452-5p, miR-23b-5p, miR-203-5p, miR-1201-5p, miR-149-5p, miR-671-3p, miR-944-5p, miR-27b-3p, miR-22-3p, miR-223-5p, miR-223-3p, miR-483-5p, miR-409-3p, miR-196b-5p, miR-192-5p, miR-146a-5p, miR-126-5p, hsa-miR-16-5p, hsa-miR-17-5p, hsa-miR-19a-3p, hsa-miR-19b-3p, hsa-miR-20a-5p, let-7a, let-7b, let-7c, let-7d, let-7e, let-7f, miR-200a, miR-200b, and/or miR-200c, or any combination thereof.

In some embodiments, the first mixture of nucleic acids comprises a plurality of microRNA nucleotide sequences, and each microRNA nucleotide sequence of the plurality is selected from the nucleotide sequences encoding hsa-miR-16-5p, hsa-miR-17-5p, hsa-miR-19a-3p, hsa-miR-19b-3p, hsa-miR-20a-5p, let-7a, let-7b, let-7c, let-7d, let-7e, let-7f, miR-1201-5p, miR-126-5p, miR-133b, miR-141, miR-146a-5p, miR-149-5p, miR-185, miR-192-5p, miR-196b-5p, miR-1973, miR-200a, miR-200b, miR-200c, miR-203-5p, miR-205, miR-21, miR-223-3p, miR-223-5p, miR-22-3p, miR-224-5p, miR-23b-5p, miR-27b-3p, miR-324a, miR-409-3p, miR-429, miR-452-5p, miR-483-5p, miR-494, miR-671-3p, and miR-944-5p. Thus, the first mixture of nucleic acids may comprise a plurality of microRNA nucleotide sequences, wherein the plurality comprises the nucleotide sequences of hsa-miR-16-5p, hsa-miR-17-5p, hsa-miR-19a-3p, hsa-miR-19b-3p, hsa-miR-20a-5p, let-7a, let-7h, let-7c, let-7d, let-7e, let-7f, miR-1201-5p, miR-126-5p, miR-133b, miR-141, miR-146a-5p, miR-149-5p, miR-185, miR-192-5p, miR-196b-5p, miR-1973, miR-200a, miR-200b, miR-200c, miR-203-5p, miR-205, miR-21, miR-223-3p, miR-223-5p, miR-22-3p, miR-224-5p, miR-23b-5p, miR-27b-3p, miR-324a, miR-409-3p, miR-429, miR-452-5p, miR-483-5p, miR-494, miR-671-3p, and/or miR-944-5p, or any combination thereof.

In some embodiments, the first mixture of nucleic acids comprises a plurality of microRNA nucleotide sequences, and each nucleotide sequence of the plurality is selected from a nucleotide sequence encoding a microRNA listed in the PhenomiR database (the World Wide Web at rnips.helmholtz-muenchen.de/phenomir/index.gsp), the microRNA.org database (the World Wide Web at microrna.org), or the miRBasc database (the World Wide Web at mirbase.org). In some embodiments, the first mixture of nucleic acids comprises a plurality of microRNA nucleotide sequences; the plurality of microRNA nucleotide sequences encodes 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56.

57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, or 600 different microRNAs; and each microRNA nucleotide sequence of the plurality is selected from a nucleotide sequence encoding a microRNA listed in the PhenomiR database, microRNA.org database, or the miRBase database.

In some embodiments, the upregulation or downregulation of a microRNA encoded by a nucleotide sequence is associated with a disease, such as cancer.

In some embodiments, the first mixture of nucleic acids comprises a plurality of microRNA nucleotide sequences, and each microRNA nucleotide sequence of the plurality is selected from a nucleotide sequence encoding hsa-mir-708, hsa-let-7a-1, hsa-let-7a-2, hsa-let-7a-3, hsa-let-7b, hsa-let-7c, hsa-let-7d, hsa-let-7e, hsa-let-7f-1, hsa-let-71-2, hsa-let-7g, hsa-let-7i, hsa-mir-100, hsa-mir-101-1, hsa-mir-103-1, hsa-mir-103-2, hsa-mir-106a, hsa-mir-106b, hsa-mir-107, hsa-mir-10a, hsa-mir-10b, hsa-mir-1-1, hsa-mir-122, hsa-mir-1226, hsa-mir-124-1, hsa-mir-124-2, hsa-mir-124-3, hsa-mir-125a, hsa-mir-125b-1, hsa-mir-125b-2, hsa-mir-126, hsa-mir-127, hsa-mir-128-1, hsa-mir-128-2, hsa-mir-129-1, hsa-mir-129-2, hsa-mir-130a, hsa-mir-130b, hsa-mir-132, hsa-mir-133a-1, hsa-mir-133b, hsa-mir-134, hsa-mir-135a-1, hsa-mir-135a-2, hsa-mir-135b, hsa-mir-136, hsa-mir-137, hsa-mir-138-1, hsa-mir-138-2, hsa-mir-139, hsa-mir-140, hsa-mir-141, hsa-mir-142, hsa-mir-143, hsa-mir-144, hsa-mir-145, hsa-mir-146a, hsa-mir-146b, hsa-mir-147, hsa-mir-148a, hsa-mir-148b, hsa-mir-149, hsa-mir-150, hsa-mir-151, hsa-mir-152, hsa-mir-153-1, hsa-mir-153-2, hsa-mir-154, hsa-mir-155, hsa-mir-15a, hsa-mir-15b, hsa-mir-16-1, hsa-mir-17, hsa-mir-181a-1, hsa-mir-181b-1, hsa-mir-181b-2, hsa-mir-181c, hsa-mir-182, hsa-mir-183, hsa-mir-184, hsa-mir-185, hsa-mir-186, hsa-mir-187, hsa-mir-188, hsa-mir-18a, hsa-mir-190, hsa-mir-191, hsa-mir-192, hsa-mir-193a, hsa-mir-193b, hsa-mir-194-1, hsa-mir-194-2, hsa-mir-195, hsa-mir-196a-1, hsa-mir-196a-2, hsa-mir-196b, hsa-mir-197, hsa-mir-198, hsa-mir-199a-1, hsa-mir-199a-2, hsa-mir-199b, hsa-mir-19a, hsa-mir-19b-1, hsa-mir-19b-2, hsa-mir-200a, hsa-mir-200b, hsa-mir-200c, hsa-mir-202, hsa-mir-203, hsa-mir-204, hsa-mir-205, hsa-mir-206, hsa-mir-208a, hsa-mir-20a, hsa-mir-21, hsa-mir-210, hsa-mir-211, hsa-mir-212, hsa-mir-214, hsa-mir-215, hsa-mir-216a, hsa-mir-217, hsa-mir-218-1, hsa-mir-218-2, hsa-mir-219-1, hsa-mir-219-2, hsa-mir-22, hsa-mir-221, hsa-mir-222, hsa-mir-223, hsa-mir-224, hsa-mir-23a, hsa-mir-23b, hsa-mir-24-1, hsa-mir-24-2, hsa-mir-25, hsa-mir-26a-1, hsa-mir-26a-2, hsa-mir-26b, hsa-mir-27a, hsa-mir-27b, hsa-mir-28, hsa-mir-296, hsa-mir-299, hsa-mir-29a, hsa-miR-29b, hsa-mir-29b-1, hsa-mir-29b-2, hsa-mir-29c, hsa-mir-301a, hsa-mir-302a, hsa-mir-302b, hsa-mir-302c, hsa-mir-302d, hsa-mir-30a, hsa-mir-30b, hsa-mir-30c-1, hsa-mir-30d, hsa-mir-30e, hsa-mir-31, hsa-mir-32, hsa-mir-320a, hsa-mir-323, hsa-mir-324, hsa-mir-325, hsa-mir-326, hsa-mir-328, hsa-mir-330, hsa-mir-331, hsa-mir-335, hsa-mir-337, hsa-mir-338, hsa-miR-338-3p, hsa-mir-339, hsa-mir-33a, hsa-mir-340, hsa-mir-342, hsa-mir-345, hsa-mir-346, hsa-mir-34a, hsa-mir-34b, hsa-mir-34c, hsa-mir-361, hsa-mir-365-1, hsa-mir-367, hsa-mir-369, hsa-mir-370, hsa-mir-371, hsa-mir-372, hsa-mir-373, hsa-mir-374a, hsa-mir-375, hsa-mir-376a-1, hsa-mir-376c, hsa-mir-377, hsa-mir-378, hsa-mir-379, hsa-mir-380, hsa-mir-381, hsa-mir-382, hsa-mir-383, hsa-mir-384, hsa-mir-409, hsa-mir-410, hsa-mir-411, hsa-mir-423, hsa-mir-424, hsa-mir-425, hsa-mir-432, hsa-mir-433, hsa-mir-449b, hsa-mir-451, hsa-mir-452, hsa-mir-485, hsa-mir-486, hsa-mir-487h, hsa-mir-494, hsa-mir-495, hsa-mir-497, hsa-mir-503, hsa-mir-505, hsa-mir-510, hsa-mir-513a-1, hsa-mir-518c, hsa-mir-520b, hsa-mir-520d, hsa-mir-542, hsa-mir-582, hsa-mir-601, hsa-mir-608, hsa-mir-622, hsa-mir-629, hsa-mir-630, hsa-mir-639, hsa-mir-644, hsa-mir-646, hsa-mir-649, hsa-mir-654, hsa-mir-663, hsa-mir-7-1, hsa-mir-7-2, hsa-mir-7-3, hsa-mir-765, hsa-mir-873, hsa-mir-877, hsa-mir-891a, hsa-mir-9-1, hsa-mir-9-2, hsa-mir-92a-1, hsa-mir-92a-2, hsa-mir-93, hsa-mir-9-3, hsa-mir-95, hsa-mir-96, hsa-mir-98, hsa-mir-99a, mmu-mir-100, mmu-mir-106a, mmu-mir-10a, mmu-mir-10b, mmu-mir-1-1, mmu-mir-125b-1, mmu-mir-130b, mmu-mir-133a-1, mmu-mir-133b, mmu-mir-139, mmu-mir-140, mmu-mir-150, mmu-mir-17, mmu-mir-181c, mmu-mir-184, mmu-mir-18a, mmu-mir-20a, mmu-mir-20b, mmu-mir-22, mmu-mir-223, mmu-mir-292, mmu-mir-296, mmu-mir-298, mmu-mir-29c, mmu-mir-301a, mmu-mir-346, mmu-mir-375, mmu-mir-466a, mmu-mir-500, mmu-mir-669a-1, mmu-mir-680-1, mmu-mir-686, mmu-mir-706, mmu-mir-711, mmu-mir-714, mmu-mir-7a-1, or mmu-mir-9-1, or mmu-mir-99a. For example, a plurality of microRNA nucleotide sequences may encode 2, 3, 4, 5, 6, 7, 8, 9, 10, 11, 12, 13, 14, 15, 16, 117, 18, 19, about 20, about 25, about 30, about 35, about 40, about 45, about 50, about 55, about 60, about 65, about 70, about 75, about 80, about 85, about 90, about 95, about 100, about 120, about 150, about 200, about 250, about 300, about 400, about 500, or about 600 of the foregoing. A plurality of microRNA nucleotide sequences may encode at least 2, 3, 4, 5, 6, 7, 8, 9, 10, 11, 12, 13, 14, 15, 16, 117, 18, 19, about 20, about 25, about 30, about 35, about 40, about 45, about 50, about 55, about 60, about 65, about 70, about 75, about 80, about 85, about 90, about 95, about 100, about 120, about 150, about 200, about 250, about 300, about 400, about 500, or about 600 of the foregoing.

Each nucleic acid of the first mixture of nucleic acids may comprise a barcode identifier as described herein, infra.

A Second Mixture of Nucleic Acids

A control may comprise a second mixture of nucleic acids. The first mixture of nucleic acids and the second mixture of nucleic acids may be admixed in the control. Each mixture of nucleic acids of a control may be admixed in the control.

The second mixture of nucleic acids may encode a second genotype that is different from the first genotype. In certain embodiments, the second mixture of nucleic acids encodes "normal" genotypes (i.e., genotypes that are not associated with disease) relative to the genotype(s) of interest. Thus, in some embodiments, the second mixture of nucleic acids does not encode an aneuploidy, a genotype associated with a hereditary disease, a genotype associated with a communicable disease, or a genotype associated with a neoplasm. Nevertheless, the second mixture of nucleic acids may encode an aneuploidy, a genotype associated with a hereditary disease, a genotype associated with a communicable disease, or a genotype associated with a neoplasm, so long as the genotype does not mask the genotype of interest associated with the first mixture of nucleic acids or otherwise confound the use of the control.

The second mixture of nucleic acids may comprise one or more pluralities of nucleotide sequences, which may encode one or more genotypes, e.g., one plurality of nucleotide sequences may encode one or more genotypes.

In some embodiments, the second mixture of nucleic acids comprises nucleotide sequences encoding substantially all of the genome of a cell, plurality of cells, cell line, or subject. For example, the cell line may be an immortalized lymphocyte cell line genome, a fibroblast cell line genome, or a cytotrophoblast cell line genome. In certain embodiments, the second mixture of nucleic acids comprises nucleotide sequences encoding substantially all of the genome of a human cell, human cell line, or human subject. The cell line may be, for example, GM24385. The second mixture of nucleic acids may be obtained from a cell, plurality of cells, cell line, or donor, e.g., a cell, plurality of cells, cell line, or donor that does not carry an aneuploidy, hereditary disease, provirus, and/or cancer mutation. For example, the second mixture of nucleic acids may be obtained from a human donor, e.g., from cells or bodily fluids of the human donor. The second mixture of nucleic acids may be obtained from peripheral blood mononuclear cells (PBMCs), lymphocytes, fibroblasts, placenta, and/or adipocytes of a human donor. In certain preferred embodiments, the second mixture of nucleic acids is obtained from PBMCs. The second mixture of nucleic acids may be obtained from the placenta of a human donor. The second mixture of nucleic acids may comprise cell free DNA obtained from a donor (e.g., human donor, such as a human female). The donor may be a healthy human donor (e.g., who does not have cancer). The cell free DNA may be obtained from blood plasma or blood serum. The control may further comprise blood plasma or blood serum such as human blood plasma or human blood serum. About 50% to 100% of the control may be blood plasma or blood serum, such as about 90% to 100%, about 90% to 99.999%, or about 95% to 99.99% (e.g., wherein the blood plasma or blood serum comprises cell-free DNA). The cell free DNA may be obtained from urine. In certain embodiments, the human donor may be male or female. In certain embodiments, the donor is female.

The second mixture of nucleic acids need not comprise nucleotide sequences that encode an entire genome. For example, a mixture of nucleic acids derived from a cell may encode substantially all of the genome of the cell even though some nucleotide sequences may have been lost during processing steps, such as during isolation and/or fragmentation steps. Similarly, the second mixture of nucleic acids may be enriched or depleted of various nucleotide sequences, e.g., for use in testing the robustness of an assay or diagnostic test. Alternatively, the second mixture of nucleic acids may originate from one or more non-human sources, such as a host cell comprising one or more nucleotide sequences sufficient to calibrate an assay or diagnostic test or to assess its performance. In some embodiments, the second mixture of nucleic acids encodes substantially all of the genome of a cell, cell line, or subject, e.g., a human cell, human cell line, or human subject. In other embodiments, the second mixture of nucleic acids does not encode the genome of a cell, cell line, or subject. The second mixture of nucleic acids may also comprise nucleotide sequences from human pathogens, e.g., the second mixture of nucleic acids may comprise viral, bacterial, protist, or fungal nucleotide sequences, wherein the virus, bacterium, protist, or fungus is a human pathogen.

The second mixture of nucleic acids may be substantially free of chromatin, nucleosomes, and/or histones, e.g., the second mixture of nucleic acids may comprise human nucleotide sequences that are substantially free of chromatin, nucleosomes, and histones. The second mixture of nucleic acids may be free of chromatin, nucleosomes, and/or histones. In some embodiments, the second mixture of nucleic acids comprises chromatin, nucleosomes, and/or histones. The second mixture of nucleic acids may comprise methylated nucleic acids or the second mixture of nucleic acids may be substantially free of methylated nucleic acids. The second mixture of nucleic acids may comprise double-stranded nucleic acids that comprise "sticky" ends, e.g., wherein a double-stranded nucleic acid comprises one or two 3' overhangs, one or two 5' overhangs, or a 3' overhang and a 5' overhang. The second mixture of nucleic acids may be substantially free from 3' and/or 5' overhangs. The second mixture of nucleic acids may consist essentially of blunt-ended nucleic acids. Substantially all of the 5' ends of the nucleic acids in the second mixture may be phosphorylated. In some embodiments, substantially all of the 5' ends of the nucleic acids in the second mixture are not phosphorylated. Substantially all of the 3' ends of the nucleic acids in the second mixture may be dephosphorylated. In some embodiments, substantially all of the 3' ends of the nucleic acids in the second mixture are phosphorylated. Dephosphorylating the 5' ends of the nucleic acids (and/or 3' ends) of a control may inhibit unintended ligation. Blunt-ending the nucleic acids of a control may inhibit unintended pairing and/or aggregation of nucleic acids. The second mixture of nucleic acids may comprise mitochondrial nucleotide sequences, or the second mixture of nucleic acids may be substantially free of mitochondrial nucleotide sequences. The second mixture of nucleic acids may comprise DNA and/or RNA. In some embodiments, the second mixture of nucleic acids is substantially free of RNA. In some embodiments, the second mixture of nucleic acids comprises RNA.

In some embodiments, the second mixture of nucleic acids comprises a plurality of nucleotide sequences, e.g., for embodiments in which the first mixture of nucleic acids comprises a plurality of nucleotide sequences. In certain embodiments, the second mixture of nucleic acids comprises a first nucleotide sequence that is related to the first nucleotide sequence of the first mixture of nucleic acids. For example, in embodiments in which the genotype of interest is aneuploidy, the first nucleotide sequence of the second mixture of nucleic acids may be identical to the first nucleotide sequence of the first mixture of nucleic acids. Similarly, in embodiments in which the genotype of interest is associated with a hereditary disease, the first nucleotide sequence of the second mixture of nucleic acids may encode a healthy or normal genotype, which is related to but varies from the first nucleotide sequence of the first mixture of nucleic acids, which encodes the disease genotype. Further, in embodiments in which the genotype of interest is associated with a neoplasm, the first nucleotide sequence of the second mixture of nucleic acids may encode a healthy or normal genotype, which is related to but varies from the first nucleotide sequence of the first mixture of nucleic acids, which may encode a disease genotype.

The second mixture of nucleic acids may comprise a second nucleotide sequence. In certain embodiments, the second nucleotide sequence is related to or identical to the second nucleotide sequence of the first mixture of nucleic acids. The second nucleotide sequence may have sequence homology to a different nucleotide sequence than the first nucleotide sequence. For example, the first nucleotide sequence may have sequence homology with a first chromosome, the second nucleotide sequence may have sequence homology with a second chromosome, and the ratio of the copy number of the first nucleotide sequence to the copy number of the second nucleotide sequence may be about 1:1 in the second mixture of nucleic acids, e.g., when the first mixture of nucleic acids comprises the first nucleotide sequence and the second nucleotide sequence in a different ratio for use as an aneuploidy control. Thus, the first nucleotide sequence may have sequence homology to any one of chromosomes 8, 9, 13, 18, 21, 22, or X, of which trisomy may result in a viable fetus, and the second nucleotide sequence may have sequence homology with a different chromosome, e.g., a different chromosome that is an autosome, such as chromosome 1, 6, or 7, which are commonly used as reference chromosomes. Nevertheless, even though other trisomic chromosomes are not known to result in viable offspring, the first nucleotide sequence may have sequence homology to any one of chromosomes 1, 2, 3, 4, 5, 6, 7, 8, 9, 10, 11, 12, 13, 14, 15, 16, 17, 18, 19, 20, 21, 22, X, or Y, e.g., in order to calibrate a diagnostic test or to screen for a trisomy in a fetus before the trisomy displays a lethal phenotype. Similarly, the ratio of the copy number of the first nucleotide sequence to the copy number of the second nucleotide sequence may vary from about 1:1 in the second mixture of nucleic acids, e.g., for use in determining the ploidy of a sex chromosome. For example, in some embodiments, the first nucleotide sequence may have sequence homology to chromosome Y, the second nucleotide sequence may have sequence homology with an autosome, and the ratio of the copy number of the first nucleotide sequence to the copy number of the second nucleotide sequence may be about 1:2 in the second mixture of nucleic acids.

The second mixture of nucleic acids may comprise a third nucleotide sequence, e.g., for use in determining whether a fetus has Klinefelter syndrome. In this embodiment, the first nucleotide sequence may have sequence homology with human chromosome X; a second nucleotide sequence may have sequence homology with an autosome; a third nucleotide sequence may have sequence homology with chromosome Y; and the ratio of the copy numbers of the first, second, and third nucleotide sequences may be about 1:2:1 in the second mixture of nucleic acids, e.g., when the first mixture of nucleic acids comprises the first, second, and third nucleotide sequences in a ratio of about 2:2:1.

In some embodiments, the second mixture of nucleic acids comprises a first plurality of nucleotide sequences and a second plurality of nucleotide sequences, e.g., for embodiments in which the first mixture of nucleic acids comprises a first plurality of nucleotide sequences and a second plurality of nucleotide sequences. In certain embodiments, the first plurality of nucleotide sequences of the second mixture of nucleic acids is related to the first plurality of nucleotide sequences of the first mixture of nucleic acids. For example, in embodiments in which the genotype of interest is aneuploidy, the first plurality of nucleotide sequences of the second mixture may be identical to (or have sequence homology with) the first plurality of nucleotide sequences of the first mixture. Similarly, in embodiments in which the genotype of interest is associated with a hereditary disease, the first plurality of nucleotide sequences of the second mixture may comprise a nucleotide sequence that encodes a healthy or normal genotype, which is related to but varies from a nucleotide sequence of the first plurality of nucleotide sequences of the first mixture, which may encode a disease genotype from the same genetic locus as the nucleotide sequence of the second mixture. Further, in embodiments in which the genotype of interest is associated with a neoplasm, the first plurality of nucleotide sequences of the second mixture may comprise a nucleotide sequence that encodes a healthy or normal genotype, which is related to but varies from a nucleotide sequence of the first plurality of nucleotide sequences of the first mixture, which may encode a disease genotype from the same genetic locus as the nucleotide sequence of the second mixture.

In certain embodiments, the second plurality of nucleotide sequences of the second mixture of nucleic acids is related to or identical to the second plurality of nucleotide sequences of the first mixture of nucleic acids. The second plurality of nucleotide sequences of the second mixture may have sequence homology to different nucleotide sequences than the first plurality of nucleotide sequences of the second mixture. For example, the first plurality of nucleotide sequences may have sequence homology with a first chromosome, the second plurality of nucleotide sequences may have sequence homology with a second chromosome, and the ratio of the copy number of any nucleotide sequence of the first plurality to the copy number of any nucleotide sequence in the second plurality may be about 1:1 in the second mixture of nucleic acids, e.g., when the first mixture of nucleic acids comprises copy numbers for a first nucleotide sequence and second nucleotide sequence in a different ratio for use as an aneuploidy control. Thus, each nucleotide sequence of the first plurality may have sequence homology to any one of chromosomes 8, 9, 13, 18, 21, 22, or X, of which trisomy may result in a viable fetus, and each nucleotide sequence of the second plurality may have sequence homology with a different chromosome, e.g., a different chromosome that is an autosome. Nevertheless, even though other trisomic chromosomes are not known to result in viable offspring, each nucleotide sequence of the first plurality may have sequence homology to any one of chromosomes 1, 2, 3, 4, 5, 6, 7, 8, 9, 10, 11, 12, 13, 14, 15, 16, 17, 18, 19, 20, 21, 22, X, or Y, e.g., in order to calibrate a diagnostic test or to screen for a trisomy in a fetus before the trisomy displays a lethal phenotype. Similarly, the ratio of the copy number of any nucleotide sequence of the first plurality to the copy number of any nucleotide sequence of the second plurality may vary from about 1:1 in the second mixture of nucleic acids, e.g., for use in determining the ploidy of a sex chromosome. For example, in some embodiments, each nucleotide sequence of the first plurality may have sequence homology to chromosome Y, each nucleotide sequence of the second plurality may have sequence homology with an autosome, and the ratio of the copy number of any nucleotide sequence of the first plurality to the copy number of any nucleotide sequence of the second plurality may be about 1:2 in the second mixture of nucleic acids.

The second mixture of nucleic acids may comprise nucleotide sequences that have sequence homology with the first chromosome that are not included in the first plurality of nucleotide sequences. Similarly, the second mixture of nucleic acids may comprise nucleotide sequences that have sequence homology with the second chromosome that are not included in the second plurality of nucleotide sequences.

The second mixture of nucleic acids may comprise a third plurality of nucleotide sequences, e.g., for use in determining whether a fetus has Klinefelter syndrome. In this embodiment, each nucleotide sequence of the first plurality may have sequence homology with human chromosome X; each nucleotide sequence of the second plurality may have sequence homology with an autosome; each nucleotide sequence of the third plurality may have sequence homology with chromosome Y; and the ratio of the copy numbers of any three nucleotide sequences selected from the first, second, and third pluralities may be about 1:2:1.

The second mixture of nucleic acids may comprise a first plurality of nucleotide sequences, a second plurality of nucleotide sequences, a third plurality of nucleotide sequences, and a fourth plurality of nucleotide sequences, e.g., when the first mixture of nucleic acids comprises a first plurality of nucleotide sequences, a second plurality of nucleotide sequences, a third plurality of nucleotide sequences, and a fourth plurality of nucleotide sequences. Each nucleotide sequence of the first plurality of nucleotide sequences may have sequence homology to chromosome 13, each nucleotide sequence of the second plurality of nucleotide sequences may have sequence homology to chromosome 18, and each nucleotide sequence of the third plurality of nucleotide sequences may have sequence homology to chromosome 21. Each nucleotide sequence of the fourth plurality of nucleotide sequences may have sequence homology to chromosome 1, 2, 3, 4, 5, 6, 7, 8, 9, 10, 11, 12, 14, 15, 16, 17, 19, 20, or 22, preferably chromosome 1, 6, or 7. The ratio of the copy number of any nucleotide sequence selected from the first, second, and third pluralities to the copy number of any nucleotide sequence selected from the fourth plurality may be about 1:1 in the second mixture, e.g., wherein the ratio is about 7:6 in the first mixture.

A first plurality of nucleotide sequences of a first mixture and a first plurality of nucleotide sequences of a second mixture may consist of the same nucleotide sequences. A second plurality of nucleotide sequences of a first mixture and a second plurality of nucleotide sequences of a second mixture may consist of the same nucleotide sequences. A third plurality of nucleotide sequences of a first mixture and a third plurality of nucleotide sequences of a second mixture may consist of the same nucleotide sequences. A fourth plurality of nucleotide sequences of a first mixture and a fourth plurality of nucleotide sequences of a second mixture may consist of the same nucleotide sequences.

The first mixture of nucleic acids may comprise a nucleotide sequence that encodes a mutation or genotype that is associated with cancer, and the second mixture of nucleic acids may comprise a nucleotide sequence that encodes a normal or wild type genotype corresponding to the mutation or genotype of the first mixture. The first mixture of nucleic acids may comprise a plurality of nucleotide sequences, wherein each nucleotide sequence of the plurality encodes a genotype (or mutation) that is associated with cancer, and the second mixture of nucleic acids may comprise a plurality of nucleotide sequences, wherein each nucleotide sequence of the plurality encodes a wild type genotype corresponding to a genotype (or mutation) that is associated with cancer in the first mixture.

The first mixture of nucleic acids may comprise a nucleotide sequence that encodes a mutation or genotype that is associated with cancer, and the second mixture of nucleic acids may encode substantially all of a human genome, wherein the human genome does not comprise the mutation or genotype. The first mixture of nucleic acids may comprise a plurality of nucleotide sequences, wherein each nucleotide sequence of the plurality encodes a genotype (or mutation) that is associated with cancer, and the second mixture of nucleic acids may encode substantially all of a human genome, wherein the human genome does not comprise the mutations or genotypes of the plurality.

In some embodiments, the first mixture of nucleic acids comprises a nucleotide sequence that encodes a genotype listed in the COSMIC database, and the second mixture of nucleic acids comprises a nucleotide sequence that encodes a wild type genotype corresponding to the genotype listed in the COSMIC database. In some embodiments, the first mixture of nucleic acids comprises a first plurality of nucleotide sequences, wherein each nucleotide sequence of the first plurality encodes a genotype listed in the COSMIC database, and the second mixture of nucleic acids comprises a second plurality of nucleotide sequences encoding wild type genotypes corresponding to each genotype of the first plurality. For example, the first mixture of nucleic acids may comprise a first plurality of nucleotide sequences, wherein the first plurality of nucleotide sequences encodes 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 genotypes listed in the COSMIC database, and the second mixture of nucleic acids may comprise a second plurality of nucleotide sequences encoding wild type genotypes corresponding to each genotype in the first plurality. The first mixture of nucleic acids may comprise a first plurality of nucleotide sequences, wherein the first plurality of nucleotide sequences encodes at least 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 genotypes listed in the COSMIC database, and the second mixture of nucleic acids may comprise a second plurality of nucleotide sequences encoding wild type genotypes corresponding to each genotype in the first plurality. In some embodiments, the first mixture of nucleic acids comprises a nucleotide sequence that encodes a genotype listed in the COSMIC database, and the second mixture of nucleic acids encodes substantially all of a human genome, wherein the human genome does not comprise the genotype. In some embodiments, the first mixture of nucleic acids comprises a first plurality of nucleotide sequences, wherein each nucleotide sequence of the first plurality encodes a genotype listed in the COSMIC database, and the second mixture of nucleic acids encodes substantially all of a human genome, wherein the human genome does not comprise the genotypes of the first plurality.

Similarly, the first mixture of nucleic acids may comprise a first plurality of nucleotide sequences, wherein each nucleotide sequence of the first plurality encodes a genotype listed in the Table 1, and the second mixture of nucleic acids may comprise a second plurality of nucleotide sequences encoding wild type genotypes corresponding to each genotype in the first plurality. For example, the first mixture of nucleic acids may comprise a first plurality of nucleotide sequences, wherein the first plurality of nucleotide sequences encodes 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66 genotypes listed in Table 1, and the second mixture of nucleic acids may comprise a second plurality of nucleotide sequences encoding wild type genotypes corresponding to each genotype in the first plurality. In some embodiments, the first mixture of nucleic acids comprises a first nucleotide sequence encoding a portion of a gene (and/or a regulatory region thereof) comprising a mutation, wherein the gene is selected from MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RBI, PARP2, ARHGAP5, AKT1, RAD51, IDH2, TP53, NF1, SMAD4, AKT2, ERCC1, and GNAS, and the second mixture of nucleic acids comprises a second nucleotide sequence encoding the portion of the gene, but comprising a wild type sequence. In some embodiments, the first mixture of nucleic acids comprises a first plurality of nucleotide sequences, wherein each nucleotide sequence of the first plurality encodes a portion of a gene (and/or a regulatory region thereof) comprising a mutation, and the genes are selected from MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RBI, PARP2, ARHGAP5, AKT1, RAD51, IDH2, TP53, NF1, SMAD4, AKT2, ERCC1, and GNAS, and the second mixture of nucleic acids comprises a second plurality of nucleotide sequences, wherein the second plurality of nucleotide sequences encodes the portion of each gene, but comprising a wild type sequence for each gene. In some embodiments, the first mixture of nucleic acids comprises a plurality of nucleotide sequences, wherein each nucleotide sequence of the plurality encodes a portion of a gene (and/or a regulatory region thereof) comprising a mutation, the nucleotide sequences of the plurality encode portions of 1, 2, 3, 4, 5, 6, 7, 8, 9, 10, 11, 12, 13, 14, 15, 16, 17, 18, 19, 20, 1, 22, 23, 24, 25, 26, 27, 28, 29, 30, 31, 32, 33, 34, 35, 36, 37, 38, 39, 40, 41, 42, 43, or 44 different genes, and the genes are selected from MTOR, MPL, NRAS, PARP1, AKT3, DNMT3A, MSH2, IDH1, VHL, MLH1, MYD88, CTNNB1, ATR, PIK3CA, FGFR3, PDGFRA, KIT, FBXW7, APC, GABRG2, NPM1, EGFR, MET, BRAF, EZH2, JAK2, GNAQ, RET, PTEN, ATM, KRAS, PTPN11, FLT3, RB1, PARP2, ARHGAP5, AKT1, RAD51, IDH2, TP53, NF1, SMAD4, AKT2, ERCC1, and GNAS, and the second mixture of nucleic acids comprises a second plurality of nucleotide sequences, wherein the second plurality of nucleotide sequences encodes the portion of each gene, but comprising a wild type sequence for each gene. The first mixture of nucleic acids may comprise a first plurality of nucleotide sequences, wherein each nucleotide sequence of the first plurality encodes a genotype listed in the Table 1, and the second mixture of nucleic acids may encode substantially all of a human genome, wherein the human genome does not comprise the genotypes of the first plurality.

In some embodiments, the first mixture of nucleic acids comprises a first nucleotide sequence encoding a portion of a gene (and/or a regulatory region thereof) comprising a mutation, wherein the gene is selected from AKT1, ATM, BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA, PTEN, RET, and STK11, and the second mixture of nucleic acids comprises a second nucleotide sequence comprising the portion of the gene, but comprising a wild type sequence. In some embodiments, the first mixture of nucleic acids comprises a first plurality of nucleotide sequences, wherein each nucleotide sequence of the first plurality encodes a portion of a gene (and/or a regulatory region thereof) comprising a mutation, and the genes are selected from AKT1, ATM. BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA PTEN, RET, and STK11, and the second mixture of nucleic acids comprises a second plurality of nucleotide sequences, wherein the second plurality of nucleotide sequences encodes the portion of each gene, but comprising a wild type sequence for each gene. In some embodiments, the first mixture of nucleic acids comprises a first plurality of nucleotide sequences, wherein each nucleotide sequence of the first plurality encodes a portion of a gene (and/or a regulatory region thereof) comprising a mutation, the nucleotide sequences of the plurality encode portions of 1, 2, 3, 4, 5, 6, 7, 8, 9, 10, 11, 12, 13, 14, 15, 16, 17, 18, 19, 20, 1, 22, 23, 24, 25, or 26 different genes, and the genes are selected from AKT1, ATM, BRAF, CDKN2A, CSF1R, EGFR, ERBB2 ("HER2"), ERBB4 ("HER4"), FGFR1, FGFR2, FGFR3, GNA11, HRAS, JAK2, JAK3, KDR, KIT, KRAS, MET, NOTCH1, NRAS, PDGFRA, PIK3CA, PTEN, RET, and STK11, and the second mixture of nucleic acids comprises a second plurality of nucleotide sequences, wherein the second plurality of nucleotide sequences encodes the portion of each gene, but comprising a wild type sequence for each gene. For example, the second plurality of nucleotide sequences may encode substantially all of a human genome, wherein the human genome does not comprise the mutations of the first plurality.

First and Second Mixtures of Nucleic Acids

In some embodiments, the control comprises a first mixture of nucleic acids encoding a first genotype and a second mixture of nucleic acids encoding a second genotype, and the ratio of the copy number of each nucleotide sequence that encodes the first genotype to the copy number of each nucleotide sequence that encodes the second genotype is about 1:1000 to 1000:1, such as about 1:100 to about 100:1, about 1:50 to about 50:1, about 1:40 to about 40:1, about 1:30 to about 30:1, about 1:20 to about 20:1, about 1:15 to about 15:1, about 1:10 to about 10:1, about 1:9 to about 9:1, about 1:8 to about 8:1, about 1:7 to about 7:1, about 1:6 to about 6:1, about 1:5 to about 5:1, about 1:4, to about 4:1, about 1:3 to about 3:1, about 1:2 to about 2:1; about 1:1000 to 1:1, such as about 1:100 to about 1:1, about 1:50 to about 1:1, about 1:40 to about 1:1, about 1:30 to about 1:1, about 1:20 to about 1:1, about 1:15 to about 1:1, about 1:10 to about 1:1, about 1:9 to about 1:1, about 1:8 to about 1:1, about 1:7 to about 1:1, about 1:6 to about 1:1, about 1:5 to about 1:1, about 1:4, to about 1:1, about 1:3 to about 1:1, or about 1:2 to about 1:1. In some embodiments, the ratio of the copy number of each nucleotide sequence that encodes the first genotype to the copy number of each nucleotide sequence that encodes the second genotype is about 1:200 to about 1:2, such as about 1:200 to about 1:3, about 1:100 to about 1:2, about 1:100 to about 1:3, about 1:50 to about 1:2, about 1:50 to about 1:3, about 1:33 to about 1:2, about 1:33 to about 1:3, about 1:20 to about 1:2, or about 1:20 to about 1:3. In some embodiments, the ratio of the copy number of each nucleotide sequence that encodes the first genotype to the copy number of each nucleotide sequence that encodes the second genotype is about 1:1000, 1:100, 1:50, 1:40, 1:30, 1:20, 1:15, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, 20:1, 30:1, 40:1, 50:1, 100:1, or 1000:1.

In some embodiments, the control comprises a first mixture of nucleic acids comprising a plurality of nucleotide sequences encoding a first genotype and a second mixture of nucleic acids comprising a plurality of nucleotide sequences encoding a second genotype, and the ratio of the copy number of each nucleotide sequence of the plurality encoding the first genotype to the copy number of each nucleotide sequence of the plurality encoding the second genotype is about 1:1000 to 1000:1, such as about 1:100 to about 100:1, about 1:50 to about 50:1, about 1:40 to about 40:1, about 1:30 to about 30:1, about 1:20 to about 20:1, about 1:15 to about 15:1, about 1:10 to about 10:1, about 1:9 to about 9:1, about 1:8 to about 8:1, about 1:7 to about 7:1, about 1:6 to about 6:1, about 1:5 to about 5:1, about 1:4, to about 4:1, about 1:3 to about 3:1, about 1:2 to about 2:1; about 1:1000 to 1:1, such as about 1:100 to about 1:1, about 1:50 to about 1:1, about 1:40 to about 1:1, about 1:30 to about 1:1, about 1:20 to about 1:1, about 1:15 to about 1:1, about 1:10 to about 1:1, about 1:9 to about 1:1, about 1:8 to about 1:1, about 1:7 to about 1:1, about 1:6 to about 1:1, about 1:5 to about 1:1, about 1:4, to about 1:1, about 1:3 to about 1:1, or about 1:2 to about 1:1. In some embodiments, the ratio of the copy number of each nucleotide sequences of the plurality encoding the first genotype to the copy number of each nucleotide sequence of the plurality encoding the second genotype is about 1:200 to about 1:2, such as about 1:200 to about 1:3, about 1:100 to about 1:2, about 1:100 to about 1:3, about 1:50 to about 1:2, about 1:50 to about 1:3, about 1:33 to about 1:2, about 1:33 to about 1:3, about 1:20 to about 1:2, or about 1:20 to about 1:3. In some embodiments, the ratio of the copy number of each nucleotide sequences of the plurality encoding the first genotype to the copy number of each nucleotide sequence of the plurality encoding the second genotype is about 1:1000, 1:100, 1:50, 1:40, 1:30, 1:20, 1:15, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, 20:1, 30:1, 40:1, 50:1, 100:1, or 1000:1.

In some embodiments, the concentration of nucleic acids in the control is about 100 pg/mL to about 1 mg/mL, such as about 500 pg/mL to about 500 ng/mL, about 1 ng/mL to about 400 ng/mL, about 1 ng/mL to about 200 ng/mL, about 1 ng/mL to about 100 ng/mL, about 1 ng/mL to about 10 ng/mL, about 5 ng/mL to about 15 ng/mL, about 10 ng/mL to about 20 ng/mL, about 15 ng/mL to about 25 ng/mL, about 20 ng/mL to about 30 ng/mL, about 25 ng/mL to about 35 ng/mL, about 30 ng/mL to about 40 ng/mL, about 35 ng/mL to about 45 ng/mL, about 40 ng/mL to about 50 ng/mL, about 45 ng/mL to about 55 ng/mL, about 50 ng/mL to about 60 ng/mL, about 55 ng/mL to about 65 ng/mL, about 60 ng/mL to about 70 ng/mL, about 65 ng/mL to about 75 ng/mL, about 70 ng/mL to about 80 ng/mL, about 75 ng/mL to about 85 ng/mL, about 80 ng/mL to about 90 ng/mL, about 85 ng/mL to about 95 ng/mL, or about 90 ng/mL to about 100 ng/mL. In some embodiments, the concentration of nucleic acids in the control is about 5 ng/mL to about 50 ng/mL, such as about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL. In some embodiments, the concentration of nucleic acids in the control is about 20 ng/mL to about 40 ng/mL.

In some embodiments, the nucleic acids in the first mixture make up about 0%, 0.1%, 0.5%, 0.63%, 1%, 1.25%, 2%, 2.5%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 50%, 55%, 60%, 65%, 70%, 75%, 80%, 83%, 85%, 88%, 90%, 91%, 92%, 93%, 94%, 95%, 96%, 97%, 98%, 99%, or 100% of the total concentration of nucleic acids in the control. In some embodiments, the nucleic acids in the first mixture make up about 0% to about 10%, about 5% to about 15%, about 10% to about 20%, about 15% to about 25%, about 20% to about 30%, about 25% to about 35%, about 30% to about 40%, about 35% to about 45%, about 40% to about 50%, about 45% to about 55%, about 50% to about 60%, about 55% to about 65%, about 60% to about 70%, about 65% to about 75%, about 70% to about 80%, about 75% to about 85%, about 80% to about 90%, about 85% to about 95%, or about 90% to about 100% of the total concentration of nucleic acids in the control.

In some embodiments, the nucleic acids in the second mixture make up about 0%, 0.1%, 0.5%, 0.63%, 1%, 1.25%, 2%, 2.5%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 50%, 55%, 60%, 65%, 70%, 75%, 80%, 83%, 85%, 88%, 90%, 91%, 92%, 93%, 94%, 95%, 96%, 97%, 98%, 99%, or 100% of the total concentration of nucleic acids in the control. In some embodiments, the nucleic acids in the second mixture make up about 0% to about 10%, about 5% to about 15%, about 10% to about 20%, about 15% to about 25%, about 20% to about 30%, about 25% to about 35%, about 30% to about 40%, about 35% to about 45%, about 40% to about 50%, about 45% to about 55%, about 50% to about 60%, about 55% to about 65%, about 60% to about 70%, about 65% to about 75%, about 70% to about 80%, about 75% to about 85%, about 80% to about 90%, about 85% to about 95%, or about 90% to about 100% of the total concentration of nucleic acids in the control.

In some embodiments, the average length or median length of the nucleic acids in the control is about 20 to about 10,000 nucleotides, such as about 35 to about 1000 nucleotides, about 50 to about 900 nucleotides, about 50 to about 800 nucleotides, about 50 to about 700 nucleotides, about 50 to about 600 nucleotides, about 50 to about 500 nucleotides, about 50 to about 400 nucleotides, or about 50 to about 300 nucleotides. In some embodiments, the average length or median length of the nucleic acids in the control is about 50 to about 350 nucleotides, such as about 100 to about 300 nucleotides. The average length or median length of the nucleic acids in the control may be about 100 nucleotides, about 110 nucleotides, about 120 nucleotides, about 130 nucleotides, about 140 nucleotides, about 150 nucleotides, about 160 nucleotides, about 170 nucleotides, about 180 nucleotides, about 190 nucleotides, about 200 nucleotides, about 210 nucleotides, about 220 nucleotides, about 230 nucleotides, about 240 nucleotides, about 250 nucleotides, about 260 nucleotides, about 270 nucleotides, about 280 nucleotides, about 290 nucleotides, or about 300 nucleotides.

In some embodiments, the average length or median length of the nucleic acids in the first mixture of nucleic acids is about 20 to about 10,000 nucleotides, such as about 35 to about 1000 nucleotides, about 50 to about 900 nucleotides, about 50 to about 800 nucleotides, about 50 to about 700 nucleotides, about 50 to about 600 nucleotides, about 50 to about 500 nucleotides, about 50 to about 400 nucleotides, or about 50 to about 300 nucleotides. In some embodiments, the average length or median length of the nucleic acids in the first mixture of nucleic acids is about 50 to about 350 nucleotides, such as about 100 to about 300 nucleotides. The average length or median length of the nucleic acids in the first mixture of nucleic acids may be about 100 nucleotides, about 110 nucleotides, about 120 nucleotides, about 130 nucleotides, about 140 nucleotides, about 150 nucleotides, about 160 nucleotides, about 170 nucleotides, about 180 nucleotides, about 190 nucleotides, about 200 nucleotides, about 210 nucleotides, about 220 nucleotides, about 230 nucleotides, about 240 nucleotides, about 250 nucleotides, about 260 nucleotides, about 270 nucleotides, about 280 nucleotides, about 290 nucleotides, or about 300 nucleotides. In some embodiments, the average length or median length of the nucleic acids in the first mixture of nucleic acids is about 8 to about 1000 nucleotides, such as about 10 to about 800 nucleotides, about 12 to about 600 nucleotides, about 14 to about 400 nucleotides, about 15 to about 500 nucleotides, about 16 to about 400 nucleotides, about 17 to about 300 nucleotides, about 18 to about 200 nucleotides, about 19 to about 100 nucleotides, or about 20 to about 50 nucleotides. The average length or median length of the nucleic acids in the first mixture of nucleic acids may be about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, or about 30 nucleotides.

In some embodiments, the average length or median length of the nucleic acids in the second mixture of nucleic acids is about 20 to about 10,000 nucleotides, such as about 35 to about 1000 nucleotides, about 50 to about 900 nucleotides, about 50 to about 800 nucleotides, about 50 to about 700 nucleotides, about 50 to about 600 nucleotides, about 50 to about 500 nucleotides, about 50 to about 400 nucleotides, or about 50 to about 300 nucleotides. In some embodiments, the average length or median length of the nucleic acids in the second mixture of nucleic acids is about 50 to about 350 nucleotides, such as about 100 to about 300 nucleotides. The average length or median length of the nucleic acids in the second mixture of nucleic acids may be about 100 nucleotides, about 110 nucleotides, about 120 nucleotides, about 130 nucleotides, about 140 nucleotides, about 150 nucleotides, about 160 nucleotides, about 170 nucleotides, about 180 nucleotides, about 190 nucleotides, about 200 nucleotides, about 210 nucleotides, about 220 nucleotides, about 230 nucleotides, about 240 nucleotides, about 250 nucleotides, about 260 nucleotides, about 270 nucleotides, about 280 nucleotides, about 290 nucleotides, or about 300 nucleotides.

The length of the nucleic acids in the first mixture, second mixture, or control may be selected, for example, using SPRI beads (AmPure), gel electrophoresis, size-exclusion chromatography, anion exchange chromatography, and/or HPLC, e.g., prior to combining the nucleic acids with liposomes.

II. Internal Controls

In some aspects, the invention relates to an internal control, wherein the internal control is a nucleic acid comprising a barcode identifier, and the barcode identifier is a nucleotide sequence that does not have sequence homology with any human nucleotide sequence.

The barcode identifier may have less than 95%, 90%, 80%, 70%, 60%, 50%, or even less than 40% sequence identity with any known human nucleotide sequence. The barcode identifier may be 6 to about 30 nucleotides long, such as 6 to about 25, 6 to about 20, 6 to about 15, about 10 to about 30, about 10 to about 25, about 10 to about 20, or about 10 to about 15 nucleotides long. The barcode identifier may be 6, 7, 8, 9, 10, 11, 12, 13, 14, 15, 16, 17, 18, 19, 20, 21, 22, 23, 24, 25, 26, 27, 28, 29, or about 30 nucleotides long.

The internal control may be about 50 to about 500 nucleotides long, such as about 100 to about 300, about 100 to about 250, about 150 to about 300, about 150 to about 250, about 100 to about 200, about 120 to about 220, about 150 to about 220, or about 150 to about 200 nucleotides long.

The internal control may comprise a nucleotide sequence that has sequence homology to a human nucleotide sequence. The nucleotide sequence that has sequence homology to a human nucleotide sequence may be about 35 to about 600 nucleotides long, such as about 35 to about 300, about 50 to about 300, about 100 to about 250, about 100 to about 200, or about 150 to about 200 nucleotides long. The barcode may be 6 to about 20 nucleotides long; the nucleotide sequence that has sequence homology to a human nucleotide sequence may be about 150 to about 200 nucleotides long; and/or the internal control may be about 156 to about 220 nucleotides long.

The nucleotide sequence that has sequence homology to a human nucleotide sequence may comprise at least one single nucleotide variant relative to the human nucleotide sequence. The at least one single nucleotide variant may comprise a single nucleotide variant that is not known to occur in humans. The at least one single nucleotide variant may comprise a single nucleotide variant that is a dominant lethal allele. The at least one single nucleotide variant may comprise a single nucleotide variant that has never been observed in humans. The at least one single nucleotide variant may comprise a single nucleotide variant that is known to occur humans. The at least one single nucleotide variant may comprise a single nucleotide variant that is not a known dominant lethal allele.

In some aspects, the invention relates to a composition comprising an internal control. The composition may comprise a plurality of internal controls. For example, a composition may comprise 1, 2, 3, 4, 5, 6, 7, 8, 9, 10, 11, 12, 13, 14, 15, 16, 17, 18, 19, or 20 internal controls. Each internal control of a plurality of internal controls may comprise the same barcode or each internal control may comprise a different barcode. Each internal control of a plurality of internal controls may comprise a different nucleotide sequence that has sequence homology to a human nucleotide sequence, i.e., each internal control may comprise a nucleotide sequence that has sequence homology to a different human nucleotide sequence than the other internal controls of the plurality. The composition may further comprise liposomes.

A plurality of internal controls may comprise a first plurality of nucleotide sequences as described herein, supra, wherein each nucleotide sequence of the first plurality encodes either a portion of a gene (and/or a regulatory region thereof) comprising a mutation or a mutation or genotype that is associated with cancer or a hereditary disease. Each internal control may comprise a different nucleotide sequence of the first plurality of nucleotide sequences.

In some aspects, the invention relates to a sample comprising nucleic acids obtained from a human subject and an internal control (or a plurality of internal controls). The average length of the nucleic acids in the sample may be about 35 to about 600 nucleotides, such as about 50 to about 500 nucleotides, about 100 to about 400, about 125 to about 300, or about 150 to about 200 nucleotides. The nucleic acids may encode substantially all of the genome of the human subject. The sample may further comprise liposomes. In some aspects, the invention relates to a method of spiking a human sample with an internal control, comprising combining a human sample comprising nucleic acids with an internal control (or a composition comprising a plurality of internal controls).

In some aspects, the invention relates to a method of analyzing the nucleic acids in a human sample, comprising combining the human sample with an internal control (or a composition comprising a plurality of internal controls) and analyzing the sample. The human sample may comprise nucleic acids that encode substantially all of a human genome. The method may further comprise combining the human sample with liposomes before, after, or simultaneously with combining the human sample with the internal control (or composition). The method may comprise combining the human sample with a composition comprising the internal control and liposomes. The method may comprise analyzing the sample by quantitative PCR or next generation sequencing.

III. Liposomes

In some embodiments, the control comprises liposomes. The control may comprise a liposome selected from a multilamellar vesicle, a small unilamellar vesicle, a large unilamellar vesicle, and a cochleate vesicle. In some embodiments, the liposome comprises a unilamellar vesicle. In certain embodiments, a liposome encapsulates an aqueous solution. e.g., the liposome may define an aqueous compartment, which may comprise one or more nucleic acids of a control. In certain embodiments, the liposome comprises a bilayer. In some embodiments, the liposomes are unilamellar vesicles. Methods of making compositions comprising liposomes and nucleic acids wherein the nucleic acids are associated with the liposomes are known (see, e.g., US Patent Publication No. 2015/0147815 (hereby incorporated by reference in its entirety); Shim, G. et al., Asian J Pharmaceutical Sciences 8:72 (2013); Berg, E. S. and K. Skaug, J. Microbiological Methods 55:303 (2003); Monnard, P.-A., et al., Biochimica et Biophysica Acta 1329:39 (1997).

In some embodiments, the liposomes are artificial.

In some embodiments, the liposomes are derived from a cell. The liposomes may comprise microvesicles of cellular origin, extracellular vesicles, shedding vesicles, exovesicles, exosomes, ectosomes, oncosomes, and/or apoptotic bodies. The liposomes may be derived from cellular lipids. In some embodiments, the liposomes are not derived from cells or cellular lipids.

The liposomes may comprise proteins, such as transmembrane proteins or glycoproteins. In some embodiments, the liposomes are substantially free of protein. In some embodiments, the liposomes are substantially free of transmembrane proteins. In some embodiments, the liposomes are substantially free of glycoproteins. In some embodiments, the liposomes are substantially free of polysaccharides, e.g., a control may be substantially free of polysaccharides.

In other embodiments, the control does not comprise liposomes. The control may comprise an emulsion.

In some embodiments, the nucleic acids of the control are associated with the liposomes. For example, at least about 20%, 25%, 30%, 35%, 40%, 45%, 50%, 55%, 60%, 65%, 70%, 75%, 80%, 85%, 90%, 95%, 86%. 97%, 98%, 99%, 99.5%, 99.6%, 99.7%, 99.8%, or even 99.9% of the nucleic acids in the control may be associated with the liposomes. About 10% to about 100% of the nucleic acids in the control may be associated with the liposomes, such as about 20% to about 100%, about 30% to about 100%, about 40% to about 100%, about 50% to about 100%, about 60% to about 100%, about 70% to about 100%, about 80% to about 100%, or about 90% to about 100%. In some embodiments, substantially all of the nucleic acids in the control are associated with the liposomes.

In some embodiments, the liposomes encapsulate the nucleic acids of the control. For example, the liposomes may encapsulate at least about 10% of the nucleic acids in the control, such as at least about 20%, 25%, 30%, 35%, 40%, 45%, 50%, 55%, 60%, 65%, 70%, 75%, 80%, 85%, 90%, 95%, 86%, 97%, 98%, 99%, 99.5%, 99.6%, 99.7%. 99.8%, or even at least about 99.9% of the nucleic acids in the control. The liposomes may encapsulate about 10% to about 100% of the nucleic acids in the control, such as about 20% to about 100%, about 30% to about 100%, about 40% to about 100%, about 50% to about 100%, about 60% to about 100%, about 70% to about 100%, about 80% to about 100%, or about 90% to about 100%. The liposomes may encapsulate substantially all of the nucleic acids in the control.

The liposomes may comprise phospholipids.

The liposomes may comprise at least one lipid selected from the group consisting of phosphatidylcholine, phosphatidylethanolamine, phosphatidylserine, phosphatidylinositol, phosphatidylglycerol, and sphingomyclin.

The liposomes may comprise at least one lipid selected from the group consisting of dimyristoyl phosphatidylcholine, dipalmitoyl phosphatidylcholine, distearoyl phosphatidylcholine, 1-palmitoyl-2-oleoyl-sn-glycero-3-phosphocholine, dimyristoyl phosphatidylserine, distearoyl phosphatidylserine, dipalmitoyl phosphatidylserine, 1-palmitoyl-2-oleoyl-sn-glycero-3-phospho-L-serine, dimyristoyl phosphatidylinositol, dipalmitoyl phosphatidylinositol, distearoyl phosphatidylinositol, 1-palmitoyl-2-oleoyl-sn-glycero-3-phosphoinositol, dimyristoyl phosphatidylglycerol, dipalmitoyl phosphatidylglycerol, distearoyl phosphatidylglycerol, 1-palmitoyl-2-oleoyl-sn-glycero-3-phospho-(1'-rac-glycerol), dimyristoyl phosphatidylethanolamine, dipalmitoyl phosphatidylethanolamine, distearoyl phosphatidylethanolamine, and 1-palmitoyl-2-oleoyl-sn-glycero-3-phosphoethanolamine.

The liposomes may comprise at least one lipid selected from the group consisting of 1,2-dipalmitoyl-sn-glycero-3-phosphocholine ("DPPC") and 1,2-dimyristoyl-sn-glycero-3-phosphocholine ("DMPC").

Any of the lipids disclosed herein may optionally be pegylated. For example, a liposome may comprise a PEG-modified phosphoethanolamine-based lipid, such as 1,2-dioleoyl-sn-glycero-3-phosphoethanolamine-N-[methoxy(polyethylene glycol)-5000]; 1,2-distearoyl-sn-glycero-3-phosphoethanolamine-N-[methoxy(polyethylene glycol)-5000]; 1,2-dimyristoyl-sn-glycero-3-phosphoethanolamine-N-[methoxy(polyethylene glycol)-5000]; 1,2-dipalmitoyl-sn-glycero-3-phosphoethanolamine-N-[methoxy(polyethylene glycol)-5000]; 1,2-dioleoyl-sn-glycero-3-phosphoethanolamine-N-[methoxy(polyethylene glycol)-3000]; 1,2-distearoyl-sn-glycero-3-phosphoethanolamine-N-[methoxy(polyethylene glycol)-3000]; 1,2-dimyristoyl-sn-glycero-3-phosphoethanolamine-N-[methoxy(polyethylene glycol)-3000]; 1,2-dipalmitoyl-sn-glycero-3-phosphoethanolamine-N-[methoxy(polyethylene glycol)-3000]; 1,2-dioleoyl-sn-glycero-3-phosphoethanolamine-N-[methoxy(polyethylene glycol)-2000]; 1,2-distearoyl-sn-glycero-3-phosphoethanolamine-N-[methoxy(polyethylene glycol)-2000]; 1,2-dimyristoyl-sn-glycero-3-phosphoethanolamine-N-[methoxy(polyethylene glycol)-2000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-[methoxy(polyethylene glycol)-1000]; 1,2-distearoyl-sn-glycero-3-phosphoethanolamine-N-[methoxy(polyethylene glycol)-1000]; 1,2-dimyristoyl-sn-glycero-3-phosphoethanolamine-N-[methoxy(polyethylene glycol)-1000]; 1,2-dipalmitoyl-sn-glycero-3-phosphoethanolamine-N-[methoxy(polyethylene glycol)-1000]; 1,2-dioleoyl-sn-glycero-3-phosphoethanolamine-N-[methoxy(polyethylene glycol)-750]; 1,2-distearoyl-sn-glycero-3-phosphoethanolamine-N-[methoxy(polyethylene glycol)-750]; 1,2-dimyristoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-750]; glycero-3-phosphoethanolamine-N-[methoxy(polyethylene glycol)-550]; 1,2-distearoyl-sn-glycero-3-phosphoethanolamine-N-[methoxy(polyethylene glycol)-550]; 1,2-di myristoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-550]; 1,2-dioleoyl-sn-glycero-3-phosphoethanolamine-N-[methoxy(polyethylene glycol)-350]; 1,2-distearoyl-sn-glycero-3-phosphoethanolamine-N-[methoxy(polyethylene glycol)-350]; 1,2-dimyristoyl-sn-glycero-3-phosphoethanolamine-N-[methoxy(polyethylene glycol)-350]; or 1,2-dipalmitoyl-sn-glycero-3-phosphoethanolamine-N-[methoxy(polyethylene glycol)-350].

The liposomes may comprise cholesterol.

The liposomes may comprise a phosphonium cation or a substituted ammonium cation, wherein the phosphonium cation or the substituted ammonium cation comprises at least one hydrocarbyl group. The at least one hydrocarbyl group may be an alkyl, alkenyl, or alkynyl group. The hydrocarbyl group may comprise from 8 to 22 carbon atoms. 0% to about 5% of the lipids in a control may comprise a phosphonium cation or a substituted ammonium cation by weight, such as about 1% to about 4% or about 2% to about 3%. The liposomes may comprise at least one lipid selected from the group consisting of didodecyldimethylammonium, dioctadecyldimethylammonium, didecyldimethylammonium, dodecylethyldimethylammonium, ethylhexadecyldimethylammonium, dihexadecyldimethylammonium, and dimethylditetradecylammonium. The liposomes may comprise an alkyl ammonium salt, such as an alkyl ammonium halide (e.g., didodecyldimethylammonium bromide).

A control may comprise a chelating agent, such as ethylenediamine tetraacetic acid (EDTA). A control may comprise sodium azide (e.g., as a preservative).

In some embodiments, the average or median diameter of the liposomes is from about 30 to about 1000 nm, such as from about 60 nm to about 600 nm, about 80 nm to about 400 nm, or about 100 nm to about 300 nm. The average or median diameter of the liposomes may be about 100 nm, about 110 nm, about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, or about 300 nm.

In some embodiments, the nucleic acids of a control comprising liposomes are more stable than nucleic acids of a control that does not comprise liposomes, i.e., a control with a similar concentration of nucleic acids of the same origin in a similar buffer. Stability may refer to a reduced propensity to aggregate. In some embodiments, the nucleic acids of a control comprising liposomes are less likely to aggregate than nucleic acids of a control that does not comprise liposomes. Aggregation may be determined, for example, by measuring the apparent length of nucleic acids in a control, for example, by using a Bioanalyzer (Agilent). The nucleic acids of a control according to various embodiments of the invention have not aggregated if most nucleic acids of the control fall within an observed size range of about 35 base pairs to about 1000 base pairs (such as about 50 base pairs to about 1000 base pairs), e.g., as observed using a Bioanalyzer. The nucleic acids of a control have aggregated if most nucleic acids of the control are observed to be more than 1000 base pairs, e.g., as observed using a Bioanalyzer.

In some embodiments, the nucleic acids of a control are stable a period of time of about a period of time of about a period of time of about a period of time of about and/or the nucleic acids do not form aggregates when stored at a temperature of about 0° C. to about 100° C., such as about 4° C. to about 50° C., about 15° C. to about 50° C., about 4° C. to about 45° C., about 15° C. to about 45° C., about 4° C. to about 25° C., or about 15° C. to about 25° C., e.g., most of the nucleic acids of the control fall within an observed size range of about 35 base pairs to about 1000 base pairs as analyzed by a Bioanalyzer after storage. In some embodiments, the nucleic acids of a control are stable and/or the nucleic acids do not form aggregates when stored at a temperature of about 0° C. to about 100° C. for a period of time of about 1 day to about 5 years. In some embodiments, the nucleic acids of a control are stable and/or the nucleic acids do not form aggregates when stored at a temperature of about 4° C. to about 45° C. for a period of time of about 1 day to about 5 years, such as about 1 week to about 2 years, about 1 month to about 18 months, or about 2 months to about 12 months. In some embodiments, the nucleic acids of a control are stable and/or the nucleic acids do not form aggregates when stored at a temperature of about 4° C. to about 25° C. for a period of time of about 1 day to about 5 years, such as about 1 week to about 2 years, about 1 month to about 18 months, or about 2 months to about 12 months. In some embodiments, the nucleic acids of a control are stable and/or the nucleic acids do not form aggregates when stored at a temperature of about 15° C. to about 25° C. for a period of time of about 1 day to about 5 years, such as about 1 week to about 2 years, about 1 month to about 18 months, or about 2 months to about 12 months.

In some embodiments, the nucleic acids of a control are stable when stored at a temperature of about 2° C. to about 42° C., e.g., most of the nucleic acids of the control fall within an observed size range of about 50 base pairs to about 1000 base pairs as analyzed by a Bioanalyzer after storage or the control may be successfully sequenced after storage by next-generation sequencing. In some embodiments, the nucleic acids of a control do not form aggregates when stored at a temperature of about 2° C. to about 42° C. for a period of time of about 1 day to about 5 years, such as about 1 week to about 2 years, about 1 month to about 18 months, about 2 months to about 12 months, about 1 month to about 12 months, about 1 month to about 6 months, about 1 month to about 4 months, about 1 month to about 3 months, about 1 week to about 4 months, or about 1 week to about 3 months.

In some embodiments, the nucleic acids of a control do not form aggregates when stored at a temperature of about 2° C. to about 42° C., e.g., most of the nucleic acids of the control fall within an observed size range of about 50 base pairs to about 1000 base pairs as analyzed by a Bioanalyzer after storage. In some embodiments, the nucleic acids of a control do not form aggregates when stored at a temperature of about 2° C. to about 42° C. for a period of time of about 1 day to about 5 years, such as about 1 week to about 2 years, about 1 month to about 18 months, about 2 months to about 12 months, about 1 month to about 12 months, about 1 month to about 6 months, about 1 month to about 4 months, about 1 month to about 3 months, about 1 week to about 4 months, or about 1 week to about 3 months.

The period of time may be at least 1 day, at least 1 week, at least 1 month, at least 2 months, at least 3 months, at least 4 months, at least 5 months, at least 6 months, or at least 1 year. The period of time may be about 1 week to about 5 years, about 1 month to about 5 years, about 2 months to about 5 years, about 6 months to about 5 years, about 1 year to about 5 years, about 1 week to about 2 years, about 1 month to about 2 years, about 2 months to about 2 years, or about 6 months to about 2 years. The period of time may be about 1 day, about 1 week, about 1 month, about 2 months, about 3 months, about 4 months, about 5 months, about 6 months, or about 1 year.

EXEMPLIFICATION

Example 1: Source of Trisomy Nucleic Acids

Placentas and the associated membranes were rinsed in cold stabilizing buffer. Each sample was processed individually. Under direct visualization with a dissecting microscope, the chorionic membrane was carefully separated from floating/anchoring villi and minced into 3-4 mm pieces. The fragments were removed from the medium by centrifugation. Cells were released from the tissue by a series of enzymatic dissociation steps. Dissociated cells were collected, centrifuged, washed and pooled. The cells were re-suspended in DMEM/F12 supplemented media, plated in the same medium on gelatin-coated wells and cultured under standard conditions (in 20% 02). Colonies of undifferentiated cells, which formed after 7-10 days, were manually dissected, and clumps of 20-40 cells were re-plated and passaged 5-10 times. Colonies were derived from multiple chorionic membranes (6-11 weeks of gestation). A portion was banked by freezing at passages 3-5.

Example 2: Source of Maternal Nucleic Acids

Female whole blood was validated as female, heterozygous for the Factor V Leiden mutation, and homozygous mutant for the MTHFR 677 mutation. B cell lines from the blood were isolated and EBV immortalized using standard methods. The EF0000004 Factor V EBV transformed B cell line (referred to as "Factor V" herein) was expanded and used to make frozen stocks and whole cell pellets.

Alternatively, genomic DNA was derived from peripheral blood mononuclear cells (PBMCs) for use in Examples 14-17. PBMC-derived DNA represented a more normal NCV distribution via the Illumina algorithm (MPS-based) than genomic DNA obtained from EBV-transformed cell lines.

Example 3: Source of Trisomic Nucleic Acids

Cytotrophoblasts (trophoblast progenitors) were obtained from Dr. Katherine Bianco (UCSF), who provided nine frozen cell lines: three cell lines karyotyped as Trisomy 13, three cell lines karyotyped as Trisomy 18, and three cell lines karyotyped as Trisomy 21 (Table 2). The cytotrophoblast cell lines were either male (XY) or female (XX), and each cell line has a unique gestational age. Three cytotrophoblast cell lines were chosen for development: Trisomy 13 Cell Line 3 (T13 C3), Trisomy 18 Cell Line 1 (T18 C1), and Trisomy 21 Cell Line 2 (T18 C2). All three cell lines were male (XY) and were capable of expansion. The cell lines were initially expanded to make multiple frozen Master Stocks.

TABLE 2

Trophoblast cell lines.

| Cell Type | Sample name | Aneuploidy | Gestational Age (weeks) | Karyotype | Passage # |
|---|---|---|---|---|---|
| Trophoblast Progenitor | T13 C1 | Trisomy 13 | 12.4 | 47 XX +13 | P5 |
| Trophoblast Progenitor | T13 C2 | Trisomy 13 | 16.1 | 47 XX +13 | P6 |
| Trophoblast Progenitor | T13 C3 | Trisomy 13 | 15.2 | 47 XY +13 | P7 |
| Trophoblast Progenitor | T18 C1 | Trisomy 18 | 15.4 | 47 XY +18 | P5 |
| Trophoblast Progenitor | T18 C2 | Trisomy 18 | 22.5 | 47 XY +18 | P4 |

TABLE 2-continued

Trophoblast cell lines.

| Cell Type | Sample name | Aneuploidy | Gestational Age (weeks) | Karyotype | Passage # |
|---|---|---|---|---|---|
| Trophoblast Progenitor | T18 C3 | Trisomy 18 | 23.3 | 47 XY +18 | P6 |
| Trophoblast Progenitor | T21 C1 | Trisomy 21 | 12.3 | 47 XX +21 | P6 |
| Trophoblast Progenitor | T21 C2 | Trisomy 21 | 13.6 | 47 XY +21 | P6 |
| Trophoblast Progenitor | T21 C3 | Trisomy 21 | 15 | 47 XX +21 | P6 |

The cells were grown to confluence under sterile conditions in a 37° C. incubator with 5% $CO_2$ using a predefined media consisting of DMEM/F12, Glutamax (Invitrogen, Part #10565042), 10% fetal bovine serum (FBS), 100 Units/ mL penicillin, 100 µg/mL streptomycin, 10 µM SB431542 a TGF-beta inhibitor (4-[4-(1,3-benzodioxol-5-yl)-5-(2-pyridinyl)-1H-imidazol-2-yl]benzamide) (Tocris, Part #16-14), and 10 ng/mL Recombinant Human Fibroblast Growth Factor-2 (FGF), 146 aa (R&D Systems, Catalog #233-FB-025).

Figure 2:
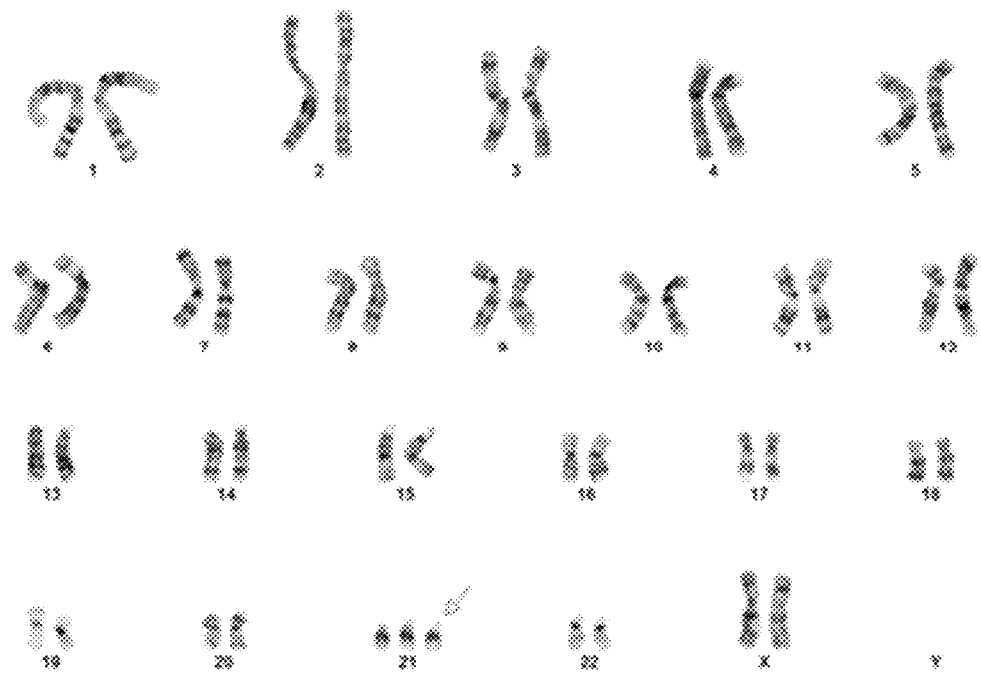
FIG. 2 consists of three panels, labeled panel (A), (B), and (C). Panel (A) depicts karyotyping for cell line T13 C3, which is genotyped male with trisomy 13. Panel (B) depicts karyotyping for cell line T18 C1, which is genotyped male with trisomy 18. Panel (C) depicts karyotyping for cell line T21 C2, which is genotyped female with trisomy 21.

Using the Master Stocks of the three cytotrophoblasts, the cell lines were again expanded to make multiple frozen Working Stocks. During the expansion of the Working Stocks, blinded samples were karyotyped to confirm their genotypes (FIG. 2). Working Stocks of the three cytotrophoblasts and the Factor V cell line were expanded to make whole cell pellets. Genomic DNA from each of the three cytotrophoblasts and the Factor V cell line were purified from the cell pellets using the Gentra Puregene Method (Qiagen). After purification, genomic DNA concentration was measured on a NanoDrop 2000/2000c Spectrophotometer (Thermo) and purity was evaluated by agarose gel electrophoresis.

Example 4: Method of Shearing DNA

Genomic DNA was diluted to 150 ng/µL in Tris-EDTA, pH 8.0 and sheared into smaller fragments using a M220 Focused Ultrasonicator (Covaris). The genomic DNA from the Trisomy cell lines was sheared in a 1 mL MilliTube to an average maximum peak of 150 base pairs. The genomic DNA from the Factor V cell line was sheared in a 1 mL MilliTube to an average maximum of 170 base pairs.

Figure 3:
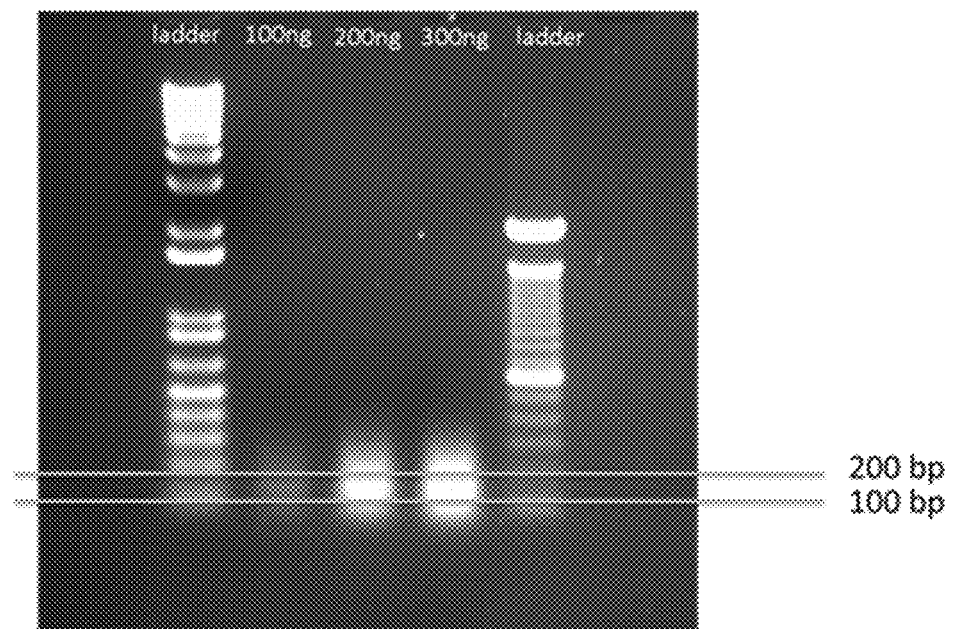
FIG. 3 is an image of a 2% agarose gel comprising DNA sheared to approximately 170 bp using a Covaris ultrasonicator.
Figure 4:
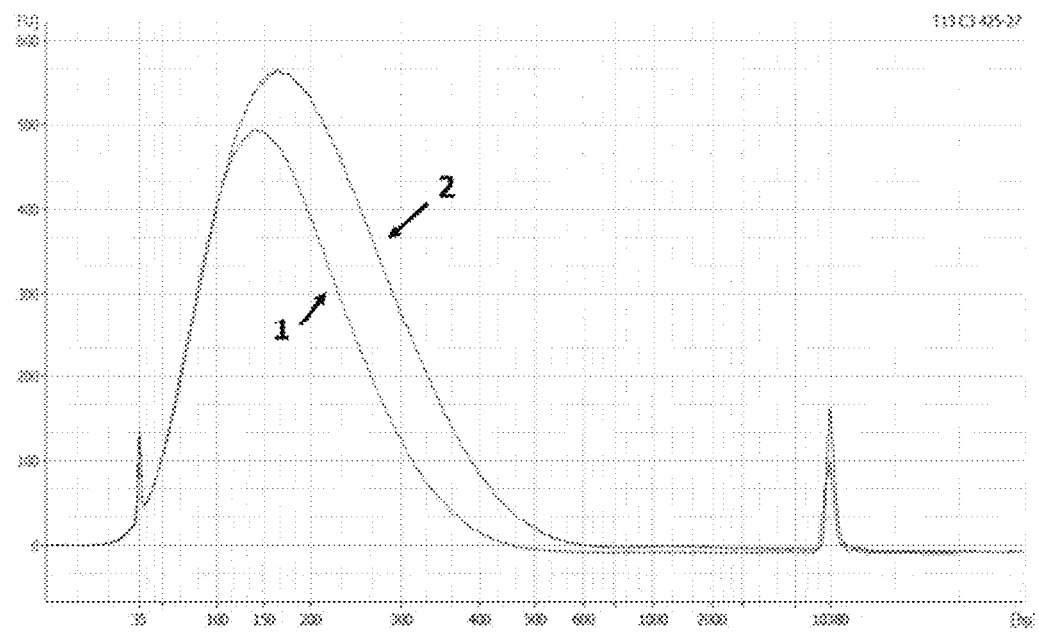
FIG. 4 is a 2100 Bioanalyzer plot of fluorescence ("FU") versus nucleic acid length ("bp") for nucleic acids from the T13 C3 cell line sheared to about 150 bp (labeled "1") and a second to about 170 bp (labeled "2") using a Covaris ultrasonicator.
Figure 5:
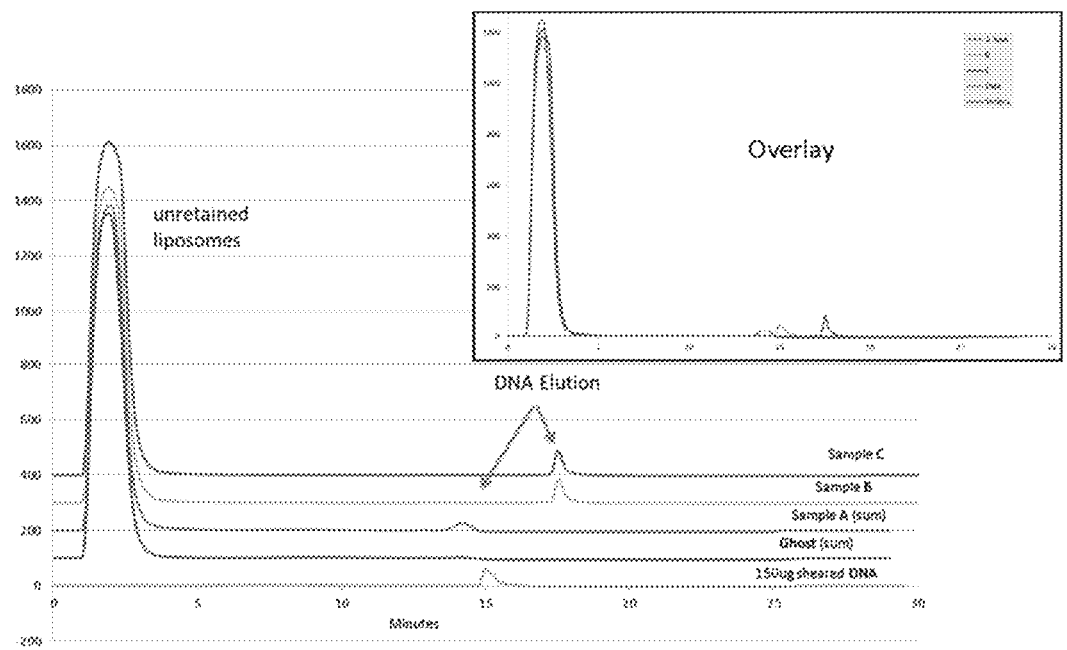
FIG. 5 depicts stacked anion-exchange chromatography traces for three preparations of DNA (Samples A, B, and C)

Sheared DNA was analyzed for the effectiveness of shearing by agarose gel electrophoresis and for fragment size using the High Sensitivity DNA Kit for the 2100 Bioanalyzer (Agilent). Agarose gel images indicate complete disintegration of the whole genomic DNA into fragments <1000 bp in size (FIG. 3), and Bioanalyzer data provide a more precise picture of the DNA fragment size distribution and the distinction between the results of the two different shearing methodologies (FIG. 4).

Example 5: Blending Sheared Nucleic Acids

DNA fractions were blended volumetrically from 0.15 mg/mL stock solutions. Typically, a 1:3 fetal to maternal solution is prepared (25%) and two-fold dilutions are made thereafter for linearity series (12.5%, 6.25%, 3.12%). These preparations may then be used as DNA stocks, e.g., for liposome encapsulation.

Example 6: Liposome Preparation

Small DNA fragments (<1000 base pairs) may be incorporated into liposomes as described by Monnard, et. al.

(Biochim Biophys Acta. (1997)1329(1):39-50). In some embodiments, the liposomes are constructed with saturated phospholipids because of the structural homogeneity of the resulting liposomes and because of the lack of oxidation-prone alkene functionalities. These lipids also exhibit favorable gelling temperatures at or above ambient temperature, ensuring that the liposomes will be in a gel phase during refrigerated storage and less susceptible to leakage or degradation. Specifically, DPPC (1,2-dipalmitoyl-sn-glycero-3-phosphocholine, CAS #63-89-8) and DMPC (1,2-dimyristoyl-sn-glycero-3-phosphocholine, CAS #18194-24-6) were investigated. Cholesterol (CAS #57-88-5) and DDAB (didodecyldimethylammonium bromide, CAS #: 3282-73-3) were used additives to the tested formulations. In one embodiment, liposomes comprised DMPC and DDAB at 1:0.025 molar ratios. The DMPC:DDAB lipid mix was prepared by dissolution in Cyclohexane/Ethanol (66:1) at 50 mg/mL followed by lyophilization in order to prepare a finely divided, homogeneous substrate for vesicle formation. Following lyophilization, the lipids were rehydrated with TE Buffer (10 mM TRIS, 1 mM EDTA, pH 8.0) at 200 mg/mL, forming a thick slurry. The slurry was subjected to bath sonication for 20 min, which results in a uniform suspension of vesicles suitable for DNA incorporation. To this suspension, a solution of 3 volume equivalents of blended, sheared DNA in TE buffer (0.15 mg/mL) was added for a final DNA concentration of 0.1125 mg/mL. The sheared DNA was then incorporated into the liposomes using standard freeze-thaw methods whereby samples were frozen in liquid nitrogen (−196° C.) for 1 min and then warmed to 45° C. for 15 min for a total of 5 cycles (Mayer, et. al. Biochim et Biophys Acta (1985) 817:193-196). At this stage, the DNA is incorporated into the crude vesicles, which are multi-laminar and disparate in size.

Crude liposomes were subjected to extrusion, which down-sizes the liposomes, thereby creating a controlled and reproducible size population, and disrupts multi-laminar vesicles. The extrusion process was achieved using the Avanti® Mini-Extruder (Avanti Polar Lipids, Part #: 610000) affixed with a Polycarbonate extrusion disk with 100 nm, 200 nm, or 400 nm pores. Crude samples were processed, without dilution at 35-50° C., for a total of 31 total passages, resulting in a highly uniform size distribution.

Following extrusion, the liposomes were purified by anion exchange chromatography, by dilution of the extruded liposomes to 20 mg/mL lipid in Tris buffer (50 mM) and passage over a 5 mL pre-packed HiTrap DEAE FF purification column (GE Healthcare, Part #: 17-5154-01). Purified liposomes (referred to as "Bulk LipoDNA") were collected in a 4 mL fraction, which was not retained by the column, while the unincorporated DNA remained bound to the stationary phase (FIG. 6). Bound DNA can be subsequently eluted by increasing the salt concentration in the mobile phase to 1 M sodium chloride.

Example 7: Liposomes Protect Nucleic Acids from Nucleases

Two preparations of DNA-loaded DMPC liposomes extruded through a 100 nm polycarbonate extrusion disk, a corresponding "ghost" liposome, and isolated DNA were treated with Benzonase nuclease under various conditions. The positive correlation between DNA concentration with and without Benzonase indicates that the liposomes encapsulate the DNA, thereby shielding it from enzymatic digestion (Table 3). The addition of Triton disrupted the liposome carriers allowing for complete DNA digestion. Residual DNA was detected by the KAPA qPCR method described below after inactivation with Proteinase K and nucleic acid extraction.

TABLE 3

Liposomes protect sheared nucleic acids from digestion by benzonase

| | Untreated | Benzonase (37° C. for 2 hours) | 3% triton + benzonase (37° C. for 2 hours) |
|---|---|---|---|
| Sample B | 78 ng/mL | 80 ng/mL | no DNA detected |
| Sample C | 86 ng/mL | 87 ng/mL | no DNA detected |
| Ghost | no DNA detected | not tested | not tested |
| sheared DNA + ghost | not tested | no DNA detected | no DNA detected |
| sheared DNA | DNA present | no DNA detected | no DNA detected |

Example 8: Analytic Methods

Bioanalyzer. An Agilent 2100 Bioanalyzer was used in conjunction with DNA 1000 and High Sensitivity DNA kits in order to assess the average lengths and length distributions of sonicated DNA and DNA in liposomes. Because fetal-derived cfDNA has been reported to be shorter than mother-derived cfDNA, the Bioanalyzer was used to confirm that the average length of each sonicated aneuploidy cell line DNA was shorter than the average length of sonicated normal DNA.

Nanodrop. A ThermoFisher NanoDrop 2000 spectrophotometer was used to measure the concentration of genomic DNA, sheared DNA, and liposome suspensions. The absorption at 260 nm was used to calculate the concentration of double stranded DNA, i.e., 1 $OD_{260}$=0.05 mg/mL. Light-scatter absorption values obtained for liposomes at 260 nm were used to monitor consistency of concentrations of replicate samples throughout the liposomes preparation process. Nanoparticle Tracking Analysis. Nanoparticle Tracking Analysis (NTA) utilizes the properties of both light scattering and Brownian motion in order to obtain the particle size distribution of samples in liquid suspension (see FIG. 6). In addition, particle counts can also be determined such that liposome concentration can be determined. NTA analysis was completed by Particle Characterization Laboratories Incorporated (Novato, Calif.) using a NanoSight LM 10-HS instrument (Malvern instruments, Worcestershire, UK). Prior to shipment, samples were diluted 100:1, and further dilution was conducted at the discretion of the testing lab prior to analysis, which was typically an additional 2000:1 dilution.

PicoGreen Analysis. A modification of ThermoFisher's Quant-iT™ PicoGreen® dsDNA Assay Kit (Part #P7589) was used as a quantitation method for the encapsulated DNA content in purified LipoDNA. PicoGreen is a fluorescent dye that intercalates double-stranded DNA, resulting in a detectable fluorescent enhancement. PicoGreen is particularly useful because it can penetrate liposomes, binding to encapsulated DNA and negating the need for extraction when analyzing the high concentration bulk sample. Samples were prepared by combining equal volumes of the analyte solutions and a 1/200 dilution of PicoGreen dye solution as delineated in the ThermoFisher manual. In addition, samples were placed in a PicoGreen bath for 5 min prior to detection to ensure that the dye had fully equilibrated into the liposomes. Standard curves for determining the DNA concentration were typically prepared from sheared DNA, which had been quantitated by Nanodrop prior to being sheared (see FIG. 8).

DNA Extraction. Prior to the analysis of LipoDNA samples using a PCR technology (e.g., qPCR, ddPCR, or NGS), nucleic acids may be extracted from their liposomal carriers. This was most often accomplished utilizing Qiagen's QIAamp Circulating Nucleic Acid Kit (Part #: 55114), following the procedure specified in the manual. This kit is widely used in cfDNA research and in testing communities. LipoDNA samples from 0.05 mL to 1.0 mL were diluted to 1 mL in PBS prior to extraction, and nucleic acids were eluted using between 50 and 75 µL of buffer, depending on the assay. Alternatively, the Macherey-Nagle NucleoSpin® Plasma XS (Part #: 740900) may be used to purify nucleic acids from liposomes.

qPCR DNA Quantitation. Digital PCR was performed using a Bio-Rad QX200 Droplet Digital PCR system. Well-known primers and probes were used in TaqMan assays in order to assess the concentrations and relative concentrations of chromosomes 1, 13, 18, 21, X and Y. The probe for chromosome 1 was labeled with HEX (hexachlorofluorescein) and the probes for the other chromosomes were labeled with FAM (fluorescein). All probes were quenched with BHQ-1 (Black Hole Quencher 1). In order to obtain accurate results, approximately 100 ng of DNA was present in each 20 µL reaction.

A cell line with a trisomy should contain 3 copies of a chromosome instead of the usual 2. In practice, however, not all cells within a cell line are aneuploid, and karyotyping revealed that several cell lines under evaluation were not 100% aneuploid. Assessing the degree of aneuploidy is important in order to ensure that a control that purports to mimic an aneuploidy at a given fetal fraction in fact does so. Therefore, digital PCR was used to assess the degree of aneuploidy in various cell lines. An example is shown in FIG. 9, in which DNA extracted from cell line T21 C1 displayed a lower level of chromosome 21 than expected (CNV of 3 is triploid, 2 is diploid, and 1 is haploid), which suggests that about half of the cells are not triploid. DNA from the T13 C3 and T18 C1 cell lines displayed CNV levels closer to the expected 3 for the aneuploid chromosomes, and PCR analysis also indicated that these two cell lines contain a copy of the Y chromosome (FIG. 9).

Digital PCR is also used to assess and track the concentration of DNA. Conventional $OD_{260}$ measurements of DNA concentrations can be affected by turbidity and the presence of RNA, and digital PCR is less sensitive to these conditions. Because genomic DNA has the potential to be centimeters in length, which is incompatible with droplet digital PCR, it was first digested with a cocktail of restriction enzymes that were selected because they do not cut within the amplicons. This cocktail comprised EcoRV, KpnI, NcoI, ScaI, and SacI. In comparison, unlike restriction enzymes, sonication cuts DNA in a more random nature, which has the potential to, and has been observed to, cut within the regions that would otherwise be amplified by digital PCR. The effect is that sonicated DNA has a lower apparent concentration by digital PCR than DNA digested with carefully-selected restriction enzymes. By measuring the apparent concentration of DNA by digital PCR before and after sonication, it is possible to obtain a conversion factor for adjusting the apparent concentration of sonicated DNA to restriction enzyme digested DNA. This is helpful at later stages after sonicated DNA is incorporated into liposomes and present at low concentrations. By multiplying the apparent concentration of the diluted, sonicated DNA with the conversion factor, it is possible to obtain an accurate concentration of diluted, sonicated DNA by digital PCR.

Digital PCR is also used to assess the fetal fraction in the final product, by using the amplicon for the Y chromosome. For male aneuploid cell lines, the Y chromosome is present at one copy for every two copies of the normal chromosomes and for every 3 copies of the aneuploid chromosome. Fetal fraction is calculated by multiplying the apparent copies of chromosome Y in relation to the apparent copies of chromosome 1 by a factor of two. (A 100% fetal fraction sample would have 50% apparent copies of chromosome Y in relation to copies of diploid chromosome 1).

Example 9: Analysis of Control Samples Comprising Mixtures of "Maternal" and Trisomy 21 DNA Test samples were run as "research samples" in the assay. Samples were formulated as outlined in Table 4, infra. A dilution panel of liposome encapsulated fetal fraction (T21) at 0%, 3.1%, 6.25%, 12.5%, and 25% was formulated in liposome encapsulated Maternal DNA in TE buffer. Samples formulated at 25% fetal fraction in plasma like diluents (Basematrix, Scracon, and Matribase) were included in this study with a goal to evaluate which diluent is best suited for the formulation of controls. Samples were formulated at a concentration of ~30 ng/mL.

TABLE 4

Control samples comprising T21 DNA evaluated for aneuploidy.

| Samples | % Maternal DNA | % Fetal (T21) DNA | Format | NCV Diagnosis |
|---|---|---|---|---|
| 426-03B | 100 | 0 | 4 mL; ~30 ng/mL in TE | −6.19 Normal |
| 426-03C | 96.9 | 3.1 | 4 mL; ~30 ng/mL in TE | −2.13 Normal |
| 426-03D | 93.75 | 6.25 | 4 mL; ~30 ng/mL in TE | 0.24 Normal |
| 426-03E | 87.5 | 12.5 | 4 mL; ~30 ng/mL in TE | 6.94 Aneuploid |
| 426-03F | 75 | 25 | 4 mL; ~30 ng/mL in TE | 18.81 Aneuploid |
| 426-03G | 0 | 100 | 4 mL; ~30 ng/mL in TE | 16.76 Aneuploid |
| 426-03F-MB | 75 | 25 | 4 mL; ~30 ng/mL in Matribase | 16.19 Aneuploid |
| 426-03F-BM | 75 | 25 | 4 mL; ~30 ng/mL in BaseMatrix | 17.24 Aneuploid |
| 426-03F-SC | 75 | 25 | 4 mL; ~30 ng/mL in SeraCon II | 16.96 Aneuploid |
| 426-03F-DNA (no extraction) | 75 | 25 | 1.2 µg in 80 µL of 0.1x TE | 83.66 Aneuploid |

Figure 1:
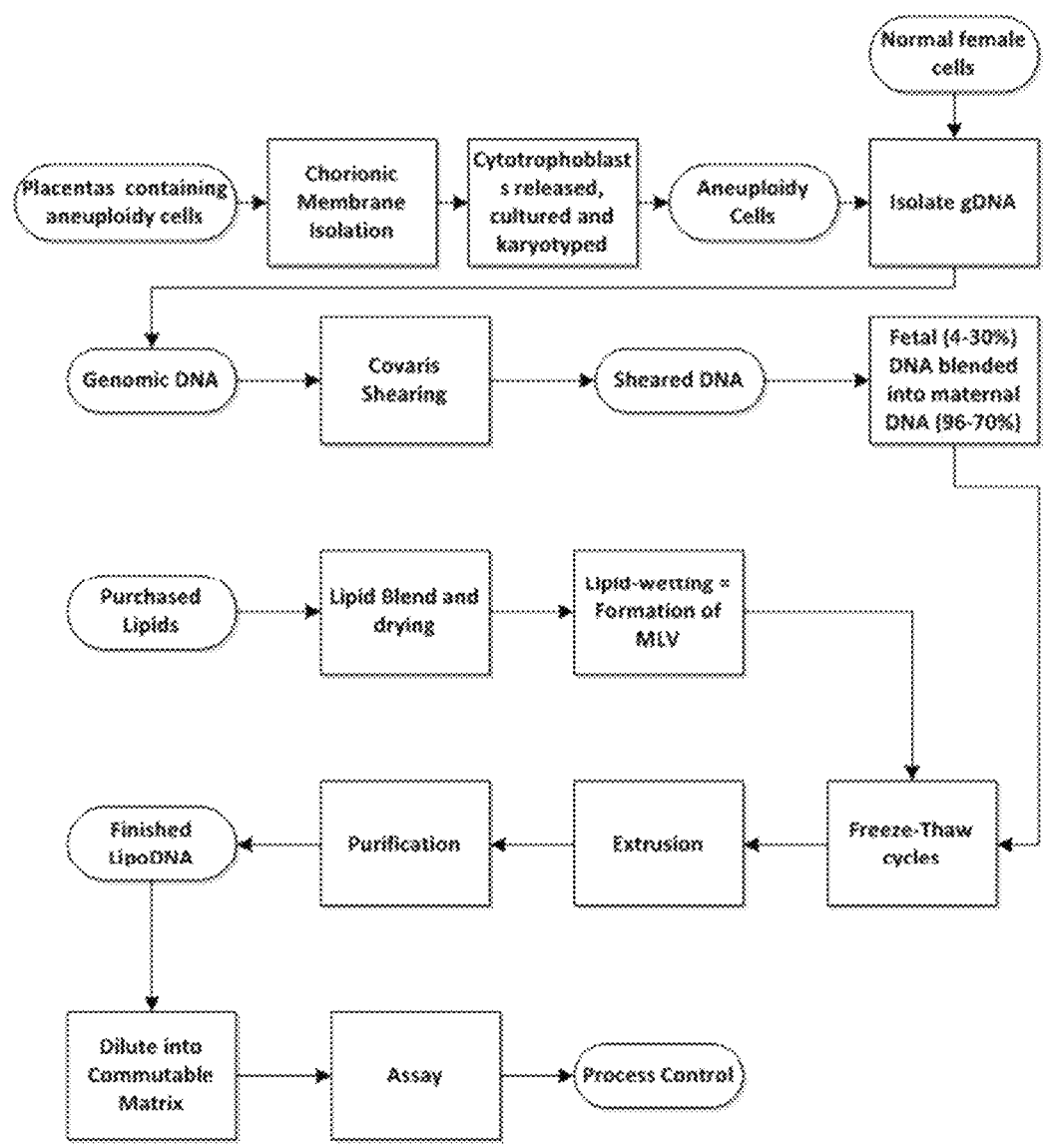
FIG. 1 presents a preparation workflow for producing controls according to some embodiments of the invention.

Samples were processed at the test site in the same way as patient samples. Briefly, the samples were tested on an R&D flow cell along with other test samples. Calling aneuploidy involves Normalized Chromosome Value (NCV) scores that cross a certain threshold over a normal variation of baseline data. Test results are summarized in the Table 4 above and in FIG. 10. Samples comprising a 12.5% or a 25% fetal fraction were called as Aneuploidy, and other samples were called normal. This data demonstrates that the process shown in FIG. 1 can be used to prepare a stable, commutable cfDNA control.

Example 10: Methods of Using Controls with Diagnostic Tests that Utilize Nucleic Acid Sequencing Samples containing different amounts of sonicated T21 C1 DNA within a background of sonicated Factor V DNA (normal maternal background DNA) were sent to GENEWIZ (South Plainfield, N.J.) for analysis. GENEWIZ was instructed to analyze them by NGS on an Illumina HiSeq with 2×150 base paired-end reads using their typical whole genome shotgun (WGS) workflow starting with the post-sonication stage (i.e., extraction followed by end polishing and library generation). While conventional NIPT testing uses shorter reads (e.g., 36 base), longer reads were requested in order to improve mapping and to have the potential to detect DNA fragments that were shorter than 150 bases in length, based on their overlapping sequences.

FastQ files for paired-end reads were obtained. These files were analyzed to assign individual NGS reads to chromosomes and to determine the relative abundance of reads from the different chromosomes. The resulting data was compared to data obtained from the analysis of public NGS files from 903 NIPT samples that were part of the NIFTY trial and from the analysis of public NGS files from two reference cell lines from the Genome-ln-A-Bottle (GIAB) consortium.

The 903 samples from the NIFTY trial (BGI Diagnosis Co, P.R.C) reported a correlation between the % GC content in NGS reads from a given sample and biases in the apparent abundance of reads from different chromosomes. Reads from different chromosomes differ in terms of how much they are affected by GC content, and the removal of this bias is critical in comparing data between samples in order to differentiate between normal and abnormal samples. This correlation appears to be mostly linear, and either the data obtained from a NIPT test should be corrected for the correlation or the NIPT test should be designed around this factor.

The GENEWIZ sequencing results displayed a higher average GC content than GC contents found in the public data for any of the 903 NIFTY trial samples, the GIAB reference genome samples NA12878 and NA24385 derived from the EBV transformed cell lines GM12878 and GM24385, and PBLs from three donors STL001/2/3. Agarose gel extraction of the samples prior to sequencing resulted in even higher GC contents, resulting in a stronger chromosomal abundance bias (FIG. 11). Accordingly, agarose gel extraction should be avoided to reduce GC bias. Additionally, GC bias may be further mitigated by applying a linear correction.

With correction for GC bias, the apparent concentrations of many chromosomes fell into normal ranges (FIG. 12). The samples that contained higher amounts of T21 DNA appeared to be T21 positive. Those that contained no T21 DNA (i.e., samples comprising solely Factor V DNA) appeared to be T21 negative. Even with correction for GC content, however, the apparent chromosomal abundances were low for some chromosomes and high for others. Notably, chromosomes 19 and X appeared to be less abundant than expected.

Example 11: Methods of Using Controls with Diagnostic Tests that Utilize Nucleic Acid Microarrays Controls comprising trisomy 21 were prepared according to Table 5 and provided to microarray laboratory for analysis.

TABLE 5

Characteristics of Trisomy 21 Controls

| Sample | % Maternal DNA | % Fetal (T21) DNA | Format |
|---|---|---|---|
| 426-04B | 100 | 0 | 4 mL; ~30 ng/mL in TE |
| 426-04C | 96.9 | 3.1 | 4 mL; ~30 ng/mL in TE |
| 426-04F | 75 | 25 | 4 mL; ~30 ng/mL in TE |
| 426-04G | 0 | 100 | 4 mL; ~30 ng/mL in TE |
| 426-04F-MB | 75 | 25 | 4 mL; ~30 ng/mL in Matribase |
| 426-04F-DNA (no extraction) | 75 | 25 | 1.2 µg in 80 µL of 0.1 x TE (15 ng/µL) |

All samples (except 426-04F-DNA) were diluted to 5 mL with PBS, and the DNA was extracted using the Qiagen QIAamp circulating nucleic acid kit and eluted in 100 µL. Concentrations for the extracted DNA were measured using the ssDNA Qubit assay (Table 6).

TABLE 6

Concentrations of trisomy 21 controls after purification

| Sample | Concentration (ng/µL) |
|---|---|
| 426-04B | 0.980 |
| 426-04C | 0.586 |
| 426-04F | 0.603 |
| 426-04G | 0.273 |
| 426-04F-MB | 0.273 |
| 426-04F-DNA (no extraction) | 8.39 |

The DNA was amplified with a procedure consisting of 3 steps. Briefly, the whole of each sample, including 50 ng of sample 426-04F-DNA, was used in Steps 1 and 2 Samples G and F-MB had low concentrations, and so the whole sample was carried through to PCR (Step 3), instead of half, which is the usual procedure. A reference disomy DNA was also processed alongside the samples. Following Step 3, which comprised PCR, the nucleic acid concentrations in the samples and reference were measured on a NanoDrop (Table 7).

TABLE 7

Concentration and purity of trisomy 21 controls after amplification

| Sample | Concentration (ng/µL) | 260/280 | 260/230 |
|---|---|---|---|
| 426-04B | 81.7 | 1.98 | 2.64 |
| 426-04C | 77.8 | 1.92 | 2.56 |
| 426-04F | 62.1 | 2.00 | 2.46 |
| 426-04G | 80.1 | 1.92 | 2.48 |
| 426-04F-MB | 85.1 | 1.96 | 2.44 |
| 426-04F-DNA (no extraction) | 8.69 | 1.87 | 2.25 |
| Reference | 77.1 | 1.88 | 2.27 |

The amplification yields passed quality control, and 1 µg of each control (and reference) were labeled with the Oxford Gene Technology CytoSure DNA Labeling kit. Controls were labeled with Cy3 and the reference was labeled with Cy5. The labeling efficiency was measured on a NanoDrop (Table 8).

TABLE 8

Labeling of trisomy 21 controls

| Sample | Dye Concentration (pmol/µL) | DNA concentration (ng/µL) |
|---|---|---|
| 426-04B | 81.7 | 1.98 |
| 426-04C | 77.8 | 1.92 |
| 426-04F | 62.1 | 2.00 |
| 426-04G | 80.1 | 1.92 |
| 426-04F-MB | 85.1 | 1.96 |
| 426-04F-DNA (no extraction) | 8.69 | 1.87 |
| Reference | 77.1 | 1.88 |

The labeling passed quality control and the samples were mixed with reference, dried down and prepared for hybridization onto the Oxford Gene Technology NIPT microarray overnight. The slide was washed, scanned, and feature extracted following a 22 hour hybridization, and the resulting output files were analyzed with a preliminary R script for chromosome 21 excess detection.

The T21 spike samples at 25% performed well in the NIPT assay, displaying a very strong positive signal as measured by $-\log_{10} P$ values (FIG. 14). The array quality control metrics were good, except for control G, which displayed a high DLRS ("derivative log ratio spread"). The 0% and 100% T21 samples gave strong negative and positive signals, as expected. The 3% T21 spike in was not detected as a trisomy in the assay (FIG. 14).

Example 12: Stability and Shelf Life

Chromosome 13 trisomy samples were prepared according to Examples 4-6, with and without liposomes. Samples were formulated with Matribase as described in Example 9. Briefly, a representative trisomy control comprising 12% Trisomy 13 genomic DNA and 88% PBMC genomic DNA by weight was sheared and encapsulated in liposomes. The control was diluted to approximately 20 ng/mL with MatriBase and aliquoted into 1.2 mL portions. Additional controls were prepared without liposomes, diluted with MatriBase, and aliquoted into 1.2 mL portions.

Controls were monitored in parallel. At each time point, 1 mL of an aliquot was extracted using the QIAGEN QIAamp circulating nucleic acid kit with elution into 1 mL of AVE buffer. Stability was assessed by digital droplet PCR and next-generation sequencing (NGS). For the digital PCR assay, controls were monitored by probing a single copy gene on chromosome 1. NGS assays were performed by an external reference lab that routinely runs NIPS patient samples.

Digital PCR suggested that each liposome control and non-liposome control displayed comparable stability and that stability was independent of temperature (FIG. 31).

Samples were stored for 33 days at temperatures of 4° C., 25° C., or 42° C., and then nucleic acids were extracted as described in Example 8. The controls were sent to a commercial reference laboratory for testing using their standard workflow with sequencing on an Illumina HiSeq platform. Library preparation was performed by the commercial laboratory 14 days later, after the 33 days of storage, and thus, library preparation was performed 47 days after preparing the samples. Comparable amounts of DNA were extracted from each sample; however, samples prepared without liposomes did not perform as well during the NGS library preparation method, resulting in poor yields (Table 9). The controls formulated without liposomes ultimately failed library preparation and could not be sequenced. Library preparation was reattempted and the second attempt was also unsuccessful, suggesting that the failure was attributable to the degradation of the controls formulated without liposomes rather than operator error. Each of the controls that were formulated with liposomes were successfully sequenced (FIG. 16 and Table 10).

TABLE 9

Extraction of DNA from stored samples and concentration after NGS library preparation method.

| Sample | Total DNA Concentration after extraction [pg/µL] | Concentration of Library Prep. [nM] |
|---|---|---|
| Encapsulated 33 Days 4° C. | 255.18 | 28.60 |
| Naked-DNA 33 Days 4° C. | 235.79 | 3.90 |
| Encapsulated 33 Days 25° C. | 188.50 | 31.55 |
| Naked-DNA 33 Days 25° C. | 212.09 | 4.61 |
| Encapsulated 33 Days 42° C. | 277.75 | 31.53 |
| Naked-DNA 33 Days 42° C. | 232.67 | 4.94 |

DNA from samples comprising liposomes was sequenced, and the ploidy of chromosomes 13, 18, and 21 was assessed (FIG. 16). Storage at various temperatures for 33 days did not affect the performance of samples prepared with liposomes.

Next generation sequencing was attempted on the samples at a later time point after additional storage, 125 days after preparing the samples. The controls formulated without liposomes failed library preparation and could not be sequenced. Library preparation was reattempted and the second attempt was also unsuccessful, suggesting that failure was attributable to degradation of the controls formulated without liposomes rather than operator error. Each of the controls that were formulated with liposomes were successfully sequenced (FIG. 32 and Table 10).

TABLE 10

Sequencing results for refrigerated (2-8° C.) and stressed controls (42° C.)

| Time point (Temp) | Format | Chr13 | Chr18 | Chr21 | NCV X | NCV Y |
|---|---|---|---|---|---|---|
| Time 0 | Liposome | 21.1 | 0.24 | 0.0 | −12.32 | 46.48 |
| 47 Days (4° C.) | Liposome | 22.1 | 0.44 | 0.21 | −13.62 | 46.52 |
| 47 Days (42° C.) | Liposome | 21.5 | 0.61 | −0.90 | −13.97 | 44.95 |
| 125 Days (4° C.) | Liposome | 25.5 | 2.07 | 0.24 | −13.3 | 40.24 |
| 125 Days (42° C.) | Liposome | 25.9 | −0.03 | 0.09 | −12.87 | 41.68 |
| 47 Days (4° C.) | No Liposomes | Sample failed in library preparation | | | | |
| 47 Days (42° C.) | No Liposomes | Sample failed in library preparation | | | | |
| 125 Days (4° C.) | No Liposomes | Sample failed in library preparation | | | | |
| 125 Days (42° C.) | No Liposomes | Sample failed in library preparation | | | | |

Two samples were prepared according to Examples 4-6, one sample containing liposomes (1:2Css) and one sample prepared in parallel without liposomes (4:3Css). The samples were stored for 66 days at 42° C. and then analyzed on an Agilent Bioanalyzer. Bioanalyzer analysis was performed using the High Sensitivity DNA 1000 Assay, which was used to assess the stability by each control's fragmentation profile. The liposome-containing sample (1:2Css) displayed a peak centered at 150 bp, corresponding to sheared DNA (FIG. 15). The sample prepared without liposomes (4:3Css) did not display a peak at 150 bp, and instead displayed a sizable high molecular weight signal at >3000 bp, consistent with DNA aggregation (FIG. 15). Aggregation is consistent with the pronounced negative impact on the downstream library preparation procedures required as a part of sequencing (supra). Liposomes may therefore inhibit the aggregation of nucleic acids in a control.

Example 13: Neoplasm Controls

Controls were created for assessing the concentration of 9 mutations associated with various neoplasm.

The seven plasmids utilized for this experiment are listed in Table 11. Each plasmid (10 µg at 1 µg/µL) was digested with NotI at 37° C. for 3 hours. NotI was deactivated by a 20 min incubation at 65° C. The samples were then purified using the PCR Clean Up Kit by Qiagen and the samples were estimated to be at 196 ng/µL. The samples were quantitated by Nanodrop and dPCR (see Table 12). Determination of concentration of ng/µL by dPCR uses the ampicillin cartridge requires a large multiplication factor which is estimated, however, the use of this number for normalization of the plasmids is still valid. Each linearized plasmid was analyzed by gel electrophoresis to determine linearization efficiency.

TABLE 11

Plasmids utilized in the building of Seraseq ™ Circulating Tumor DNA-I Mutation Mix Kit (AF5-WT)

| Gene | Mutation | Type of Variant | COSMIC ID |
|---|---|---|---|
| BRAF | p.V600E | SNP | COSM476 |
| EGFR* | p.D770_N771insG | INDEL | COSM12378 |
| EGFR | p.E746_A750delELREA | INDEL | COSM6225 |
| EGFR* | p.T790M | SNP | COSM6240 |
| KIT | p.D816V | SNP | COSM1314 |
| KRAS | p.G12D | SNP | COSM521 |
| NRAS | p.Q61R | SNP | COSM584 |
| PIK3CA# | p.H1047R | SNP | COSM775 |
| PIK3CA# | p.N1068fs*4 | INDEL | COSM12464 |

*Genes on same plasmid
Genes on same plasmid

TABLE 12

Plasmid quantitation by Nanodrop and dPCR

| Gene | Mutation | COSMIC ID | Concentration by Nanodrop (ng/μL) | Concentration by dPCR (ng/μL) |
|---|---|---|---|---|
| BRAF | p.V600E | COSM476 | 170.9 | 261.6 |
| EGFR | p.E746_A750delELREA | COSM6225 | 191.0 | 218.3 |
| EGFR | p.T790M | COSM6240 | 176.0 | 263.0 |
| KIT | p.D816V | COSM1314 | 184.1 | 240.9 |
| KRAS | p.G12D | COSM521 | 23.4 | 25.7 |
| NRAS | p.Q61R | COSM584 | 182.6 | 254.7 |
| PIK3CA | p.H1047R | COSM775 | 165.9 | 218.7 |

The plasmids were normalized to 10 ng/μL in a final volume of 75 μL using MB Water. The master plasmid mix was diluted 5×1:20 or 1:3200000 in MB water and measured by dPCR. The concentration of each mutation was measured using dPCR (Table 13).

TABLE 13

Plasmid concentration after normalization using mutant specific genes.

| Gene | Mutation | COSMIC ID | Concentration by dPCR after dilution (copies/μL) | Concentration by dPCR of stock plasmid pool (copies/μL) |
|---|---|---|---|---|
| BRAF | p.V600E | COSM476 | 282.3 | 2.26E+09 |
| EGFR | p.E746_A750delELREA | COSM6225 | 310.2 | 2.48E+09 |
| EGFR | p.T790M | COSM6240 | 233.0 | 1.86E+09 |
| KIT | p.D816V | COSM1314 | 304.3 | 2.43E+09 |
| KRAS | p.G12D | COSM521 | 249.7 | 2.00E+09 |
| NRAS | p.Q61R | COSM584 | 262.0 | 2.10E+09 |
| PIK3CA | p.H1047R | COSM775 | 255.0 | 2.04E+09 |

The concentration of GM24385 gDNA going into the shearing process was approximately 150 ng/μL, in order to shear to ~170 bp using previously established shearing parameters. The first step in creating the product was to dilute the stock solution of GM24385 gDNA to 150 ng/μL. The gDNA was pooled and measured by Qubit using the High Sensitivity Kit. The concentration of GM24385 was 233.6 ng/μL. To make 11 mL of 150 ng/μL of stock gDNA, 7063.4 μL of GM24385 was diluted with 3936.6 μL of 0.1x TE pH 8.0, dPCR was performed after mixing with the plasmid master mix (see below) and the concentration of gDNA using the BRAF wt assay was 147.6 ng/μL.

"Rough dilutions" were first made by diluting the plasmid master mix into the 147.6 ng/μL GM24385 gDNA. The actual concentration of the dilution, measured by dPCR (SOP19195) and the BRAF primer set, was AF 59.6% and AF 0.11%. These rough dilutions were diluted further to AF 4.97% and AF 0.1075%.

The AF 4.97% became the AF 5% sample and used to make 2-fold serial dilutions to make the AF 1.25% and AF 0.625% samples. The AF 0.1075% dilution became the AF 0.1% sample and the 147.6 ng/μL GM24385 gDNA became the AF 0% sample. The final volume for all samples was 1.2 mL minimum, in order to take 1.0 mL through the shearing process. All of the samples were taken into shearing and filtering at this point. Verification of AF percentage was performed after shearing and filtering. Samples were diluted to 10 ng/μL and measured for AF % using dPCR and using primers against at least one gene per plasmid. During this verification step it was discovered that a calculation error was made. The error occurred with the AF 0.1075% sample, which was actually AF 1.075%. To rectify this, 40 μL of the sheared/filtered AF 1.075% was combined with 360 μL of the sheared/filtered AF 0% to make the AF 0.1% (a 1:10 dilution). This sample was retested by dPCR and was confirmed to be AF 0.1%. At this point all samples had a minimum of 300 μL which is the volume needed for liposome formation. The results from the dPCR assays are listed in Table 14 and graphically represented by FIG. 17.

TABLE 14

Allele frequency percentages (AF %) results from dPCR experiments on sheared/filtered ctDNA AF samples.

| Mutation name | BRAF p. V600E | EGFR p. E746_A750 delELREA* | EGFR p. T790M | KIT p. D816 V | KRAS p. G12D | NRAS Q61R | PIK3CA p. H1047R |
|---|---|---|---|---|---|---|---|
| Actual % for the AF 5.0% | 4.7 | 7.7 | 4.0 | 5.8 | 4.0 | 5.0 | 4.8 |
| Actual % for the AF 1.25% | 1.17 | 1.96 | 1.09 | 1.45 | 1.16 | 1.40 | 1.28 |
| Actual % for the AF 0.63% | 0.678 | 0.949 | 0.574 | 0.695 | 0.625 | 0.711 | 0.673 |
| Actual % for the AF 0.10% | 0.10 | 0.20 | 0.14 | 0.16 | 0.17 | 0.17 | 0.18 |
| Actual % for the AF 0% | 0.01 | 0.01 | 0.09 | 0.09 | 0.11 | 0.12 | 0.11 |

*The results of this assay are known to be slightly higher due to previous work. The high results are due to in INDEL bias (non-linear PCR amplification).

Following verification of the correct mutant plasmid mix to gDNA allele frequency (AF), 1000 µL of each AF was transferred to a milliTUBE (Covaris P/N:520130) for use in Covaris M220 with the milliTUBE holder (Covaris P/N: XT500348) to shear the nucleic acids. The following parameters were set up for the shear: Peak Power: 75.0, Duty Factor: 20.0, Cycles per Burst: 200, Time: 20 min. and Temperature: 4-8° C. Once a water bath was equilibrated to the set temperature, the milliTUBE was placed into the holder and the program was run. After each run, the sample was stored at 2-8° C.

DNA Analysis of the shearing fragment size was conducted via gel electrophoresis and using the Bioanalyzer. The agarose gel analysis was performed with 1.0% agarose. 150 ng of DNA was loaded per lane. The experiment showed that the genomic DNA was completed sheared and the agarose gel image is shown in FIG. 18. Additionally, FIG. 19 is a graph of the sheared gDNA peak size utilizing the Bioanalyzer High Sensitivity DNA Kit on an Agilent Bioanalyzer. The Bioanalyzer traces are shown in FIG. 19 with peak heights ranging between 150-170 bp.

Lipid Preparation

A 2.5% molar blend of DDAB (didodecyldimethylammonium bromide) in DMPC (1,2-dimyristoyl-sn-glycero-3-phosphocholine) lyophilized lipid blend was used for liposome preparation. This was achieved creating a physical mixture of 400 mg DMPC (Avanti Polar Lipids, P/N: 850345P) and 6.8 mg DDAB (Sigma, P/N: 359025). To get the proper mixture/formation of lipids, the lipids were dissolved in the solvent t-butyl alcohol and then lyophilized to remove the solvent.

6.8 mg was too small to weight and so a 68 mg/mL solution in t-butyl alcohol (Sigma, P/N: 471712-100 mL) was first made in a small glass vial. The density of t-butyl alcohol is different than water (775 mg/mL), and so the solvent was added gravimetrically. After the 68 mg/mL solution was made, 400 mg of DMPC was added to a small (50 mL) round bottom flask followed by 100 µL of the 68 mg/mL solution of DDAB. Then 10 mL of t-butyl alcohol (7.75 g) was added gravimetrically to the flask and the lipids were dissolved with sonication and heat. Use of a heat gun on the glass pipet tip was necessary to prevent freezing of the glass pipette. Following dissolution, the round bottom flask was placed under mild vacuum and flash frozen in liquid nitrogen. Solvent was removed under vacuum. After drying overnight (~19 hours), the vacuum was released and the resultant solid was observed as a flocculent white solid. The material was briefly vortexed to release the flakes from the side of the glass wall. The material was capped with a rubber stopper and used as is.

An aliquot of 20 mg of cationic lipids was transferred into each of five 1.7 mL microcentrifuge tubes. The tubes were rehydrated with 100 µL of warmed (40° C.) lx TE pH 8.0. The tubes were sonicated in a warmed (~40° C.) water bath sonicator for 20 min.

DNA Encapsulation

Prior to encapsulation, 1000 µL of each of the five sheared DNA mixture was filtered through a 0.1 µm Durapore PVDF filter (Millipore P/N: UFC30VV00) at 12,000×g until dry to remove any large particulates which may foul the extrusion membrane. 300 µL of sheared and filtered DNA was added to the microcentrifuge tube of prepared lipid. After vortexing, the tubes were dipped into liquid nitrogen so that the volume of liquid was submerged, but not the lid, for 30-60 seconds. Once the tubes were entirely frozen, they were quickly placed onto a 40° C. heat block for 15-20 min. After the thaw period, the tubes were vortexed thoroughly. The freeze/thaw cycle was repeated for a total of five times.

Liposome Extrusion

An Avanti Mini-extruder (Avanti Polar Lipids, Inc; P/N 610000) was used for the extrusion process following to extrude each tube of encapsulated sheared DNA. For this, the entire lipid/DNA preparation, ~0.4 mL, was drawn into one side of the mini-extruder and processed for a total of 31 passages using 0.1 µm extrusion membrane (Whatman P/N: 800309). The final material was transferred into a new, 1.7 mL microcentrifuge tubes and the volume was brought to 1 mL with 1×TE pH 8.0.

Liposome Purification

Extruded liposomes were purified over a HiTrap 5 mL DEAE FF column (GE P/N: 17-5154-01) on the AKTA Explorer FPLC using manual injection and the "5 mL loop liposome" method. All 1 mL of liposome was injected and 2 minutes of elution was collected, resulting in a 4 mL "high titer" liposome bulk solution. Buffer A, which is used as the wash buffer, was 50 mM Tris Buffer made from 1.0 M Tris-HCl Buffer, pH 7.5 (Quality Biological P/N: 351-006-721). Buffer B, which is used as the elution buffer, was 1x TBS with 1 M NaCl and made from TBS and NaCl.

Formulation 50% MatriBase

The 50% MatriBase solution was made from a 1:1 formulation of 2 mM EDTA (Amresco P/N: 0245-500G), 0.18% sodium azide (Sigma S2002), PicoPure water, and Seracon MatriBase (SeraCare P/N: 22009). To prepare this formulation, an analytical balance was used to measure 2.7 g of sodium azide and 1.14 g of EDTA, which were transferred to a 3 L container and 1.5 L of water was added and the contents thoroughly mixed. A portion of 1.5 L of MatriBase was then added and mixed again. Finally, the 50% Seracon MatriBase mix was filtered through a 0.22 μm filter (Nalgene P/N: 430186) and stored at 2-8° C. until further use. This results in a final formulation of 50% MatriBase with 1 mM EDTA and 0.09% sodium azide. The final bulk size was 3000 mL.

Liposome Bulk Testing, Dilution to Intermediate Stock and Final Bulk

The high titer solution was aggressively vortexed and 10 μL of the LipoDNA bulk was extracted using the QIAamp Circulating Nucleic Acid Kit. Prior to extraction a 1:100 dilution was performed: 10 μL liposome aliquot was diluted in 1000 μL of 50% MatriBase bulk. Single extractions were performed and the final column elution was performed with 50 μL of AVE buffer from the kit. Triplicate Qubit assays were conducted on its extracted volume using the Qubit High Sensitivity (HS) Assay Kit (PN Q32851). From this, the concentration of the high-titer bulk was determined (Table 15).

Based on this data of Table 15, an intermediate bulk was prepared according to Table 16 ("Target intermediate Conc") below with a target concentration of 0.1 μg/mL and a volume of 80 mL intermediate bulk. Samples were prepared by addition of the specified HT stock to 80 mL of 50% MatriBase. A portion of 1 mL of the intermediate bulk was mixed with 1 mL Ultrapure water and extracted using the QIAamp Circulating Nucleic Acid Kit. This was done in duplicate. Following duplicate extractions, the final column elution was performed with 50 μL of AVE buffer from the kit. Triplicate Qubit assays were conducted on its extracted volume using the Qubit High Sensitivity (HS) Assay Kit (PN Q32851). From this, the concentration of the high-titer bulk was determined, table below Table 16.

TABLE 16

DNA yield after dilution to an intermediate concentration after extraction.

| Sample | Conc. Lipo Bulk (μg/mL) | Target intermediate Conc. (μg/mL) | Intermediate volume (mL) | Vol. of HT stock (mL) | Measured concentration μg/mL |
|---|---|---|---|---|---|
| 0% AF | 4.5 | 0.1 | 80 | 1.777778 | 0.199 |
| 0.1% AF | 7.55 | 0.1 | 80 | 1.059603 | 0.188 |
| 0.63% AF | 6.4 | 0.1 | 80 | 1.25 | 0.197 |
| 1.25% AF | 7.2 | 0.1 | 80 | 1.111111 | 0.150 |
| 5% AF | 7.7 | 0.1 | 80 | 1.038961 | 0.177 |

Final stock was formulated with a target concentration of 0.016 μg/mL from the intermediate bulks and 50% MatriBase formulation according to table 17 below. From the final 500 mL finished bulks, 3 aliquots of 5 mL was sampled from each and extracted (without dilution) using the QIAamp Circulating Nucleic Acid Kit. Triplicate extractions were performed and the final column elution was performed with 50 μL of AVE buffer from the kit. Triplicate Qubit assays were conducted on its extracted volume using the Qubit High Sensitivity (HS) Assay Kit. The average concentration from Qubit was multiplied by 0.050 mL to get the total μg of DNA extracted. Afterwards the total DNA extracted is divided by the 5000 μL, the volume of the Matribase extracted. From this, the final bulk concentration was assigned (Table 17). All of the concentrations met specification.

TABLE 15

DNA yield from undiluted liposomes after extraction

| Sample | Conc. extract μg/mL | Volume extract mL | Volume LipoBulk for extract mL | Conc. LipoBulk μg/mL | Total bulk volume mL | DNA yield μg | Recovery |
|---|---|---|---|---|---|---|---|
| 0% AF | 0.9 | 0.05 | 0.01 | 4.5 | 4 | 18 | 40% |
| 0.1% AF | 1.51 | 0.05 | 0.01 | 7.55 | 4 | 30.2 | 67% |
| 0.63% AF | 1.28 | 0.05 | 0.01 | 6.4 | 4 | 25.6 | 57% |
| 1.25% AF | 1.44 | 0.05 | 0.01 | 7.2 | 4 | 28.8 | 64% |
| 5% AF | 1.54 | 0.05 | 0.01 | 7.7 | 4 | 30.8 | 68% |
| Average | 1.32 | 0.05 | 0.01 | 6.61 | 4 | 26.4 | 59% |

TABLE 17

Final DNA yield after final formulation after extraction.

| Sample | Extract 1 (µg/mL) | Extract 2 (µg/mL) | Extract 3 (µg/mL) | Average concentration in 50 µL extraction volume (µg/mL) | CV | Total extracted DNA divided by the input volume of 5 mL (ng/mL) | ng per 5 mL |
|---|---|---|---|---|---|---|---|
| 0% AF | 1.41 | 1.46 | 1.30 | 1.39 | 6% | 13.9 | 70 |
| 0.1% AF | 1.68 | 1.82 | 1.42 | 1.64 | 12% | 16.4 | 82 |
| 0.63% AF | 1.74 | 1.93 | 1.96 | 1.88 | 6% | 18.8 | 94 |
| 1.25% AF | 1.11 | 1.54 | 1.30 | 1.32 | 16% | 13.2 | 66 |
| 5% AF | 1.53 | 1.31 | 1.31 | 1.38 | 9% | 13.8 | 69 |

Final bulk extracts were sequenced using the amplicon-based Swift 56G oncology panel (NGS) assay which was designed for cfDNA. The goal of the experiment was to verify that sequenceable material is present in the finished bulk and that samples had not been interchanged during preparation. Reliable allele frequency calls are not expected below 5% with this library kit and are presented for qualitative, rather than quantitative evaluation.

For sequencing library preparation, 10 µL of Extract 1 & Extract 2 for each reference material was used as the input. Samples were prepared according to manufacturer's instructions for the 56G Oncology Panel (Swift Biosciences, Cat. No. AL-IL56G-12/48). Prepared libraries were quantified via qPCR (KAPA Biosystems, Cat. No. KK4824) on an ABI 7500 RT-PCR instrument (Table 18). Libraries were then normalized and pooled together. Pooled libraries were denatured and run for 300 cycles using v2 chemistry (Illumina, Cat. No. MS-102-2002) on a MiSeq according to manufacturer's instructions.

TABLE 18

Sequencing of Neoplasm controls

| Sample (and allelic frequency) | Library Conc. (nM) by QPCR | Targeted Loading Conc. (pM) | SeraCare Accession # | Number of reads obtained |
|---|---|---|---|---|
| A1 -- 0.6% | 2.3 | 12 | 2016-016 | 611823 |
| A2 -- 0.6% | 3.0 | 12 | 2016-017 | 670586 |
| B1 -- 0.6% | 2.8 | 12 | 2016-018 | 475269 |
| B2 -- 0.6% | 3.4 | 12 | 2016-019 | 726787 |

TABLE 18-continued

Sequencing of Neoplasm controls

| Sample (and allelic frequency) | Library Conc. (nM) by QPCR | Targeted Loading Conc. (pM) | SeraCare Accession # | Number of reads obtained |
|---|---|---|---|---|
| C1 -- 0.6% | 1.9 | 12 | 2016-020 | 783916 |
| C2 -- 0.6% | 2.7 | 12 | 2016-021 | 799842 |
| D1 -- 1.25% | 3.1 | 12 | 2016-022 | 737419 |
| D2 -- 1.25% | 2.4 | 12 | 2016-023 | 627749 |
| F1 -- 5% | 2.1 | 12 | 2016-024 | 509749 |
| F2 -- 5% | 2.2 | 12 | 2016-025 | 1022600 |
| C1 -- 0.6% | 1.9 | 12 | 2016-020_2 | 1824592 |
| C2 -- 0.6% | 2.7 | 12 | 2016-021_2 | 2645581 |
| D1 -- 1.25% | 3.1 | 12 | 2016-022_2 | 3421848 |
| D2 -- 1.25% | 2.4 | 12 | 2016-023_2 | 2615234 |
| F1 -- 5% | 2.1 | 12 | 2016-024_2 | 2212878 |
| F2 -- 5% | 2.2 | 12 | 2016-025_2 | 2313339 |

Samples A-F were library prepped as a set, however, library preparation of D1 and D2 was repeated because of variable quantitation following library preparation. Samples A-F (10 libraries) were sequenced on a single MiSeq flow cell. Because of variable AF calls between certain replicates, Samples F, D, and C (6 libraries) were re-sequenced on a second single flow cell to achieve a higher read depth. Results table for Run 1 and Run 2 with summary plots to follow (Table 19). Data was also collected on un-liposomed 5% sheared DNA blend bulk. Table 20 shows that AF calls before and after liposoming and extraction are comparable and that the SeraCare Variant caller results in comparable calls to Swifts variant calling pipeline.

TABLE 19

Results of Swift 56G oncology panel with data processing on SeraCare Variant processor

A.

| Sample | F2-Run1 | F2-Run2 | F1-Run1 | F1-Run2 | D2-Run1 | D2-Run2 | D1-Run1 | D1-Run2 |
|---|---|---|---|---|---|---|---|---|
| TARGET AF | 5% | 5% | 5% | 5% | 1.25% | 1.25% | 1.25% | 1.25% |
| BRAF(476) | 6.5% | 5.2% | 5.9% | 5.8% | 1.3% | 2.0% | 0.9% | 1.0% |
| EGFR(6240) | 5.1% | 5.0% | 6.5% | 6.2% | 0.3% | 0.1% | 7.9% | 6.8% |
| EGFR(12378) | 5.0% | 5.0% | 6.5% | 6.2% | 0.3% | 0.0% | 7.9% | 6.7% |
| PIK3CA(775) | 3.5% | 2.8% | 4.2% | 4.5% | 1.3% | 1.3% | 0.5% | 0.4% |
| PIK3CA(12464) | 6.2% | 6.4% | 6.2% | 6.3% | 1.4% | 1.2% | 0.7% | 0.8% |
| NRAS(584) | 5.1% | 5.0% | 6.4% | 5.8% | 1.8% | 1.9% | 2.3% | 2.3% |
| KRAS(521) | 5.0% | 4.4% | 3.3% | 4.0% | 0.7% | 0.6% | 1.5% | 1.1% |
| KIT(1314) | 5.9% | 5.7% | 6.5% | 7.2% | 1.2% | 1.1% | 1.0% | 1.1% |
| EGFR(6225) | 4.2% | 4.0% | 4.4% | 3.8% | 1.0% | 0.8% | 1.8% | 2.0% |
| Average | 5.2% | 4.8% | 5.6% | 5.6% | 1.0% | 1.0% | 2.7% | 2.5% |

TABLE 19-continued

Results of Swift 56G oncology panel with data processing on SeraCare Variant processor

| Sample | B. | | | | | | | |
|---|---|---|---|---|---|---|---|---|
| | C2-Run1 | C2-Run2 | C1-Run1 | C1-Run2 | B2-Run1 | B1-Run2 | A2-Run1 | A1-Run2 |
| TARGET AF | 0.63% | 0.63% | 0.63% | 0.63% | 0.1% | 0.1% | 0% | 0% |
| BRAF(476) | 0.1% | 0.0% | 0.0% | 0.7% | 0.1% | 0.2% | 0.2% | 0.3% |
| EGFR(6240) | 0.2% | 0.2% | 0.0% | 0.2% | 0.1% | 0.1% | 0.0% | 0.0% |
| EGFR(12378) | 0.2% | 0.2% | 0.0% | 0.2% | 0.1% | 0.1% | 0.0% | 0.0% |
| PIK3CA(775) | 0.9% | 0.7% | 0.7% | 0.7% | 0.0% | 0.4% | 0.0% | 0.1% |
| PIK3CA(12464) | 0.6% | 0.6% | 0.6% | 0.4% | 0.0% | 0.1% | 0.1% | 0.1% |
| NRAS(584) | 0.5% | 0.5% | 0.7% | 1.1% | 0.2% | 0.0% | 0.0% | 0.2% |
| KRAS(521) | 0.1% | 0.2% | 0.5% | 0.7% | 0.4% | 0.0% | 0.0% | 0.0% |
| KIT(1314) | 1.2% | 1.1% | 0.0% | 0.0% | 0.0% | 0.1% | 0.0% | 0.0% |
| EGFR(6225) | 0.3% | 0.3% | 0.3% | 0.2% | 0.0% | 0.0% | 0.0% | 0.1% |
| Average | 0.46% | 0.41% | 0.31% | 0.48% | 0.09% | 0.11% | 0.06% | 0.08% |

TABLE 20

5% AF sample and analysis comparison with Swift 56G assay

| Sample | Analysis Method | | |
|---|---|---|---|
| | SeraCare 5% AF RM | SeraCare 5% AF Mut. Mix | Swift Pipeline 5% AF Mut. Mix |
| BRAF(476) | 5.5% | 4.8% | 4.8% |
| EGFR(6240) | 5.6% | 5.6% | 4.3% |
| EGFR(12378) | 5.6% | 5.6% | 4.3% |
| PIK3CA(775) | 3.7% | 4.4% | 4.3% |
| PIK3CA(12464) | 6.4% | 5.6% | 5.5% |
| NRAS(584) | 5.4% | 4.5% | 4.5% |
| KRAS(521) | 4.2% | 3.6% | 3.6% |
| KIT(1314) | 6.4% | 4.8% | 4.7% |
| EGFR(6225) | 3.9% | 4.6% | 4.6% |
| average | 5.2% | 4.8% | 4.5% |
| SD | 1.0% | 0.7% | 0.5% |

Conclusions:

The reference material formulated at 5% performed as expected an average AF of 5.4%±1.1 (Run 1) and 5.2±1.1 (Run 2). In the 1.25% AF frequency sample, the quality of the data erodes, but the average allele frequency is still consistent with the target: 1.9%±1.9 (Run 1) and 1.7±1.9 (Run 2). Interestingly, in one of the 1.25% AF replicates EGFR(6240) and EGFR(12378), which are on the same plasmid, are skewed inordinately high at ~7% AF and most likely result from a low complexity library preparation. Samples with AF of 0.6%, 0.1% and 0% (WT) are in the noise of the assay, when individual mutations considered, however, the average allele frequency across a given sample a linear relationship (R=0.9656) is observed for 5% to 0.1%. Further, the reference material is unchanged through the liposoming process and extraction, and the SeraCare Variant caller produces comparable calls to Swift's in-house pipeline. Based on this data the controls are considered to be conforming and within specification.

Example 14: Trisomy Controls

Three 12% fetal fraction to maternal fraction DNA was made based on ddPCR concentration data for each of the three Trisomic DNAs. For each mixture, 12.6 μg of male Trisomic gDNA (described in Example 3, supra) was mixed with 92.4 μg of genomic DNA from peripheral blood mononuclear cells (PBMCs), and diluted with 1x TE pH 8.0 to 700 μL. Trisomy 13 genomic DNA, Trisomy 18 genomic DNA, and Trisomy 21 genomic DNA were derived from male Trisomy cell lines licensed from UCSF (see Example 3, supra). The maternal genomic DNA was derived from PBMCs. In order to create a 700 μL final volume of fetal and maternal gDNA mixture, the amounts of gDNA stock and buffer (lx TE, pH 8.0) used are show in Table 21. For example, for Trisomy 13, 47 μL of T13 gDNA, 184 μL of PBMC gDNA, and 469 μL of buffer was mixed together to achieve a concentration of 150 μg/mL in 700 μL. Once mixed, gel electrophoresis was performed with 0.6% agarose with a DNA loading amount of 150 ng per lane (FIG. 22), and droplet digital PCR was performed to analyze fetal fraction (Table 21). Target fetal fraction was 12±3%, which was achieved in all three Trisomy mixes.

TABLE 21

Trisomic hTPC Lines

| Cell Type | Sample name | Aneuploidy | Gestational Age (week) | Karyotype | Passage # |
|---|---|---|---|---|---|
| Trophoblast Progenitor | T13 C2 | Trisomy 13 | 16.1 | 47 XX +13 | P6 |
| Trophoblast Progenitor | T18 C1 | Trisomy 18 | 15.4 | 47 XY +18 | P5 |
| Trophoblast Progenitor | T21 C3 | Trisomy 21 | 15 | 47 XX +21 | P6 |

TABLE 22

Mixture of maternal and fetal gDNA based on ddPCR concentration.

| | Concentration | μg required | μL DNA Stock | μL buffer | Cross check μg/mL |
|---|---|---|---|---|---|
| PBMC | 501.50 | 92.4 | 184 | N/A | |
| T13 | 267.40 | 12.6 | 47 | 469 | 150 |
| T18 | 177.90 | 12.6 | 71 | 445 | 150 |
| T21 | 477.20 | 12.6 | 26 | 489 | 150 |

TABLE 23

Calculated fetal fraction in 12% blends based on ddPCR concentration and copy numbers.

|  | Concentration | Copies/2 | Concentration/(Copies/2) | Fetal Fraction |
|---|---|---|---|---|
| T13 | 75.275 | 752.25 | 0.1001 | 10.01% |
| T18 | 69.85 | 749.75 | 0.0932 | 9.32% |
| T21 | 69.75 | 737.25 | 0.0946 | 9.46% |

Trisomic and PBMC DNA was mixed, and 680 μL of solution was transferred to a milliTUBE (Covaris P/N: 520130) for use in Covaris M220 with the milliTUBE holder (Covaris P/N: XT500348). The following parameters were set up for the shear: Peak Power: 60.0, Duty Factor: 20.0, Cycles per Burst: 200, Time: 40 minutes, and Temperature: 4-8° C. A water bath was equilibrated to the set temperature, the milliTUBE was placed into the holder, and the shearing program was run. After each run, the Trisomy sheared mixes were stored at 2-8° C. until the next day. Testing was conducted on the sheared DNA using an Agilent Bioanalyzer and a Qubit 3.0 Fluorometer. DNA Analysis was conducted with the High Sensitivity DNA Kit on the Agilent Bioanalyzer (FIG. 23). Concentration was detected on the Qubit 3.0 with the Qubit Broad Range Assay Kit (Thermo P/N: Q32850).

Lipid Preparation

For liposome preparation, a 2.5% molar blend of lyophilized DDAB (didodecyldimethylammonium bromide) in DMPC (1,2-dimyristoyl-sn-glycero-3-phosphocholine) was used. This was achieved creating a physical mixture of 400 mg DMPC (Avanti Polar Lipids, P #8500345P) and 6.8 mg DDAB (Sigma, P #359025), which was added as a 68 mg/mL solution in t-butyl alcohol (Sigma, P #471712-100 mL) in a 50 mL round bottom flask. A portion of 10 mL to t-butyl alcohol was added gravimetrically to the flask and the lipids were dissolved with sonication. Following dissolution, the round bottom flask was placed under mild vacuum and flash frozen in liquid nitrogen. Solvent was removed under vacuum. After 19 hours of drying, the vacuum was released and the resultant solid was observed as flocculent white solid.

A 40 mg measure of cationic lipids (2.5% DDAB in DMPC) was transferred into a sterile 1.7 mL microcentrifuge tube. This was repeated for a total of three times for each control. Each tube was rehydrated with 200 μL of warmed (40° C.) lx TE pH 8.0. Tubes were then placed into a warmed (40° C.) bath sonicator and sonicated for 20 minutes.

DNA Encapsulation

Prior to encapsulation, 6100, of sheared DNA mixture was filtered through a 0.1 μm Durapore PVDF filter (Millipore P/N: UFC30VV00) at 12,000×g until dry to remove any large particulates that could foul the extrusion membrane. A portion of 600 μL of sheared and filtered DNA of each trisomy mix was added separately to each of the three prepared lipid tubes. After vortexing, the three tubes were dipped into liquid nitrogen so that the volume lines were submerged for 30-60 seconds. Once the tubes were entirely frozen, they were quickly placed onto a 40° C. heat block for 15-20 minutes. After the thaw period, the tubes were thoroughly vortexed. This freeze/thaw cycle was repeated a total of five (5) times.

Liposome Extrusion

A steel high-pressure extruder was used with argon gas at 300 psi to extrude each tube of encapsulated sheared DNA for a total of 10 passages, using two, sandwiched 0.1 μm filters (Whatman P/N:100405) and a 13 mm mesh spacer into a sterile 15 mL conical tube. Once extruded, 400 μL of 1× TE, pH 8.0 was added to each tube. The three conical tubes were then stored at 4-8° C. overnight.

Liposome Purification

Extruded liposomes were purified over a HiTrap 5 mL DEAE FF column (GE P/N: 17-5154-01) on the AKTA Explorer FPLC using manual injection and the '5 mL loop liposome' method. All 1 mL of liposome was injected and 2 minutes of elution was collected, resulting in a 4 mL "high titer" liposome bulk solution. The wash buffer was 50 mM Tris Buffer made from 1.0 M Tris Buffer, pH 8.0 (Millipore P/N: 648314). The elution buffer was 1× TBS with 1M NaCl, made from TBS and NaCl.

Liposome Bulk Testing and Dilution

The high titer solutions were aggressively vortexed, and 5 μL of each LipoDNA was bulk extracted using the QIAamp circulating nucleic acid kit. Prior to extraction, 5 μL liposome aliquots were diluted to 995 μL with 1× TE, pH 8.0. Extractions were performed in duplicate. Triplicate Qubit assays were conducted on the extracted volumes using the Qubit High Sensitivity (HS) Assay Kit. The concentration of the high-titer bulk was determined. Based on these results, high titer samples were diluted to 20 ng/mL according to Table 24 into 50% Seracon MatriBase mixture. The 50% Seracon MatriBase (MB) mixture was made from a 1:1 formulation of 2 mM EDTA (Amresco P/N: 0245), 0.18% sodium azide, Ultrapure water and Seracon MatriBase (SeraCare P/N: 22009). The 50% Seracon MatriBase mix was filtered through a 0.2 μm filter (Nalgene P/N:567-0020) prior to addition of liposome. This results in a final formulation of 50% MatriBase with 1 mM EDTA and 0.09% sodium azide. Final bulk size was made to be 200 mL. All dilutions were completed aseptically in a biosafety cabinet hood.

TABLE 24

Qubit analysis of Trisomy liposome concentrations.

| Trisomy | Conc. of extracted solution {ng/μL} | Volume of extract {μL} | Volume of bulk {μL} | Conc. of bulk {ng/μL} | Target concentration of finished bulk {ng/pL} | Required volume of bulk {μL} | Quantity bulk required for finished bulk {μL} |
|---|---|---|---|---|---|---|---|
| 13 | 1.125 | 50 | 5 | 11.3 | 0.02 | 200000 | 356 |
| 18 | 0.891 | 50 | 5 | 8.9 | 0.02 | 200000 | 449 |
| 21 | 0.685 | 50 | 5 | 6.9 | 0.02 | 200000 | 584 |

The Finished 20 ng/mL bulk was extracted using a QIAamp circulating nucleic acid extraction kit. Aliquots of 1 mL of each Trisomy were extracted in duplicates using the Qubit HS Assay. Final concentrations measured using the Qubit assay are shown in Table 25.

TABLE 25

Qubit analysis of final bulk concentrations.

| Trisomy | ng/mL |
|---|---|
| T13 | 21.75 |
| T18 | 22.58 |
| T21 | 24.67 |

A single, 190 mL unit of diluted bulk of the Trisomy 13 control was analyzed. Three replicate aliquots of 1.0 mL were prepared from the same bulk and shipped to a commercial laboratory for NIPS testing analysis using an adapted Verinata Health assay using a V.4 chemistry on an Illumina HiSeq. Samples were independently extracted and taken through library preparation. A table of Normalized Chromosome Value (NCV) scores is shown below (Table 26) and Chromosomes 13, 18, & 21 values are plotted in a bar graph in FIG. 24. Subsequently, identity was confirmed by a different commercial laboratory running an analogous assay on the Illumina HiSea platform.

TABLE 26

Normalized Chromosome Value (NCV) scores for Trisomy 13 controls

| Identifier | Chr13 | Chr18 | Chr21 | NCV X | NCV Y |
|---|---|---|---|---|---|
| C75RAANXX-L8-425-76A-A-rerun | 19.606 | −2.034 | 0.712 | −12.685 | 42.307 |
| C75RAANXX-L8-425-76A-G -rerun | 15.934 | −0.593 | 3.273 | −16.705 | 39.520 |
| C75RAANXX-L8-425-76A-H-rerun | 18.942 | −0.781 | 1.073 | −17.744 | 41.995 |

| Identifier | Chr13 | Chr18 | Chr21 | Fetal Fraction |
|---|---|---|---|---|
| 13T13 | 24.41 | 0.17 | −2.34 | 12.8% |

A single, 190 mL unit of diluted bulk of the Trisomy 18 control was analyzed. Three replicate aliquots of 1.0 mL were prepared from the same bulk and shipped to a commercial laboratory for NIPS testing analysis using an adapted Verinata Health assay using a V.4 chemistry on an Illumina HiSeq. Samples were independently extracted and taken through library preparation. A table of Normalized Chromosome Value (NCV) scores is shown below (Table 27) and Chromosomes 13, 18, & 21 values are plotted in a bar graph in FIG. 25. Subsequently, identity was confirmed by a different commercial laboratory running an analogous assay on the Illumina HiSeq platform.

TABLE 27

Normalized Chromosome Value (NCV) scores for Trisomy 18 controls

| Identifier | Chr13 | Chr18 | Chr21 | NCV X | NCV Y |
|---|---|---|---|---|---|
| C75RAANXX-L8-425-76A-C-rerun | −0.200 | 16.404 | 1.071 | −13.651 | 39.474 |
| C75RAANXX-L8-425-76A-E-rerun | 0.188 | 15.978 | 0.757 | −14.260 | 39.856 |
| C75RAANXX-L8-425-76A-F-rerun | 1.288 | 16.296 | 2.942 | −16.476 | 40.235 |

| Identifier | Chr13 | Chr18 | Chr21 | Fetal Fraction |
|---|---|---|---|---|
| 18T18 | 2.20 | 20.52 | −0.90 | 13.3 |

A single, 190 mL unit of diluted bulk of the Trisomy 21 control was analyzed. Three replicate aliquots of 1.0 mL were prepared from the same bulk and shipped to a commercial laboratory for NIPS testing analysis using an adapted Verinata Health assay using a V.4 chemistry on an Illumina HiSeq. Samples were independently extracted and taken through library preparation. A table of Normalized Chromosome Value (NCV) scores is shown below (Table 28) and Chromosomes 13, 18, & 21 values are plotted in a bar graph in FIG. 26.

TABLE 28

Normalized Chromosome Value (NCV) scores for Trisomy 18 controls

| Identifier | Chr13 | Chr18 | Chr21 | NCV X | NCV Y |
|---|---|---|---|---|---|
| C75RAANXX-L8-425-76B-A | 0.058664 | −1.49281 | 11.70983 | −13.093 | 36.73143 |
| C75RAANXX-L8-425-76D-A | −0.05974 | −0.28758 | 12.05003 | −14.6612 | 42.39498 |
| C75RAANXX-L8-425-76J-A | 2.418117 | −1.19752 | 12.69027 | −15.7939 | 39.77527 |

Example 15: Trisomy 21 Controls

Trisomy 21 Controls were prepared according to Example 14, with target aneuploid DNA to total DNA concentrations of 1%, 2%, 4%, and 8%. The final controls had DNA concentrations ranging of 27.2 ng/mL (1% trisomy 21 aneuploid control), 26.8 ng/mL (2%), 27.9 ng/mL (4%), and 27.3 ng/mL (8%).

Three replicate aliquots from each trisomy 21 control were shipped to a commercial laboratory for NIPS testing analysis using an adapted Verinata Health assay using a V.4 chemistry on an Illumina HiSeq. Samples were independently extracted and taken through library preparation. Because of analysis complications at the laboratory, samples of 1% and 2% fetal fraction were processed on a different flow cell and in a non-parallel library preparation from samples of 4% and 8% fetal fraction.

The reported NCV values for chromosomes 13, 18, 21, X, & Y values are listed in Table 29 with average values and standard deviations listed in Table 30. FIGS. 27 and 28 demonstrate the expected linear relationship ($R^2=0.9992$) between NCV Y and NCV 21 and the corresponding baseline noise levels for associated with chromosome 13 and chromosome 18.

FIG. 29 confirms the linear relationship of the between the fetal fraction determined by dPCR and the NCV measurement for chromosome Y ($R^2=0.9954$) and chromosome 21 ($R^2=0.9956$).

TABLE 29

Individual NCV Values

|  | Chr13 | Chr18 | Chr21 | NCV X | NCV Y |
|---|---|---|---|---|---|
| T21 1% | 0.61 | 0.66 | 2.17 | −3.29 | 5.01 |
| T21 1% | 1.97 | 1.83 | 1.58 | −3.49 | 4.75 |
| T21 1% | 1.06 | 0.95 | 1.69 | −3.60 | 4.06 |
| T21 2% | 0.18 | 1.54 | 2.73 | −4.64 | 8.44 |
| T21 2% | 0.66 | 0.59 | 3.78 | −4.95 | 7.52 |
| T21 2% | 0.53 | −0.45 | 2.86 | −4.46 | 7.44 |
| T21 4% | 0.55 | 0.84 | 5.24 | −6.17 | 13.47 |
| T21 4% | 0.65 | 1.05 | 6.43 | −5.89 | 13.96 |
| T21 4% | 0.48 | −0.17 | 4.91 | −6.50 | 13.45 |
| T21 8% | 1.64 | 0.93 | 10.16 | −10.13 | 28.98 |
| T21 8% | 1.32 | −0.68 | 11.38 | −9.57 | 28.20 |
| T21 8% | 2.25 | 0.42 | 12.26 | −9.61 | 29.54 |

TABLE 30

Average NCV Scores and Standard Deviation

|  | Chr13 | Chr18 | Chr21 | NCV X | NCV Y | FF by dPCR† |
|---|---|---|---|---|---|---|
| Average NCV |  |  |  |  |  |  |
| 1% FF average | 1.21 | 1.15 | 1.81 | −3.46 | 4.61 | 1.1 |
| 2% FF average | 0.45 | 0.56 | 3.12 | −4.68 | 7.80 | 2.1 |
| 4% FF average | 0.56 | 0.57 | 5.53 | −6.19 | 13.63 | 4.2 |
| 8% FF average | 1.74 | 0.22 | 11.27 | −9.77 | 28.91 | 8.5 |
| StdDev in NCV |  |  |  |  |  |  |
| 1% FF SD | 0.69 | 0.61 | 0.31 | 0.16 | 0.49 |  |
| 2% FF SD | 0.253 | 0.99 | 0.57 | 0.25 | 0.56 |  |
| 4% FF SD | 0.09 | 0.65 | 0.80 | 0.30 | 0.29 |  |
| 8% FF SD | 0.47 | 0.82 | 1.06 | 0.31 | 0.67 |  |

†dPCR data is described in detail in the primary PBR for this product
FF = fetal fraction

Example 16: Multi-Analyte Trisomy Controls

A sample comprising 12% trisomy 21 genomic DNA, 12% trisomy 18 genomic DNA, 12% trisomy 13 genomic DNA, and 64% non-aneuploid female DNA (from PBMCs) was prepared according to the methods of Example 14. A single, 190 mL unit of the Multi-Analyte Trisomy control was analyzed. Three replicate aliquots of 1.0 mL were prepared from the same bulk and shipped to a commercial laboratory for NIPS testing analysis using an adapted Verinata Health assay using a V.4 chemistry on an Illumina HiSeq. Samples were independently extracted and taken through library preparation. A table of Normalized Chromosome Value (NCV) scores is shown below (Table 31) and Chromosomes 13, 18, & 21 values are plotted in a bar graph in FIG. 30.

TABLE 31

Positive identification all three trisomies were detected in the Multi-Analyte Trisomy Control

| Identifier (flow cell ID not provided) | Chr13 | Chr18 | Chr21 | NCV X | NCV Y |
|---|---|---|---|---|---|
| 425-82-A | 21.71 | 21.98 | 13.55 | −32.26 | 140.70 |
| 425-82-B | 21.60 | 22.91 | 12.81 | −32.45 | 140.14 |
| 425-82-C | 20.84 | 22.00 | 12.44 | −32.85 | 139.89 |

Example 17: Trisomy Negative Control (Euploid Control)

A sample comprising approximately 17.8% male genomic DNA, derived from PBMCs, and approximately 82.2% female genomic DNA, derived from PBMCs was prepared according to the methods in Example 14. A single, 190 mL unit of the Trisomy negative control was analyzed. Three replicate aliquots of 1.0 mL were prepared from the same bulk and shipped to a commercial laboratory for NIPS testing analysis using an adapted Verinata Health assay using a V.4 chemistry on an Illumina HiSeq. Samples were independently extracted and taken through library preparation. The analysis was confirmed by a different commercial laboratory running an analogous assay on the Illumina HiSeq platform. A table of Normalized Chromosome Value (NCV) scores is shown below (Table 32).

TABLE 32

Normalized Chromosome Value (NCV) analysis of a Trisomy Negative Control

| Identifier | Chr13 | Chr18 | Chr21 | NCV X | NCV Y |
|---|---|---|---|---|---|
| 425-94-R | 0.20 | 0.92 | −0.18 | −18.66 | 69.97 |

| Identifier | Chr13 | Chr18 | Chr21 | Fetal Fraction |
|---|---|---|---|---|
| 1EUPLO1 | 1.10 | 0.73 | 1.63 | 13.0% |

Example 18: Controls Comprising Pegylated Liposomes

DNA containing liposomes were formulated using polyethylene glycol-modified lipids (pegylated lipids). The liposomes comprised mPEG2000-DMPE (1,2-dimyristoyl-sn-glycero-3-phosphoethanolamine-N4methoxy(polyethyleneglycol) 2000D, DMPC (1,2-dimyristoyl-sn-glycero-3- phosphocholine), and DDAB (didodecyldimethylammonium bromide) at 0.05:1:0.025 molar ratios. The mPEG2000-DMPE:DMPC:DDAB lipid mix was prepared by dissolution in t-butyl alcohol at 60 mg/mL followed by lyophilization in order to prepare a finely divided, homogeneous substrate for vesicle formation. Following lyophilization, the lipids were rehydrated with TE Buffer (10 mM TRIS, 1 mM EDTA. pH 8.0) at 60 mg/mL. The slurry was subjected to bath sonication for 5 minutes, which resulted in a uniform suspension of vesicles suitable for nucleic acid incorporation. To this suspension, a solution of 0.5 volume equivalent sheared DNA in TE buffer (0.15 mg/mL) was added for a final DNA concentration of 0.05 mg/mL. The sheared DNA was then incorporated into the liposomes using standard freeze-thaw methods whereby samples were frozen in liquid nitrogen (−196° C.) for 1 minute and then warmed to 45° C. for 15 minutes for a total of 5 cycles (Mayer, et.al., *Biochim et Biophys Acta* 817:193-196 (1985)). At this stage, the DNA was incorporated into the crude vesicles, which were multi-laminar and disparate in size.

Crude liposomes were subjected to extrusion, using the Avanti® Mini-Extruder (Avanti Polar Lipids, Part #: 610000) affixed with a Polycarbonate extrusion disk with 100 nm pores. Crude samples were processed, without dilution at 35-50° C., for a total of 31 total passages, resulting in a highly uniform size distribution.

Following extrusion, the liposomes were purified by anion exchange chromatography, by diluting the extruded liposomes to 20 mg/mL lipid in Tris buffer (50 mM) and passage over a 5 mL pre-packed HiTrap DEAE FF purification column (GE Healthcare, Part #: 17-5154-01). Purified liposomes (referred to as "Bulk LipoDNA") were collected in a 4 mL fraction, which was not retained by the column, while the unincorporated DNA remained bound to the stationary phase. Bound DNA can be subsequently eluted by increasing the salt concentration in the mobile phase to 1 M sodium chloride. The chromatographic profile was found to be comparable to that of other liposome preparations, supra. Qubit analysis of the purified lipid fractions were found to contain 40 ng/mL for mPEG2000-DMPE:DMPC:DDAB liposome control.

Example 19: Selecting Nucleic Acid Sizes

Placental genomic DNA (Sigma®; 1 mL at 150 ng/μL) was sheared using a Covaris instrument. Experiments were performed in PCR tubes starting with 50 μL of placental genomic DNA. The first size selection was made using Beckman Coulter Ampure Beads. The genomic placenta DNA and Ampure beads were mixed by pipetting up and down, centrifuged briefly to bring the material to the bottom of the tube, and incubated for 5 minutes at room temperature. The samples were placed on a magnetic 96-well rack for 5 minutes to remove the magnetic beads from solution. For the first size selection, the magnetic beads were removed and the supernatant was saved by transferring the sample to a new PCR tube. For the second round of size selection, additional Ampure Beads were added to the saved supernatant and mixed by pipetting up and down and centrifuge briefly to bring the material to the bottom of the tube followed by a 5 minutes incubation at room temperature. The samples were placed on the magnetic 96-well rack for 5 minutes to remove the magnetic beads from solution. For this instance of size selection, the supernatant is removed and the magnetic beads are saved. The magnetic beads were washed twice in 100 μL of 80% ethanol and allowed to dry for 5 minutes at room temperature. To elute the DNA off the magnetic beads, 50 μL of 0.1×TE buffer from Quality Biological was added and the beads were mixed by pipetting up and down followed by a 5 minutes incubation at room temperature. The tube was placed on the magnetic rack for 5 minutes to remove the beads and the supernatant was saved for analysis.

Samples were analyzed for DNA size distribution using an Agilent Bioanalyzer and the Agilent High Sensitivity DNA Kit. Samples were also analyzed for concentration using Invitrogen's Qubit fluorometer and the Qubit High Sensitivity Kit.

Ampure purification allowed for the selection of DNA with measured lengths ranging from approximately 144 base pairs to 194 base pairs at concentrations ranging from 8.7 ng/μL to 56.7 ng/μL (recovery of 5.8% to 37.8%).

Example 20: Controls Comprising Pegylated Liposomes

The viability of using normal female blood plasma as a source of background DNA (i.e. maternal fraction) was assessed. DMPC:DDAB liposomes were prepared containing 100% sheared DNA from either Trisomy 13 (T13) or Trisomy 18 (T18) primary cell lines. The DNA fragment size was ~170 nucleotides on average. T13 and T18 fragmented DNA was then encapsulated into liposomes and purified using methods similar to those described in Example 14. Plasma samples were collected from two healthy female donors in a 10 mL STRECK Cell-free DNA BCT®. Plasma fractions were isolated using conventional methods. To determine plasma DNA concentration, 3 mL of plasma from each donor was extracted in duplicate using a Qiagen QIAamp Circulating Nucleic Acid Kit, eluted into 50 μL of AVE buffer, and the DNA concentration determined using a Qubit® dsDNA HS Assay Kit (ThermoFisher Scientific). Liposome-containing DNA was then formulated into the two different plasma samples as indicated in Table 33. Liposomed fractions were also estimated based on the concentration of the DNA contained in the individual plasma samples and the concentration of the liposomed DNA and plasma DNA which were combined.

TABLE 33

Formulation of controls comprising liposomed trisomy DNA and female cfDNA

| Sample | Plasma Source | Plasma cfDNA conc. (ng/mL) | Plasma Volume (mL) | Liposomed DNA Source | Liposomed DNA Conc. (ng/mL) | Liposomed DNA sol. Volume (mL) | Estimated Liposomed Fraction (%) |
|---|---|---|---|---|---|---|---|
| Sample A | Female1 | 15.9 | 1 | 100% T13 | 5500 | 0.001 | 26% |
| Sample B | Female1 | 15.9 | 1 | 100% T18 | 3800 | 0.001 | 19% |
| Sample C | Female2 | 5.7 | 1 | 100% T13 | 5500 | 0.001 | 49% |
| Sample D | Female2 | 5.7 | 1 | 100% T18 | 3800 | 0.001 | 40% |

NCV values were determined by an external reference lab that routinely conducts NIPS assays. A linear relationship ($R^2=0.994$) was observed between the NCV for chromosome Y versus the formulated fetal fraction, indicating that efficacy of the formulation. The samples were also measured as being positive for trisomy 13 and trisomy 18 as evidenced by the NCV values for chromosomes 13 and 18 (Table 34; FIG. 33).

TABLE 34

Normalized Chromosome Values (NVCs) for male trisomy 13 and trisomy 18 controls formulated with female circulating cell-free DNA

|  | NCV Chr 13 | NCV Chr 18 | NCV Chr 21 | NCV Chr Y |
|---|---|---|---|---|
| Sample A | 63.94 | −0.75 | 0.44 | 127.17 |
| Sample B | 0.73 | 44.15 | 0.12 | 102.12 |
| Sample C | 103.34 | −1.87 | 0.38 | 208.40 |
| Sample D | −0.79 | 78.87 | −1.09 | 169.10 |

Controls comprising 1%, 2%, 4%, or 8% trisomy 21 DNA and 99%, 98%, 96%, or 92% female circulating cell-free DNA were prepared as described above. NCV values were determined by an external reference lab that routinely conducts NIPS assays. A linear relationship of NCV for chromosome 21 versus formulated trisomy 21 fraction was determined (FIG. 34, $R^2=0.9985$; Table 35). NCV values for chromosomes 13 and 18 did not correlate with trisomy 21 fraction percentage.

TABLE 35

Normalized Chromosome Values (NVCs) for trisomy 21 controls formulated with female circulating cell-free DNA

|  | Chr13 | Chr18 | Chr21 | T21CV |
|---|---|---|---|---|
| 1% | 1.21 | 1.15 | 1.81 | 0.17 |
| 2% | 0.45 | 0.56 | 3.12 | 0.18 |
| 4% | 0.56 | 0.57 | 5.53 | 0.14 |
| 8% | 1.74 | 0.22 | 11.27 | 0.09 |

INCORPORATION BY REFERENCE

All of the U.S. patents, and U.S. and PCT patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A control for use in determining the ploidy of a chromosome in a fetus, comprising:
a first mixture of nucleic acids comprising a first plurality of nucleotide sequences and a second plurality of nucleotide sequences, wherein each nucleotide sequence of the first plurality has sequence homology with a chromosome; each nucleotide sequence of the second plurality has sequence homology with at least one autosome, wherein the at least one autosome does not comprise the chromosome; and the ratio of the copy number for any nucleotide sequence in the first plurality to the copy number for any nucleotide sequence in the second plurality is about 3:2;
a second mixture of nucleic acids comprising a first plurality of nucleotide sequences and a second plurality of nucleotide sequences, wherein the ratio of the copy number for any nucleotide sequence in the first plurality to the copy number for any nucleotide sequence in the second plurality is about 1:1; and
liposomes;
wherein:
the first plurality of nucleotide sequences of the first mixture and the first plurality of nucleotide sequences of the second mixture consist of the same nucleotide sequences;
the second plurality of nucleotide sequences of the first mixture and the second plurality of nucleotide sequences of the second mixture consist of the same nucleotide sequences;
the first mixture of nucleic acids and the second mixture of nucleic acids are admixed in the control;
the first mixture of nucleic acids and the second mixture of nucleic acids are incorporated into the liposomes;
the first mixture of nucleic acids encodes substantially all of a first human genome, and the second mixture of nucleic acids consists of circulating, cell-free DNA obtained from a human donor; and
the average diameter of the liposomes is about 30 nm to about 300 nm.

2. The control of claim 1, wherein each of the at least one autosome is independently selected from the group consisting of human chromosome 1, 6, and 7.

3. The control of claim 1, wherein the chromosome is human chromosome 8, 9, 13, 18, 21, 22, or X.

4. The control of claim 1, wherein the first mixture of nucleic acids encodes substantially all of a first human genome and the second mixture of nucleic acids encodes substantially all of a second human genome.

5. The control of claim 4, wherein the first human genome is a cytotrophoblast cell line genome.

6. The control of claim 1, further comprising blood serum.

7. The control of claim 1, wherein the first plurality of nucleotide sequences of the first mixture encodes substantially all of the chromosome.

8. The control of claim 1, wherein the second plurality of nucleotide sequences of the first mixture encodes substantially all of at least one autosome that is not the chromosome.

9. The control of claim 8, wherein the second plurality of nucleotide sequences of the first mixture encodes substantially all of human chromosome 1, 6, or 7.

10. The control of claim 1, wherein the concentration of nucleic acids in the first mixture relative to the total concentration of nucleic acids in the control is about 1% to about 20% by weight.

11. The control of claim 10, wherein the concentration of nucleic acids in the first mixture relative to the total concentration of nucleic acids in the control is about 4% to about 18% by weight; and the concentration of nucleic acids in the second mixture relative to the total concentration of nucleic acids in the control is about 82% to about 96% by weight.

12. The control of claim 1, wherein the nucleic acids of the control are less likely to aggregate than nucleic acids of a control that does not comprise liposomes.

13. The control of claim 1, wherein the nucleic acids of the control are less likely to aggregate than a nucleic acid of a control that does not comprise liposomes when stored at a temperature between 2° C. to 42° C. for a period of about one month to about four months.

* * * * *